United States Patent
Blagg et al.

(10) Patent No.: US 10,927,076 B2
(45) Date of Patent: Feb. 23, 2021

(54) HSP90B N-TERMINAL ISOFORM-SELECTIVE INHIBITORS

(71) Applicant: University of Kansas, Lawrence, KS (US)

(72) Inventors: Brian S. J. Blagg, Niles, MI (US);
Caitlin Nicole Kent, South Bend, IN (US); Anuj Khandelwal, Urbana, IL (US); Sanket Jaiprakash Mishra, Mishawaka, IN (US)

(73) Assignee: University of Kansas, Lawrence, KS (US)

( * ) Notice: Subject to any disclaimer, the term of this patent is extended or adjusted under 35 U.S.C. 154(b) by 0 days.

(21) Appl. No.: 16/477,398

(22) PCT Filed: Jan. 12, 2018

(86) PCT No.: PCT/US2018/013666
§ 371 (c)(1),
(2) Date: Jul. 11, 2019

(87) PCT Pub. No.: WO2018/132769
PCT Pub. Date: Jul. 19, 2018

(65) Prior Publication Data
US 2019/0337894 A1    Nov. 7, 2019

Related U.S. Application Data

(60) Provisional application No. 62/445,529, filed on Jan. 12, 2017.

(51) Int. Cl.
| | | |
|---|---|---|
| C07D 209/44 | (2006.01) | |
| C07D 209/46 | (2006.01) | |
| C07D 403/06 | (2006.01) | |
| C07D 403/10 | (2006.01) | |
| C07D 413/06 | (2006.01) | |
| C07D 413/10 | (2006.01) | |
| A61P 35/04 | (2006.01) | |

(52) U.S. Cl.
CPC ............ *C07D 209/44* (2013.01); *A61P 35/04* (2018.01); *C07D 209/46* (2013.01); *C07D 403/06* (2013.01); *C07D 403/10* (2013.01); *C07D 413/06* (2013.01); *C07D 413/10* (2013.01)

(58) Field of Classification Search
CPC .. C07D 209/44; C07D 209/46; C07D 403/06; C07D 403/10; C07D 413/06; C07D 413/10
See application file for complete search history.

(56) References Cited

U.S. PATENT DOCUMENTS

| | | |
|---|---|---|
| 2008/0306063 A1 | 12/2008 | Abdellaoui et al. |
| 2010/0256137 A1 | 10/2010 | Buchstaller et al. |

FOREIGN PATENT DOCUMENTS

| | | |
|---|---|---|
| WO | WO-2006/117669 | 11/2006 |
| WO | WO-2008/044045 | 4/2008 |
| WO | WO-2008/044054 | 4/2008 |
| WO | WO-2009/030316 | 3/2009 |
| WO | WO-2015/089360 | 6/2015 |

OTHER PUBLICATIONS

Subbarao, et al.; "Hsp90 isoforms: functions, expression and clinical importance", FEBS Letters. 2004. vol. 562, pp. 11-15, entire document, especially: p. 13, col. 2, para 3.
Woodhead, et al.; "Discovery of (2,4-Dihydroxy-5-isopropylphenyl)-[5-(4-methylpiperazin-1-ylmethyl)-1,3-dihydroisondol-2-yl]methanone (AT13387), a Novel Inhibitor of the Molecular Chaperone Hsp90 by Fragment Based Drug Design", J. Med. Chem. 2010. vol. 53m pp. 5956-5969, entire document, especially: p. 5957, Table 1, Compound 1: p. 5957, Table 1, Compound 2: pp. 5957, Table 1, Compounds 3, 4: p. 5958, col. 2, para 2: p. 5963, col. 2, para 2, Compound 35: p. 5965, col. 2, para 1.
International Search Report re Application No. PCT/US18/13666 dated Apr. 4, 2018; 2 pages.
Extended European Search Report in EP Patent Application No. 18738991.1 dated Jun. 2, 2020 (8 pages).
Peterson, et al. "The hERG channel is dependent upon the Hsp90α isoform for maturation and trafficking." Mol. Pharm., Jun. 4, 2012; 9(6), pp. 1841-1846. doi:10.1021/mp300138n.

*Primary Examiner* — Laura L Stockton
(74) *Attorney, Agent, or Firm* — Foley & Lardner LLP

(57) ABSTRACT

The present technology provides compounds according to Formula (I) as well as compositions including such compounds useful for the treatment of cancers such as non-small cell lung cancer, bladder cancer, or colon cancer.

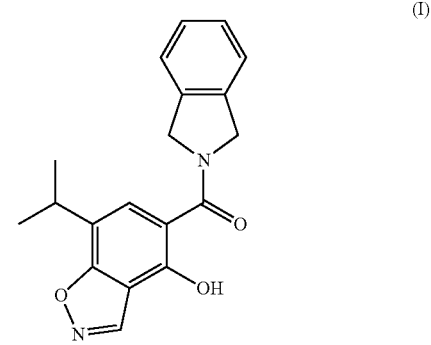

(I)

21 Claims, 6 Drawing Sheets

| Cancer Cell Line | (µM) |
|---|---|
| NCI-H23 | 6.74 + 1.1 |
| UC3 | 3.01 + 0.56 |
| HT29 | 3.72 + 0.34 |
| HEK-293 | >100 |

HSP90B N-TERMINAL ISOFORM-SELECTIVE INHIBITORS

CROSS-REFERENCE TO RELATED APPLICATIONS

This application is a U.S. national phase application under 35 U.S.C. § 371 of International Application No. PCT/US2018/013666, filed on Jan. 12, 2018, which claims the benefit of and priority to U.S. Provisional Patent Application No. 62/445,529, filed Jan. 12, 2017, the entire disclosures of which are hereby incorporated by reference in their entireties for any and all purposes.

U.S. GOVERNMENT LICENSE RIGHTS

This invention was made with government support under grant number CA109265 awarded by the National Institutes of Health. The government has certain rights in the invention.

FIELD

The present technology generally relates to Hsp90β N-terminal isoform-selective inhibitors, as well as compositions including such compounds and methods of use.

SUMMARY

In an aspect, a compound represented by Formula I is provided

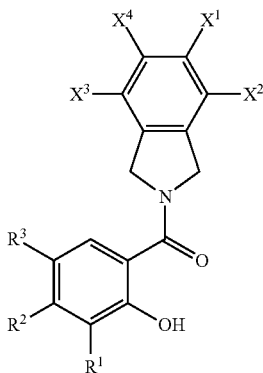

(I)

or a pharmaceutically acceptable salt and/or solvate thereof, where $X^1$, $X^2$, $X^3$, and $X^4$ are each independently selected from H, F, Cl, Br, I, sulfoxide, sulfone, nitro, pentafluorosulfanyl, C(O)OH, amide, or ester;

$R^1$ is H, OH, $C_1$-$C_3$ alkyl, $C_2$-$C_4$ alkenyl, or —$CH_2OH$;

$R^2$ is $CH_2$—$X^5$ or OH, where $X^5$ is OH, F, Cl, Br, CN, —C(O)—$NR^4R^5$, —$NR^6$—C(O)H, —$NR^7$—C(O)-alkyl, C(O)H, C(O)OH, sulfonamido, sulfoxide, sulfone, or $S(O)_2OH$;

or $R^1$ and $R^2$ together are (moving in the direction from $R^2$ to $R^1$) —$C(X^6)$—$CH_2$—, —$C(X^7)$—$CH(R^8)$—CH$(R^9)$—, —$C(X^8)$—$N(R^{10})$—$CH(R^{11})$—, —$C(X^9)$—$CH(R^{12})$—$CH(R^{13})$—$CH(R^{14})$—, —$C(X^{10})$—N$(R^{15})$—$CH(R^{16})$—$CH(R^{17})$—, —O—CH=CH—, —O—N=CH—, —NH—CH=N—, or —CH=N—NH—;

$X^6$, $X^7$, $X^8$, $X^9$, and $X^{10}$ are each independently selected from O, $CH_2$, and $CF_2$;

$R^3$ is alkyl, —$CH(CH_3)_2$, $CF_3$, Br, sulfonamido, sulfoxide, sulfone, nitro, pentafluorosulfanyl, C(O)OH, amide, or ester;

$R^4$, $R^5$, $R^6$, and $R^7$ are each independently H or alkyl;

$R^8$, $R^9$, $R^{11}$, $R^{12}$, $R^{13}$, $R^{14}$, $R^{16}$, and $R^{17}$ are each independently selected from H, $C_1$-$C_3$ alkyl, F, Cl, Br, I, or $CF_3$; and $R^{10}$ and $R^{15}$ are each independently H or $C_1$-$C_3$ alkyl.

In a related aspect, a composition is provided that includes a compound of the present technology and a pharmaceutically acceptable carrier.

In a further related aspect, a pharmaceutical composition is provided that includes an effective amount of a compound of the present technology and a pharmaceutically acceptable carrier, where the effective amount is effective for treating non-small cell lung cancer, bladder cancer, or colon cancer.

In an aspect, a method is provided that includes administering a compound of the present technology to a subject.

Also provided is a method for inhibiting cell motility of a cancer cell, where the method includes contacting the cancer cell with a compound of the present technology.

In a related aspect, a method of selectively inhibiting Hsp90β over Hsp90α is provided, where the method includes administering a compound of the present technology to a cancer cell and/or to a subject.

DETAILED DESCRIPTION

Figure 1A:
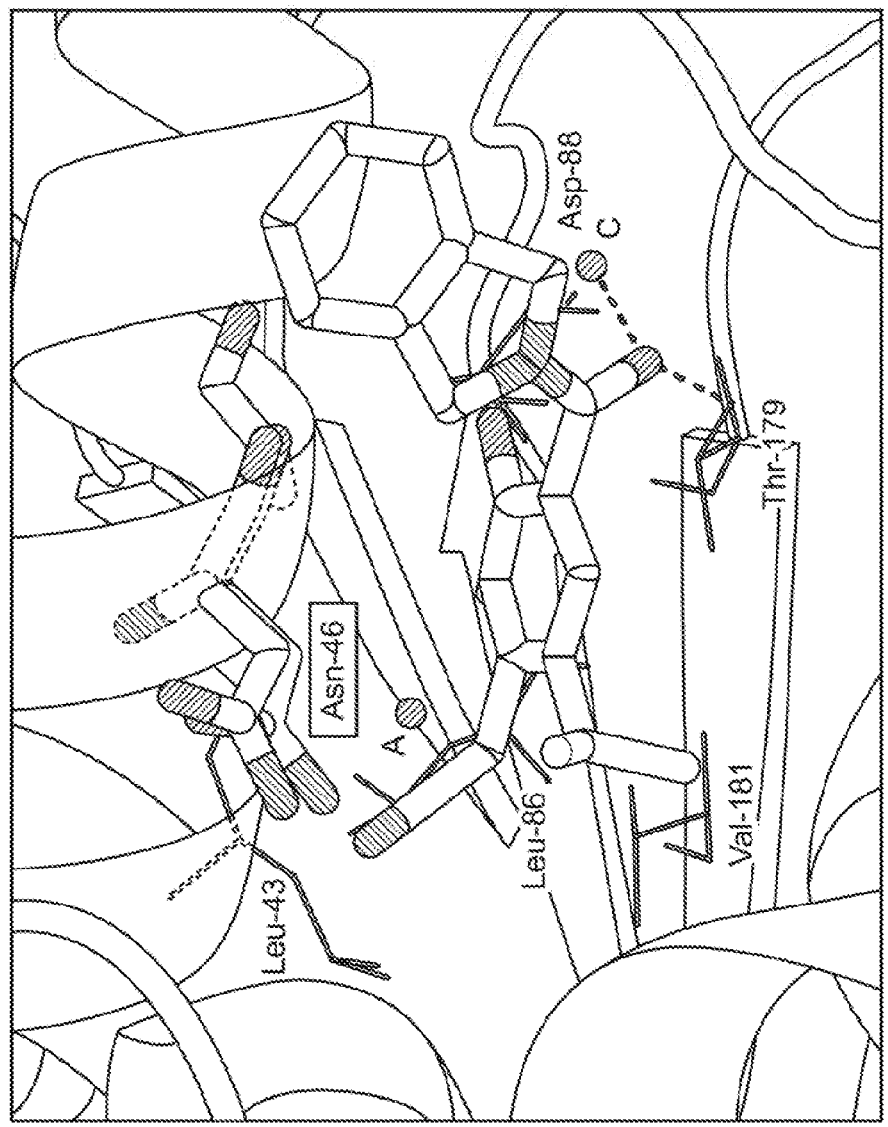
FIG. 1A illustrates the co-crystal structure of a compound of the present technology bound to Hsp90β and showing movement of Asn46, where the previous position of Asn46 is represented in pink and Asn46 in co-crystal structure of 2 is represented in blue.
Figure 1B:
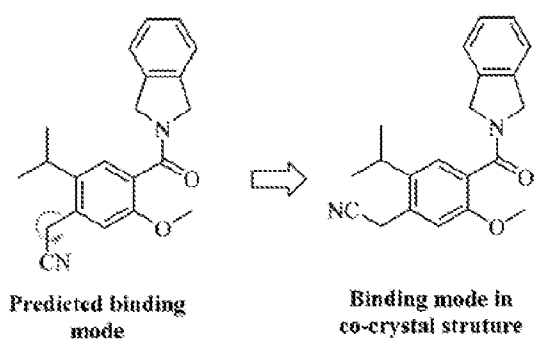
FIG. 1B illustrates the two-dimensional representation of potential binding modes of a compound of the present technology (KUNB30) to Hsp90β.

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the present technology. Procedures for inserting such labels into the compounds of the present technology will be readily apparent to those skilled in the art based on the disclosure herein.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, aryloxy, aralkyloxy, heterocyclyl, heterocyclylalkyl, heterocyclyloxy, and heterocyclylalkoxy groups; carbonyls (oxo); carboxylates; esters; urethanes; oximes; hydroxylamines; alkoxyamines; aralkoxyamines; thiols; sulfides; sulfoxides; sulfones; sulfonyls; pentafluorosulfanyl (i.e., $SF_5$), sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

Substituted ring groups such as substituted cycloalkyl, aryl, heterocyclyl and heteroaryl groups also include rings and ring systems in which a bond to a hydrogen atom is replaced with a bond to a carbon atom. Therefore, substituted cycloalkyl, aryl, heterocyclyl and heteroaryl groups may also be substituted with substituted or unsubstituted alkyl, alkenyl, and alkynyl groups as defined below.

As used herein, $C_m$-$C_n$, such as $C_1$-$C_{12}$, $C_1$-$C_8$, or $C_1$-$C_6$ when used before a group refers to that group containing m to n carbon atoms.

Alkyl groups include straight chain and branched chain alkyl groups having from 1 to 12 carbon atoms, and typically from 1 to 10 carbons or, in some embodiments, from 1 to 8, 1 to 6, or 1 to 4 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Alkyl groups may be substituted or unsubstituted. Representative substituted alkyl groups may be substituted one or more times with substituents such as those listed above, and include without limitation haloalkyl (e.g., trifluoromethyl), hydroxyalkyl, thioalkyl, aminoalkyl, alkylaminoalkyl, dialkylaminoalkyl, alkoxyalkyl, carboxyalkyl, and the like.

Cycloalkyl groups include mono-, bi- or tricyclic alkyl groups having from 3 to 12 carbon atoms in the ring(s), or, in some embodiments, 3 to 10, 3 to 8, or 3 to 4, 5, or 6 carbon atoms. Exemplary monocyclic cycloalkyl groups include, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Bi- and tricyclic ring systems include both bridged cycloalkyl groups and fused rings, such as, but not limited to, bicyclo[2.1.1] hexane, adamantyl, decalinyl, and the like. Cycloalkyl groups may be substituted or unsubstituted. Substituted cycloalkyl groups may be substituted one or more times with, non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4- 2,5- or 2,6-disubstituted cyclohexyl groups, which may be substituted with substituents such as those listed above.

Cycloalkylalkyl groups are alkyl groups as defined above in which a hydrogen or carbon bond of an alkyl group is replaced with a bond to a cycloalkyl group as defined above. In some embodiments, cycloalkylalkyl groups have from 4 to 16 carbon atoms, 4 to 12 carbon atoms, and typically 4 to 10 carbon atoms. Cycloalkylalkyl groups may be substituted or unsubstituted. Substituted cycloalkylalkyl groups may be substituted at the alkyl, the cycloalkyl or both the alkyl and cycloalkyl portions of the group. Representative substituted cycloalkylalkyl groups may be mono-substituted or substituted more than once, such as, but not limited to, mono-, di- or tri-substituted with substituents such as those listed above.

Alkenyl groups include straight and branched chain alkyl groups as defined above, except that at least one double bond exists between two carbon atoms. Alkenyl groups have from 2 to 12 carbon atoms, and typically from 2 to 10 carbons or, in some embodiments, from 2 to 8, 2 to 6, or 2 to 4 carbon atoms. In some embodiments, the alkenyl group has one, two, or three carbon-carbon double bonds. Examples include, but are not limited to vinyl, allyl, —CH═CH(CH$_3$), —CH═C(CH$_3$)$_2$, —C(CH$_3$)═CH$_2$, —C(CH$_3$)═CH(CH$_3$), —C(CH$_2$CH$_3$)═CH$_2$, among others. Alkenyl groups may be substituted or unsubstituted. Representative substituted alkenyl groups may be mono-substituted or substituted more than once, such as, but not limited to, mono-, di- or tri-substituted with substituents such as those listed above.

Cycloalkenyl groups include cycloalkyl groups as defined above, having at least one double bond between two carbon atoms. Cycloalkenyl groups may be substituted or unsubstituted. In some embodiments the cycloalkenyl group may have one, two or three double bonds but does not include aromatic compounds. Cycloalkenyl groups have from 4 to 14 carbon atoms, or, in some embodiments, 5 to 14 carbon atoms, 5 to 10 carbon atoms, or even 5, 6, 7, or 8 carbon atoms. Examples of cycloalkenyl groups include cyclohexenyl, cyclopentenyl, cyclohexadienyl, cyclobutadienyl, and cyclopentadienyl.

Cycloalkenylalkyl groups are alkyl groups as defined above in which a hydrogen or carbon bond of the alkyl group is replaced with a bond to a cycloalkenyl group as defined above. Cycloalkenylalkyl groups may be substituted or unsubstituted. Substituted cycloalkenylalkyl groups may be substituted at the alkyl, the cycloalkenyl or both the alkyl and cycloalkenyl portions of the group. Representative substituted cycloalkenylalkyl groups may be substituted one or more times with substituents such as those listed above.

Alkynyl groups include straight and branched chain alkyl groups as defined above, except that at least one triple bond exists between two carbon atoms. Alkynyl groups have from 2 to 12 carbon atoms, and typically from 2 to 10 carbons or, in some embodiments, from 2 to 8, 2 to 6, or 2 to 4 carbon atoms. In some embodiments, the alkynyl group has one, two, or three carbon-carbon triple bonds. Examples include, but are not limited to —C≡CH, —C≡CCH$_3$, —CH$_2$C≡CCH$_3$, —C≡CCH$_2$CH(CH$_2$CH$_3$)$_2$, among others. Alkynyl groups may be substituted or unsubstituted. Representative substituted alkynyl groups may be mono-substituted or substituted more than once, such as, but not limited to, mono-, di- or tri-substituted with substituents such as those listed above.

Aryl groups are cyclic aromatic hydrocarbons that do not contain heteroatoms. Aryl groups herein include monocyclic, bicyclic and tricyclic ring systems. Thus, aryl groups include, but are not limited to, phenyl, azulenyl, heptalenyl, biphenyl, fluorenyl, phenanthrenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. In some embodiments, the aryl groups are phenyl or naphthyl. Aryl groups may be substituted or unsubstituted. The phrase "aryl groups" includes groups containing fused rings, such as fused aromatic-aliphatic ring systems (e.g., indanyl, tetrahydronaphthyl, and the like). Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

Aralkyl groups are alkyl groups as defined above in which a hydrogen or carbon bond of an alkyl group is replaced with a bond to an aryl group as defined above. In some embodiments, aralkyl groups contain 7 to 16 carbon atoms, 7 to 14 carbon atoms, or 7 to 10 carbon atoms. Aralkyl groups may be substituted or unsubstituted. Substituted aralkyl groups may be substituted at the alkyl, the aryl or both the alkyl and aryl portions of the group. Representative aralkyl groups include but are not limited to benzyl and phenethyl groups and fused (cycloalkylaryl)alkyl groups such as 4-indanylethyl. Representative substituted aralkyl groups may be substituted one or more times with substituents such as those listed above.

Heterocyclyl groups include aromatic (also referred to as heteroaryl) and non-aromatic ring compounds containing 3 or more ring members, of which one or more is a heteroatom such as, but not limited to, N, O, and S. In some embodiments, the heterocyclyl group contains 1, 2, 3 or 4 heteroatoms. In some embodiments, heterocyclyl groups include mono-, bi- and tricyclic rings having 3 to 16 ring members, whereas other such groups have 3 to 6, 3 to 10, 3 to 12, or 3 to 14 ring members. Heterocyclyl groups encompass aromatic, partially unsaturated and saturated ring systems, such as, for example, imidazolyl, imidazolinyl and imidazolidinyl groups. The phrase "heterocyclyl group" includes fused ring species including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. Heterocyclyl groups may be substituted or unsubstituted. Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed above.

Heteroaryl groups are aromatic ring compounds containing 5 or more ring members, of which, one or more is a heteroatom such as, but not limited to, N, O, and S. Heteroaryl groups include, but are not limited to, groups such as pyrrolyl, pyrazolyl, triazolyl, tetrazolyl, oxazolyl, isoxazolyl, thiazolyl, pyridinyl, pyridazinyl, pyrimidinyl, pyrazinyl, thiophenyl, benzothiophenyl, furanyl, benzofuranyl, indolyl, azaindolyl (pyrrolopyridinyl), indazolyl, benzimidazolyl, imidazopyridinyl (azabenzimidazolyl), pyrazolopyridinyl, triazolopyridinyl, benzotriazolyl, benzoxazolyl, benzothiazolyl, benzothiadiazolyl, imidazopyridinyl, isoxazolopyridinyl, thianaphthyl, purinyl, xanthinyl, adeninyl, guaninyl, quinolinyl, isoquinolinyl, tetrahydroquinolinyl, quinoxalinyl, and quinazolinyl groups. Heteroaryl groups include fused ring compounds in which all rings are aromatic such as indolyl groups and include fused ring compounds in which only one of the rings is aromatic, such as 2,3-dihydro indolyl groups. Heteroaryl groups may be substituted or unsubstituted. Thus, the phrase "heteroaryl groups" includes fused ring compounds as well as includes heteroaryl groups that have other groups bonded to one of the ring members, such as alkyl groups. Representative substituted heteroaryl groups may be substituted one or more times with various substituents such as those listed above.

Heterocyclylalkyl groups are alkyl groups as defined above in which a hydrogen or carbon bond of an alkyl group is replaced with a bond to a heterocyclyl group as defined above. Heterocyclylalkyl groups may be substituted or unsubstituted. Substituted heterocyclylalkyl groups may be substituted at the alkyl, the heterocyclyl or both the alkyl and heterocyclyl portions of the group. Representative heterocyclyl alkyl groups include, but are not limited to, morpholin-4-yl-ethyl, furan-2-yl-methyl, imidazol-4-yl-methyl, pyridin-3-yl-methyl, tetrahydrofuran-2-yl-ethyl, and indol-2-yl-propyl. Representative substituted heterocyclylalkyl groups may be substituted one or more times with substituents such as those listed above.

Heteroaralkyl groups are alkyl groups as defined above in which a hydrogen or carbon bond of an alkyl group is replaced with a bond to a heteroaryl group as defined above. Heteroaralkyl groups may be substituted or unsubstituted. Substituted heteroaralkyl groups may be substituted at the alkyl, the heteroaryl or both the alkyl and heteroaryl portions of the group. Representative substituted heteroaralkyl groups may be substituted one or more times with substituents such as those listed above.

Groups described herein having two or more points of attachment (i.e., divalent, trivalent, or polyvalent) within the compound of the present technology are designated by use of the suffix, "ene." For example, divalent alkyl groups are alkylene groups, divalent aryl groups are arylene groups, divalent heteroaryl groups are divalent heteroarylene groups, and so forth. Substituted groups having a single point of attachment to the compound of the present technology are not referred to using the "ene" designation. Thus, e.g., chloroethyl is not referred to herein as chloroethylene. Such groups may further be substituted or unsubstituted.

Alkoxy groups are hydroxyl groups (—OH) in which the bond to the hydrogen atom is replaced by a bond to a carbon atom of a substituted or unsubstituted alkyl group as defined above. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Alkoxy groups may be substituted or unsubstituted. Representative substituted alkoxy groups may be substituted one or more times with substituents such as those listed above.

The terms "alkanoyl" and "alkanoyloxy" as used herein can refer, respectively, to —C(O)-alkyl and —O—C(O)-alkyl groups, where in some embodiments the alkanoyl or alkanoyloxy groups each contain 2-5 carbon atoms. Similarly, the terms "aryloyl" and "aryloyloxy" respectively refer to —C(O)-aryl and —O—C(O)-aryl groups.

The terms "aryloxy" and "arylalkoxy" refer to, respectively, a substituted or unsubstituted aryl group bonded to an oxygen atom and a substituted or unsubstituted aralkyl group bonded to the oxygen atom at the alkyl. Examples include but are not limited to phenoxy, naphthyloxy, and benzyloxy. Representative substituted aryloxy and arylalkoxy groups may be substituted one or more times with substituents such as those listed above.

The term "carboxylic acid" as used herein refers to a compound with a —C(O)OH group. The term "carboxylate" as used herein refers to a —C(O)O$^-$ group. A "protected carboxylate" refers to a —C(O)O-G where G is a carboxylate protecting group. Carboxylate protecting groups are well known to one of ordinary skill in the art. An extensive list of protecting groups for the carboxylate group functionality may be found in Protective Groups in Organic Synthesis, Greene, T. W.; Wuts, P. G. M., John Wiley & Sons, New York, N.Y., (3rd Edition, 1999) which can be added or removed using the procedures set forth therein and which is hereby incorporated by reference in its entirety and for any and all purposes as if fully set forth herein.

The term "ester" as used herein refers to —COOR$^{70}$ groups. R$^{70}$ is a substituted or unsubstituted alkyl, cycloalkyl, alkenyl, alkynyl, aryl, aralkyl, heterocyclylalkyl or heterocyclyl group as defined herein.

The term "amide" (or "amido") includes C- and N-amide groups, i.e., —C(O)NR$^{71}$R$^{72}$, and —NR$^{71}$C(O)R$^{72}$ groups, respectively. R$^{71}$ and R$^{72}$ are independently hydrogen, or a substituted or unsubstituted alkyl, alkenyl, alkynyl, cycloalkyl, aryl, aralkyl, heterocyclylalkyl or heterocyclyl group as defined herein. Amido groups therefore include but are not limited to carbamoyl groups (—C(O)NH$_2$) and formamide groups (—NHC(O)H). In some embodiments, the amide is —NR$^{71}$C(O)—(C$_{1-5}$ alkyl) and the group is termed "carbonylamino," and in others the amide is —NHC(O)-alkyl and the group is termed "alkanoylamino."

The term "nitrile" or "cyano" as used herein refers to the —CN group.

Urethane groups include N- and O-urethane groups, i.e., —NR$^{73}$C(O)OR$^{74}$ and —OC(O)NR$^{73}$R$^{74}$ groups, respectively. R$^{73}$ and R$^{74}$ are independently a substituted or unsubstituted alkyl, alkenyl, alkynyl, cycloalkyl, aryl, aralkyl, heterocyclylalkyl, or heterocyclyl group as defined herein. R$^{73}$ may also be H.

The term "amine" (or "amino") as used herein refers to —NR$^{75}$R$^{76}$ groups, wherein R$^{75}$ and R$^{76}$ are independently hydrogen, or a substituted or unsubstituted alkyl, alkenyl, alkynyl, cycloalkyl, aryl, aralkyl, heterocyclylalkyl or heterocyclyl group as defined herein. In some embodiments, the amine is alkylamino, dialkylamino, arylamino, or alkylarylamino. In other embodiments, the amine is NH$_2$, methylamino, dimethylamino, ethylamino, diethylamino, propylamino, isopropylamino, phenylamino, or benzylamino.

The term "sulfonamido" includes S- and N-sulfonamide groups, i.e., —SO$_2$NR$^{78}$R$^{79}$ and —NR$^{78}$SO$_2$R$^{79}$ groups, respectively. R$^{78}$ and R$^{79}$ are independently hydrogen, or a substituted or unsubstituted alkyl, alkenyl, alkynyl, cycloalkyl, aryl, aralkyl, heterocyclylalkyl, or heterocyclyl group as defined herein. Sulfonamido groups therefore include but are not limited to sulfamoyl groups (—SO$_2$NH$_2$). In some embodiments herein, the sulfonamido is —NHSO$_2$-alkyl and is referred to as the "alkylsulfonylamino" group.

The term "thiol" refers to —SH groups, while sulfides include —SR$^{80}$ groups, sulfoxides include —S(O)R$^{81}$ groups, sulfones include —SO$_2$R$^{82}$ groups, and sulfonyls include —SO$_2$OR$^{83}$. R$^{80}$, R$^{81}$, R$^{82}$, and R$^{83}$ are each independently a substituted or unsubstituted alkyl, cycloalkyl, alkenyl, alkynyl, aryl aralkyl, heterocyclyl or heterocyclylalkyl group as defined herein. In some embodiments the sulfide is an alkylthio group, —S-alkyl.

The term "urea" refers to —NR$^{84}$—C(O)—NR$^{85}$R$^{86}$ groups. R$^{84}$, R$^{85}$, and R$^{86}$ groups are independently hydrogen, or a substituted or unsubstituted alkyl, alkenyl, alkynyl, cycloalkyl, aryl, aralkyl, heterocyclyl, or heterocyclylalkyl group as defined herein.

The term "amidine" refers to —C(NR$^{87}$)NR$^{88}$R$^{89}$ and —NR$^{87}$C(NR$^{88}$)R$^{89}$, wherein R$^{87}$, R$^{88}$, and R$^{89}$ are each independently hydrogen, or a substituted or unsubstituted alkyl, cycloalkyl, alkenyl, alkynyl, aryl aralkyl, heterocyclyl or heterocyclylalkyl group as defined herein.

The term "guanidine" refers to —NR$^{90}$C(NR$^{91}$)NR$^{92}$R$^{93}$, wherein R$^{90}$, R$^{91}$, R$^{92}$ and R$^{93}$ are each independently hydrogen, or a substituted or unsubstituted alkyl, cycloalkyl, alkenyl, alkynyl, aryl aralkyl, heterocyclyl or heterocyclylalkyl group as defined herein.

The term "enamine" refers to —C(R$^{94}$)=C(R$^{95}$)NR$^{96}$R$^{97}$ and —NR$^{94}$C(R$^{95}$)=C(R$^{96}$)R$^{97}$, wherein R$^{94}$, R$^{95}$, R$^{96}$ and R$^{97}$ are each independently hydrogen, a substituted or unsubstituted alkyl, cycloalkyl, alkenyl, alkynyl, aryl aralkyl, heterocyclyl or heterocyclylalkyl group as defined herein.

The term "halogen" or "halo" as used herein refers to bromine, chlorine, fluorine, or iodine. In some embodiments, the halogen is fluorine. In other embodiments, the halogen is chlorine or bromine.

The term "hydroxyl" as used herein can refer to —OH or its ionized form, —O$^-$.

The term "imide" refers to —C(O)NR$^{98}$C(O)R$^{99}$, wherein R$^{98}$ and R$^{99}$ are each independently hydrogen, or a substituted or unsubstituted alkyl, cycloalkyl, alkenyl, alkynyl, aryl aralkyl, heterocyclyl or heterocyclylalkyl group as defined herein.

The term "imine" refers to —CR$^{100}$(NR$^{101}$) and —N(CR$^{100}$R$^{101}$) groups, wherein R$^{100}$ and R$^{101}$ are each independently hydrogen or a substituted or unsubstituted alkyl, cycloalkyl, alkenyl, alkynyl, aryl aralkyl, heterocyclyl or heterocyclylalkyl group as defined herein, with the proviso that R$^{100}$ and R$^{101}$ are not both simultaneously hydrogen.

The term "nitro" as used herein refers to an —NO$_2$ group.

The term "trifluoromethyl" as used herein refers to —CF$_3$.

The term "trifluoromethoxy" as used herein refers to —OCF$_3$.

The term "azido" refers to —N$_3$.

The term "trialkyl ammonium" refers to a —N(alkyl)$_3$ group. A trialkylammonium group is positively charged and thus typically has an associated anion, such as halogen anion.

The term "trifluoromethyldiazirido" refers to

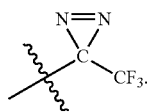

The term "isocyano" refers to —NC.
The term "isothiocyano" refers to —NCS.
The term "pentafluorosulfanyl" refers to —SF$_5$.

The phrase "selective" as used herein will be understood by persons of ordinary skill in the art and will vary to some extent depending upon the context in which the phrase is used. If there are uses of the phrase which are not clear to persons of ordinary skill in the art, given the context in which the phrase is used, the phrase at minimum when referring to a compound of the present technology refers to the compounds acting with a selectivity ratio for Hsp90β over Hsp90α of at least about 2:1, such as at least about 4:1, at least about 10:1, at least about 20:1, at least about 30:1, at least about 50:1, at least about 70:1. Such selectivity results in fewer off-target effects.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

Pharmaceutically acceptable salts of compounds described herein are within the scope of the present technology and include acid or base addition salts which retain the desired pharmacological activity and is not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g., alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g., Na$^+$, Li$^+$, K$^+$, Ca$^{2+}$, Mg$^{2+}$, Zn$^{2+}$), ammonia or organic amines (e.g. dicyclohexylamine, trimethylamine, triethylamine, pyridine, picoline, ethanolamine, diethanolamine, triethanolamine) or basic amino acids (e.g., arginine, lysine and ornithine). Such salts can be prepared in situ during isolation and purification of the compounds or by separately reacting the purified compound in its free base or free acid form with a suitable acid or base, respectively, and isolating the salt thus formed.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as mixtures of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, quinazolinones may exhibit the following isomeric forms, which are referred to as tautomers of each other:

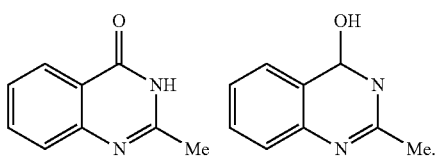

As another example, guanidines may exhibit the following isomeric forms in protic organic solution, also referred to as tautomers of each other:

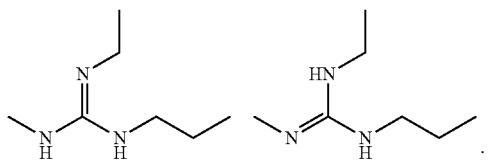

Because of the limits of representing compounds by structural formulas, it is to be understood that all chemical formulas of the compounds described herein represent all tautomeric forms of compounds and are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

The compounds of the present technology may exist as solvates, especially hydrates. Hydrates may form during manufacture of the compounds or compositions comprising the compounds, or hydrates may form over time due to the hygroscopic nature of the compounds. Compounds of the present technology may exist as organic solvates as well, including DMF, ether, and alcohol solvates among others. The identification and preparation of any particular solvate is within the skill of the ordinary artisan of synthetic organic or medicinal chemistry.

Throughout this disclosure, various publications, patents and published patent specifications are referenced by an identifying citation. Also within this disclosure are Arabic numerals referring to referenced citations, the full bibliographic details of which are provided immediately preceding the claims. The disclosures of these publications, patents and published patent specifications are hereby incorporated by reference into the present disclosure to more fully describe the state of the art to which this invention pertains.

The Present Technology

The 90 kD heat shock protein (Hsp90), is a molecular chaperone responsible for folding proteins that are directly associated with cancer progression. The Hsp90 family of proteins consist of four isoforms. Hsp90β is constitutively expressed in the cytoplasm, Hsp90α is expressed in the cytosol in response to cellular stress, Grp94 resides in the endoplasmic reticulum, and Trap-1 is localized to the mitochondria.[1-3] Together, these molecular chaperones are responsible for the conformational maturation, activation, and/or trafficking of ~300 Hsp90-dependent substrates.[4-9] Many of the proteins dependent upon Hsp90 are essential to the growth and proliferation of cancer cells. In fact, proteins associated with all ten hallmarks of cancer are dependent upon the Hsp90 protein folding machinery.[10] Consequently, Hsp90 is a target in anticancer chemotherapeutics.[11-13]

Seventeen small molecule inhibitors of Hsp90 have entered clinical trials, all of which exhibit pan Hsp90 inhibitory activity against all four isoforms.[14-17] Many of the compounds have produced cardiotoxicity, gastrointestinal toxicity, and/or ocular toxicity amongst other side effects.[18-22] Recent studies have determined that maturation of the hERG channel is also Hsp90 dependent, and specifically depends upon the Hsp90α isoform.[23] In addition, pan-Hsp90 inhibition induces the pro-survival heat shock response, which leads to induction of Hsp27, Hsp40, Hsp70, and Hsp90, requiring the escalation of doses to overcome increased Hsp90 expression.[24-26] Among all four isoforms, specific roles for Grp94 and the consequences of the selective Grp94-inhibition have been deconvoluted. Selective Grp94 inhibition has emerged as a promising approach for the treatment of glaucoma, and multiple myeloma and, metastasis. Recent studies have shown Grp94 inhibition represents a non-toxic approach to treat Her2 positive cancers. Collectively, these findings highlight the advantages of isoform-selective Hsp90 inhibition and warrant the better understanding of the specific roles of individual isoforms.

Hydrolysis of ATP by the N-terminal nucleoside binding pocket is required for the maturation of client protein substrates, and all four Hsp90's share >70% identity in this region and 21 out of the 29 residues are totally conserved and remaining 8 share high degree of similarity.[27-29] Consequently, the discovery of isoform-selective inhibitors has been challenging.[30,31] Three scaffolds manifesting Grp94-selective inhibition were recently reported.[32-34] However, Hsp90α and Hsp90β share ~95% identity in this binding site and only two amino acids differ between these isoforms, making the development of Hsp90α- or Hsp90β-selective inhibitors most challenging.

The present technology provides compounds unlike any previously described inhibitors of Hsp90. The compounds of the present technology are Hsp90β-selective. Thus, the compounds and compositions of the present technology provide new Hsp90β-selective inhibitors that are useful for the treatment of cancer.

Accordingly, in an aspect, a compound represented by Formula I is provided

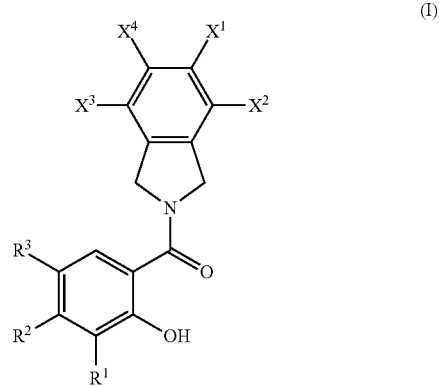

(I)

or a pharmaceutically acceptable salt and/or solvate thereof, where $X^1$, $X^2$, $X^3$, and $X^4$ are each independently selected from H, F, Cl, Br, I, sulfoxide, sulfone, nitro, pentafluorosulfanyl, C(O)OH, amide, or ester;

$R^1$ is H, OH, $C_1$-$C_3$ alkyl, $C_2$-$C_4$ alkenyl, or —$CH_2OH$;

$R^2$ is $CH_2$—$X^5$ or OH, where $X^5$ is OH, F, Cl, Br, CN, —C(O)—$NR^4R^5$, —$NR^6$—C(O)H, —$NR^7$—C(O)-alkyl, C(O)H, C(O)OH, sulfonamido, sulfoxide, sulfone, or $S(O)_2OH$;

or $R^1$ and $R^2$ together are (moving in the direction from $R^2$ to $R^1$) —C($X^6$)—$CH_2$—, —C($X^7$)—CH($R^8$)—CH($R^9$)—, —C($X^8$)—N($R^{10}$)—CH($R^{11}$)—, —C($X^9$)—CH($R^{12}$)—CH($R^{13}$)—CH($R^{14}$)—, —C($X^{10}$)—N($R^{15}$)—CH($R^{16}$)—CH($R^{17}$)—, —O—CH=CH—, —O—N=CH—, —NH—CH=N—, or —CH=N—NH—;

$X^6$, $X^7$, $X^8$, $X^9$, and $X^{10}$ are each independently selected from O, $CH_2$, and $CF_2$;

$R^3$ is alkyl, —CH($CH_3$)$_2$, $CF_3$, Br, sulfonamido, sulfoxide, sulfone, nitro, pentafluorosulfanyl, C(O)OH, amide, or ester;

$R^4$, $R^5$, $R^6$, and $R^7$ are each independently H or alkyl;

$R^8$, $R^9$, $R^{11}$, $R^{12}$, $R^{13}$, $R^{14}$, $R^{16}$, and $R^{17}$ are each independently selected from H, $C_1$-$C_3$ alkyl, F, Cl, Br, I, or $CF_3$; and $R^{10}$ and $R^{15}$ are each independently H or $C_1$-$C_3$ alkyl.

In any embodiment herein, the compound of Formula I may be of Formula II

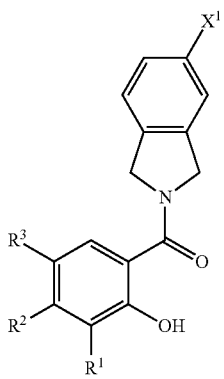

(II)

or a pharmaceutically acceptable salt and/or solvate thereof. In any embodiment herein of a compound of Formula I or Formula II, $R^1$ may be H, OH, methyl, ethyl, propyl, vinyl, or —$CH_2OH$. In any embodiment herein of a compound of Formula I or Formula II, $R^2$ is $CH_2$—$X^5$ or OH, where $X^5$ is OH, F, CN, —C(O)—$NR^4R^5$, —$NR^6$—C(O)H, —$NR^7$—C(O)-alkyl, C(O)H, C(O)OH, or S(O)$_2$OH.

The compound of Formula I may be a compound of Formula III

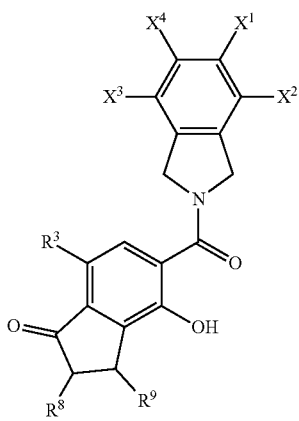

(III)

or a pharmaceutically acceptable salt and/or solvate thereof, or a compound of Formula IV

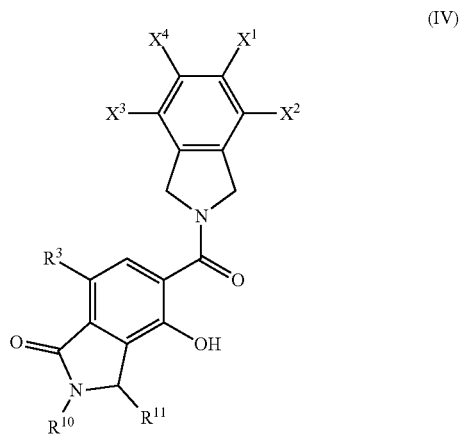

(IV)

or a pharmaceutically acceptable salt and/or solvate thereof.

In any embodiment herein, $R^3$ may be alkyl, —CH($CH_3$)$_2$, $CF_3$, Br, sulfoxide, sulfone, nitro, pentafluorosulfanyl, C(O)OH, amide, or ester. $X^1$ in any embodiment herein may be H, F, Cl, Br, or I. $X^2$, $X^3$, and $X^4$ in any embodiment herein may each independently be H. $X^5$ in any embodiment herein may be OH, F, Cl, Br, CN, —C(O)—$NH_2$, —NH—C(O)H, —NH—C(O)-alkyl, —C(O)H, or —C(O)OH.

The present technology provides compositions (e.g., pharmaceutical compositions) and medicaments comprising any of one of the embodiments of the compounds of Formulas I-IV (or a pharmaceutically acceptable salt thereof) disclosed herein and a pharmaceutically acceptable carrier or one or more excipients or fillers. The compositions may be used in the methods and treatments described herein. The pharmaceutical composition may include an effective amount of any of one of the embodiments of the compounds of the present technology disclosed herein. In any of the above embodiments, the effective amount may be determined in relation to a subject. "Effective amount" refers to the amount of a compound or composition required to produce a desired effect. One non-limiting example of an effective amount includes amounts or dosages that yield acceptable toxicity and bioavailability levels for therapeutic (pharmaceutical) use including, but not limited to, the treatment of non-small cell lung cancer, bladder cancer, colon cancer (such as colon adenocarcinoma). Another example of an effective amount includes amounts or dosages that are capable of reducing symptoms associated with non-small cell lung cancer, bladder cancer, or colon cancer (such as colon adenocarcinoma), such as, for example, reduction in proliferation and/or metastasis of non-small cell lung cancer, bladder cancer, or colon cancer (such as colon adenocarcinoma). The effective amount may be from about 0.01 µg to about 1 mg of the compound per gram of the composition, and preferably from about 0.1 µg to about 500 µg of the compound per gram of the composition. As used herein, a "subject" or "patient" is a mammal, such as a cat, dog, rodent or primate. Typically the subject is a human, and, preferably, a human suffering from or suspected of suffering from non-small cell lung cancer, bladder cancer, or colon cancer (such as colon adenocarcinoma). The term "subject" and "patient" can be used interchangeably.

In any of the embodiments of the present technology described herein, the pharmaceutical composition may be packaged in unit dosage form. The unit dosage form is effective in treating non-small cell lung cancer, bladder cancer, or colon cancer (such as colon adenocarcinoma). Generally, a unit dosage including a compound of the present technology will vary depending on patient considerations. Such considerations include, for example, age, protocol, condition, sex, extent of disease, contraindications, concomitant therapies and the like. An exemplary unit dosage based on these considerations may also be adjusted or modified by a physician skilled in the art. For example, a unit dosage for a patient comprising a compound of the present technology may vary from $1 \times 10^{-4}$ g/kg to 1 g/kg, preferably, $1 \times 10^{-3}$ g/kg to 1.0 g/kg. Dosage of a compound of the present technology may also vary from 0.01 mg/kg to 100 mg/kg or, preferably, from 0.1 mg/kg to 10 mg/kg. Suitable unit dosage forms, include, but are not limited to powders, tablets, pills, capsules, lozenges. suppositories. patches. nasal sprays, injectibles, implantable sustained-release formulations, rnucoadherent films, topical varnishes, lipid complexes, etc.

The pharmaceutical compositions may be prepared by mixing one or more compounds of Formulas I-IV, pharmaceutically acceptable salts thereof, stereoisomers thereof, tautomers thereof, or solvates thereof, with pharmaceutically acceptable carriers, excipients, binders, diluents or the like to prevent and treat disorders associated with non-small cell lung cancer, bladder cancer, or colon cancer (such as colon adenocarcinoma). The compounds and compositions described herein may be used to prepare formulations and medicaments that treat non-small cell lung cancer, bladder cancer, or colon cancer (such as colon adenocarcinoma). Such compositions may be in the form of, for example, granules, powders, tablets, capsules, syrup, suppositories, injections, emulsions, elixirs, suspensions or solutions. The instant compositions may be formulated for various routes of administration, for example, by oral, parenteral, topical, rectal, nasal, vaginal administration, or via implanted reservoir. Parenteral or systemic administration includes, but is not limited to, subcutaneous, intravenous, intraperitoneal, and intramuscular, injections. The following dosage forms are given by way of example and should not be construed as limiting the instant present technology.

For oral, buccal, and sublingual administration, powders, suspensions, granules, tablets, pills, capsules, gelcaps, and caplets are acceptable as solid dosage forms. These can be prepared, for example, by mixing one or more compounds of the instant present technology, or pharmaceutically acceptable salts or tautomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Typically, the oil or fatty acid is nonvolatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Compounds of the present technology may be administered to the lungs by inhalation through the nose or mouth. Suitable pharmaceutical formulations for inhalation include solutions, sprays, dry powders, or aerosols containing any appropriate solvents and optionally other compounds such as, but not limited to, stabilizers, antimicrobial agents, antioxidants, pH modifiers, surfactants, bioavailability modifiers and combinations of these. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aqueous and nonaqueous (e.g., in a fluorocarbon propellant) aerosols are typically used for delivery of compounds of the present technology by inhalation.

Dosage forms for the topical (including buccal and sublingual) or transdermal administration of compounds of the present technology include powders, sprays, ointments, pastes, creams, lotions, gels, solutions, and patches. The active component may be mixed under sterile conditions with a pharmaceutically-acceptable carrier or excipient, and with any preservatives, or buffers, which may be required. Powders and sprays can be prepared, for example, with excipients such as lactose, talc, silicic acid, aluminum hydroxide, calcium silicates and polyamide powder, or mixtures of these substances. The ointments, pastes, creams and gels may also contain excipients such as animal and vegetable fats, oils, waxes, paraffins, starch, tragacanth, cellulose derivatives, polyethylene glycols, silicones, bentonites, silicic acid, talc and zinc oxide, or mixtures thereof. Absorption enhancers can also be used to increase the flux of the compounds of the present technology across the skin. The rate of such flux can be controlled by either providing a rate controlling membrane (e.g., as part of a transdermal patch) or dispersing the compound in a polymer matrix or gel.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference.

The formulations of the present technology may be designed to be short-acting, fast-releasing, long-acting, and sustained-releasing as described below. Thus, the pharmaceutical formulations may also be formulated for controlled release or for slow release.

The instant compositions may also include, for example, micelles or liposomes, or some other encapsulated form, or may be administered in an extended release form to provide a prolonged storage and/or delivery effect. Therefore, the pharmaceutical formulations and medicaments may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant present technology.

Various assays and model systems can be readily employed to determine the therapeutic effectiveness of the treatment according to the present technology.

For each of the indicated conditions described herein, test subjects will exhibit a 10%, 20%, 30%, 50% or greater reduction, up to a 75-90%, or 95% or greater, reduction, in one or more symptom(s) caused by, or associated with, the disorder in the subject, compared to placebo-treated or other suitable control subjects.

In an aspect, a method for inhibiting cell motility of a cancer cell is provided. The method includes contacting the cancer cell with a compound of any one of the above embodiments of compounds of Formulas I-IV (or a pharmaceutically acceptable salt thereof), thereby inhibiting the cell motility of the cancer cell. The method may include contacting the cell with an effective amount of any one of the above embodiments of compounds of Formulas I-IV (or a pharmaceutically acceptable salt thereof). In the method, the effective amount may include an amount effective in reducing cell motility of the cancer cell, e.g., as compared to cell motility of the cancer cell in the absence of the compound of the present technology and/or other motility-reducing compounds. For instance, the effective amount may include an amount effective in reducing cell motility of the cancer cell by at least about 50%, at least about 60%, at least about 70%, at least about 80%, at least about 90%, or at least about 95% as compared to cell motility of the cancer cell in the absence of the compound of the present technology and/or other motility-reducing compounds. The method may include inhibiting metastasis of the cancer cell. In any embodiment herein, the cancer cell may include a non-small cell lung cancer cell, a bladder cancer cell, a colon cancer, or a colon adenocarcinoma cell. The contacting may or may not be within a patient and/or on a patient. For example, the contacting may occur in vitro. In any of the embodiments of the method, the contacting step may include administration of a pharmaceutical composition, where the pharmaceutical composition includes an effective amount of any one of the embodiments of the compounds of Formulas I-IV (or a pharmaceutically acceptable salt thereof) and a pharmaceutically acceptable carrier. The effective amount may be from about 0.01 µg to about 1 mg of the compound per gram of the composition, and preferably from about 0.1 µg to about 500 µg of the compound per gram of the composition.

In an aspect, a method of treating a subject suffering from non-small cell lung cancer, bladder cancer, colon cancer, and/or colon adenocarcinoma is provided, the method including administration of a compound of any one or more of the herein-disclosed embodiments of the present technology to the subject. The method may include administration of an effective amount of any one of the embodiments of the compounds of Formulas I-IV (or a pharmaceutically acceptable salt thereof). In the method, administration of the compound (e.g., an effective amount of the compound) of any one of the above embodiments of the present technology to the patient or animal treats the patient or animal suffering from the non-small cell lung cancer, bladder cancer, colon cancer, and/or colon adenocarcinoma. In any embodiment of the method, it may be that administration of the compound of any one of the above embodiments of the present technology treats the subject suffering from the non-small cell lung cancer, bladder cancer, colon cancer, and/or colon adenocarcinoma.

In any of the embodiments of the method of treating the subject suffering from non-small cell lung cancer, bladder cancer, colon cancer, and/or colon adenocarcinoma, the method may include administration of a pharmaceutical composition, where the pharmaceutical composition includes an effective amount of any one of the embodiments of the compounds of the present technology or a pharmaceutically acceptable salt thereof and a pharmaceutically acceptable carrier. The effective amount may be from about 0.01 µg to about 1 mg of the compound per gram of the composition, and preferably from about 0.1 µg to about 500 µg of the compound per gram of the composition. In any of the embodiments of the method, the compound or composition may be administered orally, parenterally, rectally, or transdermally.

In any aspect and embodiment disclosed herein, the compound of the present technology may exhibit a selectivity ratio for Hsp90β over Hsp90α of at least about 2:1, such as at least about 4:1, at least about 10:1, at least about 20:1, at least about 30:1, at least about 50:1, at least about 70:1. The selectivity ratio therefore may be about 2:1, about 4:1, about 10:1, about 20:1, about 30:1, about 50:1, about 70:1, about 80:1, about 90:1, about 100:1, or any range including and/or in between any two of these values, or any range greater than any one of these values.

The examples herein are provided to illustrate advantages of the present technology and to further assist a person of ordinary skill in the art with preparing or using the compounds of the present technology or salts, pharmaceutical compositions, derivatives, prodrugs, racemic mixtures, or tautomeric forms thereof. The examples herein are also presented in order to more fully illustrate the preferred aspects of the present technology. The examples should in no way be construed as limiting the scope of the present technology, as defined by the appended claims. The examples can include or incorporate any of the variations, aspects or aspects of the present technology described above. The variations, aspects or aspects described above

19 may also further each include or incorporate the variations of any or all other variations, aspects or aspects of the present technology.

EXAMPLES

General Experimental Methods.

$^1$H NMR were recorded at 400 or 500 MHz (Bruker DRX-400) spectrometer and $^{13}$C NMR spectra were recorded at 125 MHz (Bruker DRX 500 with broadband, inverse triple resonance, and high resolution magic angle spinning, HR-MA probe spectrometer); chemical shifts are reported in δ (ppm) relative to the internal chloroform-d (CDCl$_3$, 7.27 ppm). FAB (HRMS) spectra were recorded with a LCT Premier (Waters Corp., Milford, Mass.). Concentration of solutions after reactions and extractions involved the use of a rotary evaporator operating at reduced pressure. The purity of all compounds was determined to be >95% purity as determined by $^1$H NMR and $^{13}$C NMR spectra, unless otherwise noted. TLC was performed on glass backed silica gel plates (Uniplate) with spots visualized by UV light. All solvents were reagent grade.

Preparation of Compound (1)

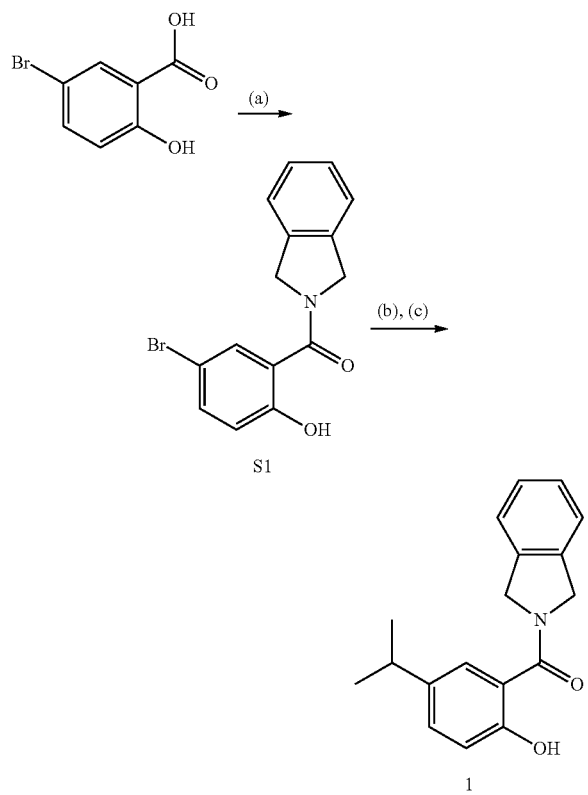

Reagents: (a) isoindoline hydrochloride, EDCI, HOBt, N,N-diisopropylethylamine;
(b) potassium isopropenyltrifluoroborate, Pd(PPh$_3$), Cs$_2$CO$_3$;
(c) Pd/C—H$_2$ (5-Bromo-2-hydroxyphenyl)(isoindolin-2-yl)methanone (S1):[4-5]

1-Ethyl-3-(3-dimethylaminopropyl)carbodiimide (5.20 g, 27.64 mmol, 2 eq.) was added to a stirred solution of 83 (3.0 g, 13.82 mmol, 1 eq.), isoindoline hydrochloride (3.22 g, 20.73 mmol, 1.5 eq.), 1-hydroxybenzotriazole (3.73 g, 27.64

20 mmol, 2 eq.) N,N-diisopropylethylamine (4.81 mL, 27.64 mmol, 2 eq.) in dichloromethane (150 mL) at 0° C. The resulting solution was stirred at rt for 14 h before quenching with saturated sodium bicarbonate solution (120 mL). The organic layer was washed with 1 M hydrochloric acid solution (120 mL) and saturated sodium chloride solution (120 mL), dried over sodium sulfate, filtered, and concentrated. The residue was purified by flash chromatography (SiO$_2$, 1:4 hexanes/ethyl acetate) to afford 84 (3.24 g, 77.9%) as a white amorphous solid. $^1$H NMR (400 MHz, CDCl$_3$) δ 10.92 (s, 1H), 7.73 (d, J=2.2 Hz, 1H), 7.48 (dd, J=8.8, 2.4 Hz, 1H), 7.34 (s, 4H), 6.94 (d, J=8.8 Hz, 1H), 5.10 (s, 4H). $^{13}$C NMR (100 MHz, CDCl$_3$) δ 169.4, 159.4, 136.1 (2), 134.8, 130.5, 128.2 (2), 122.8 (2), 120.2, 118.7 110.2, 55.8, 53.3. HRMS (ESI+) m/z [M+H$^+$] calcd for C$_{15}$H$_{13}$BrNO$_2$, 318.0130, found 318.0119.

2-Hydroxy-5-isopropylphenyl)(isoindolin-2-yl)methanone (1)

A vial was charged with 5-bromo-2-hydroxybenzoic acid (1.0 g, 3.42 mmol, 1 eq.), triethylamine (0.62 mL, 4.44 mmol, 1.3 eq.), [1,1' Bis(diphenylphosphino)ferrocene]dichloropalladium(II) (278 mg, 0.34 mmol, 0.1 eq.), potassium isopropenyltrifluoroborate (604 mg, 4.10 mmol, 1.2 eq.). The tube was sealed with a cap lined with a disposable Teflon septum. The tube was evacuated and purged with nitrogen (3 times), before the addition of 2-propanol (17 mL) by syringe. The resulting mixture was heated at 100° C. for 6 h, cooled to rt, and filtered through a small pad of celite (elution with ethyl acetate). Solvent was removed and the residue purified by flash chromatography (SiO$_2$, 1:4 ethyl acetate/hexanes) to afford (2-hydroxy-5-(prop-1-en-2-yl) phenyl)(isoindolin-2-yl)methanone, which was used further as obtained. Palladium on carbon (10%) was added to a solution of (2-hydroxy-5-(prop-1-en-2-yl)phenyl)(isoindolin-2-yl)methanone in ethyl acetate (25 mL). The suspension was stirred for 16 h under a hydrogen atmosphere before it was filtered through a pad of celite and eluted with EtOAc (20 mL). The eluent was concentrated to afford 1 (652 mg, 67.5%) as a white amorphous solid. $^1$H NMR (400 MHz, CDCl$_3$) δ 10.44 (s, 1H), 7.40 (d, J=2.2 Hz, 1H), 7.28 (s, 4H), 6.92 (d, J=8.5 Hz, 1H), 5.06 (s, 4H), 2.88 (hept, J=7.0 Hz, 1H), 1.24 (d, J=6.9 Hz, 6H). $^{13}$C NMR (100 MHz, CDCl$_3$) δ 171.4, 157.9, 138.8, 136.1 (2), 131.5, 128.0 (2), 125.7, 122.8 (2), 118.0, 117.1, 55.8, 53.5, 33.6, 24.4 (2). HRMS (ESI+) m/z [M+H$^+$] calcd for C$_{18}$H$_{20}$NO$_2$, 282.1494, found 282.1483.

Preparation of Compounds KUNB8 and KUNB30

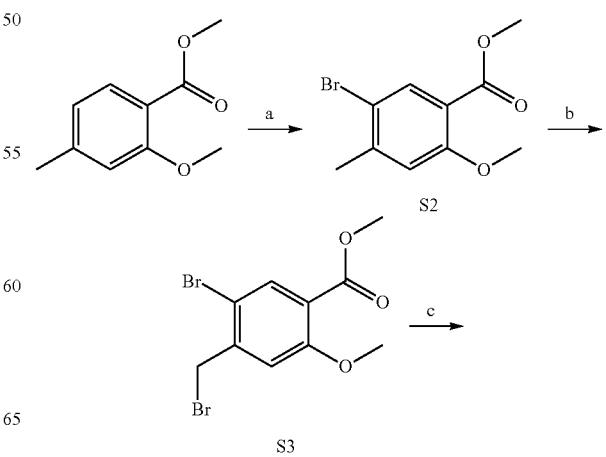

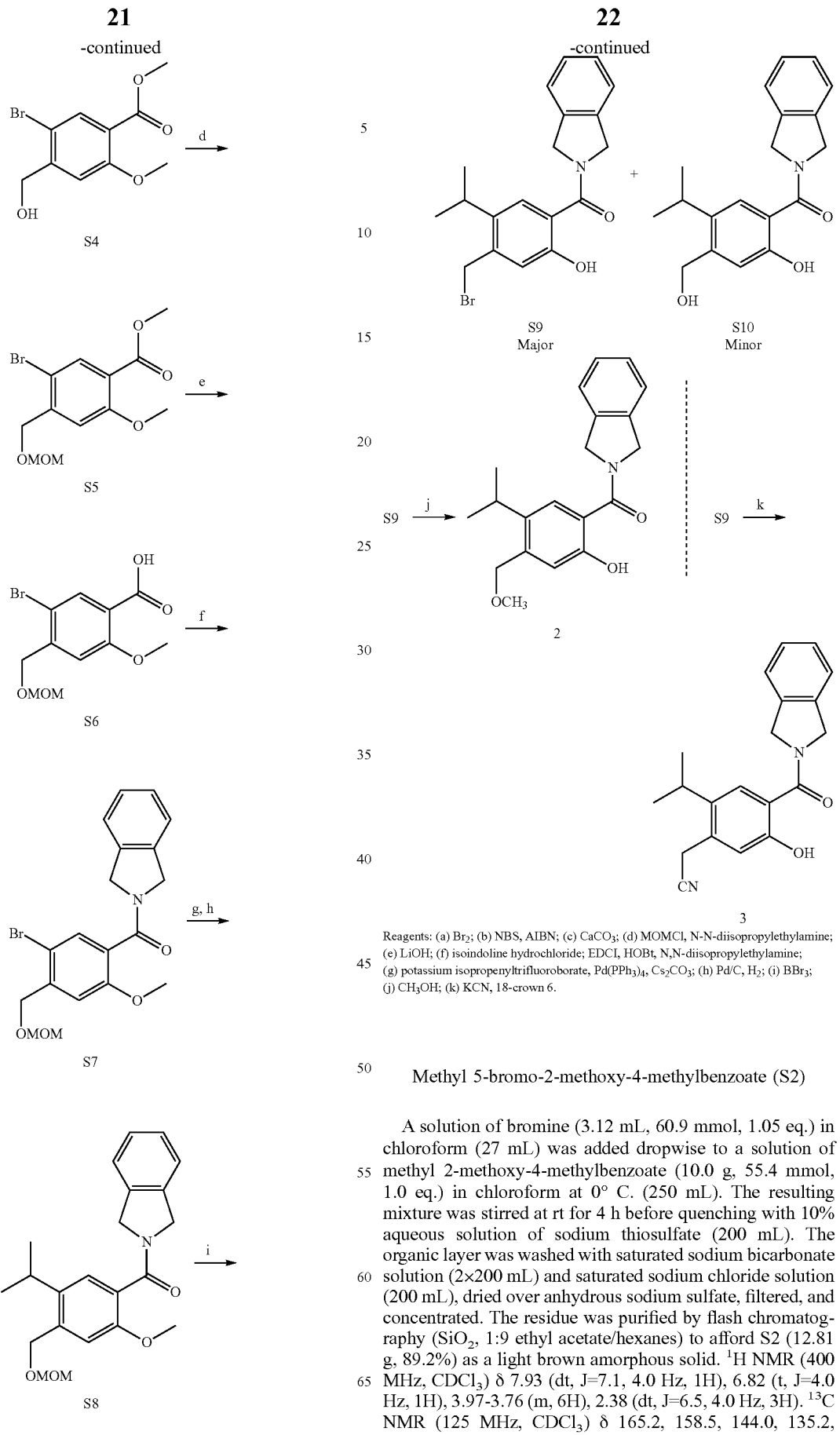

Reagents: (a) Br₂; (b) NBS, AIBN; (c) CaCO₃; (d) MOMCl, N-N-diisopropylethylamine; (e) LiOH; (f) isoindoline hydrochloride; EDCI, HOBt, N,N-diisopropylethylamine; (g) potassium isopropenyltrifluoroborate, Pd(PPh₃)₄, Cs₂CO₃; (h) Pd/C, H₂; (i) BBr₃; (j) CH₃OH; (k) KCN, 18-crown 6.

Methyl 5-bromo-2-methoxy-4-methylbenzoate (S2)

A solution of bromine (3.12 mL, 60.9 mmol, 1.05 eq.) in chloroform (27 mL) was added dropwise to a solution of methyl 2-methoxy-4-methylbenzoate (10.0 g, 55.4 mmol, 1.0 eq.) in chloroform at 0° C. (250 mL). The resulting mixture was stirred at rt for 4 h before quenching with 10% aqueous solution of sodium thiosulfate (200 mL). The organic layer was washed with saturated sodium bicarbonate solution (2×200 mL) and saturated sodium chloride solution (200 mL), dried over anhydrous sodium sulfate, filtered, and concentrated. The residue was purified by flash chromatography (SiO₂, 1:9 ethyl acetate/hexanes) to afford S2 (12.81 g, 89.2%) as a light brown amorphous solid. $^1$H NMR (400 MHz, CDCl₃) δ 7.93 (dt, J=7.1, 4.0 Hz, 1H), 6.82 (t, J=4.0 Hz, 1H), 3.97-3.76 (m, 6H), 2.38 (dt, J=6.5, 4.0 Hz, 3H). $^{13}$C NMR (125 MHz, CDCl₃) δ 165.2, 158.5, 144.0, 135.2, 118.9, 114.8, 114.6, 56.3, 52.2, 23.7. HRMS (ESI+) m/z [M+H$^+$] calcd for $C_{10}H_{12}BrO_3$, 258.9969, found 258.9973.

Methyl 5-bromo-4-(bromomethyl)-2-methoxybenzoate (S3)

A solution of S2 (12.8 g, 48.8 mmol), N-bromosuccinimide (9.68 g, 54.78 mmol, 1.1 eq.), azobisisobutyronitrile (1.64 g, 9.96 mmol, 0.2 eq.) in carbon tetrachloride was heated at 70° C. After 14 h, solvent was removed and the residue purified by flash chromatography (SiO$_2$, 1:9 ethyl acetate/hexanes) to afford S3 (13.92 g, 71.3%) as a white amorphous solid. $^1$H NMR (500 MHz, CDCl$_3$) δ 7.91 (s, 1H), 7.60 (s, 1H), 7.00 (s, 1H), 3.99 (s, 3H), 3.90 (s, 3H). $^{13}$C NMR (125 MHz, CDCl$_3$) δ 164.7, 159.0, 144.8, 135.5, 123.0, 114.6, 109.5, 56.7, 52.7, 39.3. HRMS (ESI+) m/z [M+H$^+$] calcd for $C_{10}H_{11}Br_2O_3$, 336.9075, found 336.9079.

Methyl 5-bromo-4-(hydroxymethyl)-2-methoxybenzoate (S4):[6]

Calcium carbonate (11.3 g, 113.4 mmol, 3 eq.) was added to a solution of S3 (12.8 g, 37.8 mmol, 1 eq.) in dioxane (100 mL) and water (100 mL). The resulting mixture was heated at 120° C. in a sealed tube for 16 h. The reaction mixture was cooled to rt, filtered, and concentrated. The residue was purified by flash chromatography (SiO$_2$, 1:5 ethyl acetate/hexanes) to afford S4 (8.2 g, 79.2%) as a colorless amorphous solid. $^1$H NMR (500 MHz, CDCl$_3$) δ 7.9 (s, 1H), 7.2 (d, J=0.9 Hz, 1H), 4.7 (dd, J=5.7, 1.0 Hz, 2H), 3.9 (s, 3H), 3.9 (s, 3H). $^{13}$C NMR (125 MHz, CDCl$_3$) δ 165.5, 159.0, 145.7, 135.3, 120.0, 111.9, 111.3, 64.8, 56.5, 52.5. HRMS (ESI+) m/z [M+H$^+$] calcd for $C_{10}H_{12}BrO_4$, 274.9919, found 274.9923.

Methyl 5-bromo-2-methoxy-4-((methoxymethoxy)methyl)benzoate (S5)

A solution of S4 (3.2 g, 11.63 mmol, 1.0 eq.) in dichloromethane (116 mL) was cooled to 0° C. before the addition of N,N-diisopropylethylamine (12.13 mL, 69.79 mmol, 6.0 eq.) and 6M solution of chloromethoxymethyl ether (11.8 ml, 69.79 mmol, 6.0 eq.). The reaction was allowed to reach at rt and stirred for 14 h before quenching with saturated sodium bicarbonate solution (60 mL). The aqueous layer was extracted with dichloromethane (2×60 mL) and the combined organic layers were washed with saturated sodium chloride solution (150 ml), dried over anhydrous sodium sulfate, filtered, and concentrated. The residue was purified by flash chromatography (SiO$_2$, 1:49 acetone/dichloromethane) to afford S5 (2.82 g, 76.1%) as a colorless oil. $^1$H NMR (400 MHz, CDCl$_3$) δ 7.97 (s, 1H), 7.18 (d, J=0.9 Hz, 1H), 4.80 (s, 2H), 4.64 (d, J=0.9 Hz, 2H), 3.93 (s, 3H), 3.89 (s, 3H), 3.44 (s, 3H). $^{13}$C NMR (100 MHz, CDCl$_3$) δ 165.4, 158.9, 143.4, 135.4, 120.3, 112.4, 111.8, 96.6, 68.9, 56.6, 55.9, 52.4. HRMS (ESI+) m/z [M+H$^+$] calcd for $C_{12}H_{16}BrO_5$, 319.0181, found 319.0187.

5-Bromo-2-methoxy-4-((methoxymethoxy)methyl)benzoic acid (S6)

Lithium hydroxide monohydrate (5.37 g, 128.0 mmol, 10.0 eq.) was added to a solution of S5 (4.08 g, 12.8 mmol, 1 eq.) in a solvent mixture of tetrahydrofuran (43 mL), water (43 mL), methanol (43 mL). The resulting mixture was stirred at rt for 16 h and concentrated. The residue was treated with 1 M hydrochloric acid and pH was adjusted to 2. The resulting suspension was extracted with ethyl acetate (3×100 mL), the combined organic layers were washed with saturated sodium chloride solution, dried over anhydrous sodium sulfate, filtered and concentrated to afford S6 (3.26 g, 83.2%) as a light brown solid. $^1$H NMR (500 MHz, CDCl$_3$) δ 10.59 (s, 1H), 8.33 (s, 1H), 7.30 (s, 1H), 4.83 (s, 2H), 4.67 (d, J=0.9 Hz, 2H), 4.12 (s, 3H), 3.46 (s, 3H). $^{13}$C NMR (125 MHz, CDCl$_3$) δ 164.1, 157.5, 145.5, 137.1, 117.8, 113.9, 111.6, 96.7, 68.7, 57.3, 56.0. HRMS (ESI+) m/z [M+H$^+$] calcd for $C_{11}H_{14}BrO_5$, 305.0025, found 305.0028.

(5-Bromo-2-methoxy-4-((methoxymethoxy)methyl)phenyl)(isoindolin-2-yl)methanone (S7)

1-Ethyl-3-(3-dimethylaminopropyl)carbodiimide (1.25 g, 6.54 mmol, 2.0 eq.) was added to a stirred solution of S6 (1.0 g, 3.27 mmol, 1 eq.), isoindoline hydrochloride (663 mg, 4.26 mmol, 1.3 eq.), 1-hydroxybenzotriazole (1.0 g, 6.54 mmol, 2 eq.) N-,N-diisopropylethylamine (1.72 mL, 9.81 mmol, 3.0 eq.) in dichloromethane (33 mL) at 0° C. The resulting solution was stirred at rt for 14 h before quenching with saturated sodium bicarbonate solution (30 mL). The organic layer was washed with 1 M hydrochloric acid solution (30 mL) and saturated sodium chloride solution (30 mL), dried over sodium sulfate, filtered and concentrated. The residue residue was purified by flash chromatography (SiO$_2$, 1:3 hexanes/ethylacetate) to afford S7 (1.22 g, 91.8%) as a colorless oil. $^1$H NMR (400 MHz, CDCl$_3$) δ 7.50 (s, 1H), 7.37-7.26 (m, 3H), 7.19-7.12 (m, 2H), 4.99 (s, 2H), 4.82 (s, 2H), 4.68 (s, 2H), 4.62 (s, 2H), 3.88 (s, 3H), 3.48 (s, 3H). HRMS (ESI+) m/z [M+H$^+$] calcd for $C_{11}H_{14}BrO_5$, 452.1072, found 452.1066.

Isoindolin-2-yl(5-isopropyl-2-methoxy-4-((methoxymethoxy)methyl)phenyl)methanone (S8)

A biotage microwave vial was charged with S7 (1.0 g, 2.46 mmol, 1 eq.), Tetrakis(triphenylphosphine)palladium (0) (277 mg, 0.24 mmol, 0.1 eq.), cesium carbonate (2.4 g, 7.4 mmol, 3 eq.), and potassium isopropenyltrifluoroborate (427 mg, 2.88 mmol, 1.2 eq.). The tube was sealed with a cap lined with a disposable Teflon septum. The tube was evacuated and purged with nitrogen (3 times), before the addition of tetrahydrofuran (10.8 mL) and water (1.2 mL) by syringe. The resulting mixture was heated at 100° C. for 24 h, cooled to rt, and filtered through a small pad of celite (elution with ethyl acetate). Solvent was removed and the residue purified by flash chromatography (SiO$_2$, 1:3 ethyl acetate/hexanes) to afford isoindolin-2-yl(2-methoxy-4-((methoxymethoxy)methyl)-5-(prop-1-en-2-yl)phenyl) methanone, which was used further as obtained. Palladium on carbon (10%) was added to a solution of isoindolin-2-yl(2-methoxy-4-((methoxymethoxy)methyl)-5-(prop-1-en-2-yl)phenyl)methanone in ethyl acetate (25 mL). The suspension was stirred for 16 h under a hydrogen atmosphere before it was filtered through a pad of celite and eluted with EtOAc (20 mL). The eluent was concentrated to afford S8 (530 mg, 58.3%) as a light brown amorphous solid. $^1$H NMR (400 MHz, CDCl$_3$) δ 7.76 (d, J=7.6 Hz, 1H), 7.60 (td, J=7.6, 1.1 Hz, 1H), 7.48 (d, J=7.7 Hz, 1H), 7.41 (t, J=7.5 Hz, 1H), 7.21 (s, 1H), 6.94 (s, 1H), 4.94 (s, 2H), 4.67 (s, 2H), 4.63 (s, 2H), 3.70 (s, 3H), 3.37 (s, 3H), 3.05 (h, J=6.8 Hz, 1H), 1.15 (s, 3H). $^{13}$C NMR (100 MHz, CDCl$_3$) δ 168.7, 166.3, 155.0, 141.6, 139.0, 138.4, 134.1, 131.6, 128.7, 125.7, 125.4, 125.2, 123.7, 111.2, 96.0, 66.8, 56.1, 55.7, 48.7, 28.4, 24.0 (2). HRMS (ESI+) m/z [M+Na$^+$] calcd for $C_{22}H_{27}NO_4Na$, 392.1838, found 392.1838.

(4-(Bromomethyl)-2-hydroxy-5-isopropylphenyl) (isoindolin-2-yl)methanone (S9)

1 M solution of boron tribromide (1.22 mmol, 1.22 mL, 2 eq.), was added to a solution of 92 (200 mg, 0.61 mmol) in anhydrous dichloromethane (6.1 ml) at 0° C. The resulting mixture was stirred at rt for 14 h before quenching with saturate sodium bicarbonate solution (5 mL). The aqueous layer was extracted with dichloromethane (2×10 mL). The combined organic layers were washed with saturated sodium chloride solution (20 mL), dried over anhydrous sodium sulfate, filtered, and concentrated. The residue was purified by flash chromatography (SiO$_2$, 1:50 acetone/dichloromethane) to afford S9 (98 mg, 43.7%) as a white solid. Additionally, compound S10 (38 mg, 20%) was also isolated. $^1$H NMR (500 MHz, CD$_2$Cl$_2$) δ 7.53 (s, 1H), 7.32 (s, 4H), 6.94 (s, 1H), 5.07 (s, 5H), 4.53 (s, 2H), 3.27 (p, J=6.8 Hz, 1H), 1.31 (d, J=6.8 Hz, 5H). $^{13}$C NMR (125 MHz, CD$_2$Cl$_2$) δ 170.5, 157.3, 139.9 (2), 138.1 (2), 128.1, 126.3, 123.0, 119.4 (2), 119.1 (2), 118.5, 55.9 (2), 31.0, 24.3 (2). HRMS (ESI+) m/z [M+Na$^+$] calcd for $C_{19}H_{20}BrNO_2Na$, 374.756, found 374.0769.

(2-Hydroxy-4-(hydroxymethyl)-5-isopropylphenyl) (isoindolin-2-yl)methanone (S10)

Obtained as a colorless solid (38 mg, 20%). $^1$H NMR (400 MHz, CDCl$_3$) δ 10.53 (s, 1H), 7.53 (s, 1H), 7.32 (s, 4H), 7.07 (s, 1H), 5.10 (s, 4H), 4.76 (s, 2H), 3.17-3.22 (m, 1H), 1.26-1.30 (m, 6H). $^{13}$C NMR (125 MHz, CDCl$_3$) δ 171.0, 158.0, 150.2, 143.1, 136.7, 136.4, 129.9, 129.1, 126.8, 126.6, 125.2, 116.9, 116.6, 62.9, 55.8, 53.4, 30.2, 24.5 (2). HRMS (ESI+) m/z [M+H$^+$] calcd for $C_{19}H_{22}NO_3$, 312.1600, found 312.1604.

2-(5-Hydroxy-4-(isoindoline-2-carbonyl)-2-isopropylphenyl)acetonitrile (2; KUNB8)

Potassium cyanide (43 mg, 0.66 mmol, 5.0 eq.) was added to a solution of S9 (50 mg, 0.14 mmol, 1.0 eq.) and 18-crown-6 (71 mg, 0.27 mmol, 2.0 eq.) in N,N-dimethylformamide (2.0 mL) at rt. The reaction was stirred for 2 h, diluted with water (20 mL), extracted with ethyl acetate (2×20 mL). The combined organic layers were washed with saturated sodium chloride solution (30 mL), dried over anhydrous sodium sulfate, filtered, and concentrated. The residue was purified by flash chromatography (SiO$_2$, 1:3 ethyl acetate/hexanes) to afford 2 (KUNB8) (39.9 mg, 92.5%) as colorless oil. $^1$H NMR (400 MHz, CDCl$_3$) δ 10.53 (s, 1H), 7.54 (s, 1H), 7.32 (d, J=4.6 Hz, 4H), 7.03 (s, 1H), 5.09 (s, 4H), 3.74 (s, 2H), 3.07 (hept, J=6.9 Hz, 1H), 1.32 (d, J=6.8 Hz, 6H). $^{13}$C NMR (100 MHz, CDCl$_3$) δ 170.5, 158.0, 136.5, 135.85 (2) 132.4, 128.1, 125.7 (2), 122.8, 118.6, 117.7, 117.5, 56.2 (2), 29.0, 24.1 (2), 21.7. HRMS (ESI+) m/z [M+H$^+$] calcd for $C_{20}H_{21}N_2O_2$, 321.1603, found 321.1610.

(2-Hydroxy-5-isopropyl-4-(methoxymethyl)phenyl) (isoindolin-2-yl)methanone (3: KUNB30)

Sodium methoxide (10.8 mg, 0.20 mmol, 2.5 eq.) was added to a solution of S9 (30 mg, 0.08 mmol, 1 eq.) in anhydrous methanol. The resulting mixture was heated at 60° C. for 8 h, before quenching with 1 M hydrochloric acid (2 mL), extracted with ethyl acetate (3×3 mL). The combined organic layers were washed with saturated sodium chloride solution, dried over sodium sulfate, filtered, and concentrated. The residue was purified by flash chromatography (SiO$_2$, 3:10 ethyl acetate/hexanes) to afford 3 (KUNB30) (13 mg, 49.9%) as a colorless oil. $^1$H NMR (400 MHz, CDCl$_3$) δ 10.45 (s, 1H), 7.52 (s, 1H), 7.29 (d, J=19.5 Hz, 4H), 7.02 (s, 1H), 5.09 (s, 4H), 4.50 (s, 2H), 3.43 (s, 3H), 3.14-3.46 (m, 1H), 1.28 (d, J=6.9 Hz, 7H). $^{13}$C NMR (100 MHz, CDCl$_3$) δ 170.8, 157.4, 140.4 (2), 137.0 (2), 127.8, 124.9 (2), 122.6, 117.8 (2), 116.6, 72.1, 58.3 (3), 28.0, 24.2 (2). HRMS (ESI+) m/z [M+Na$^+$] calcd for $C_{20}H_{23}NO_3Na$, 348.1576, found 346.1567.

Preparation of Compound KUNB13

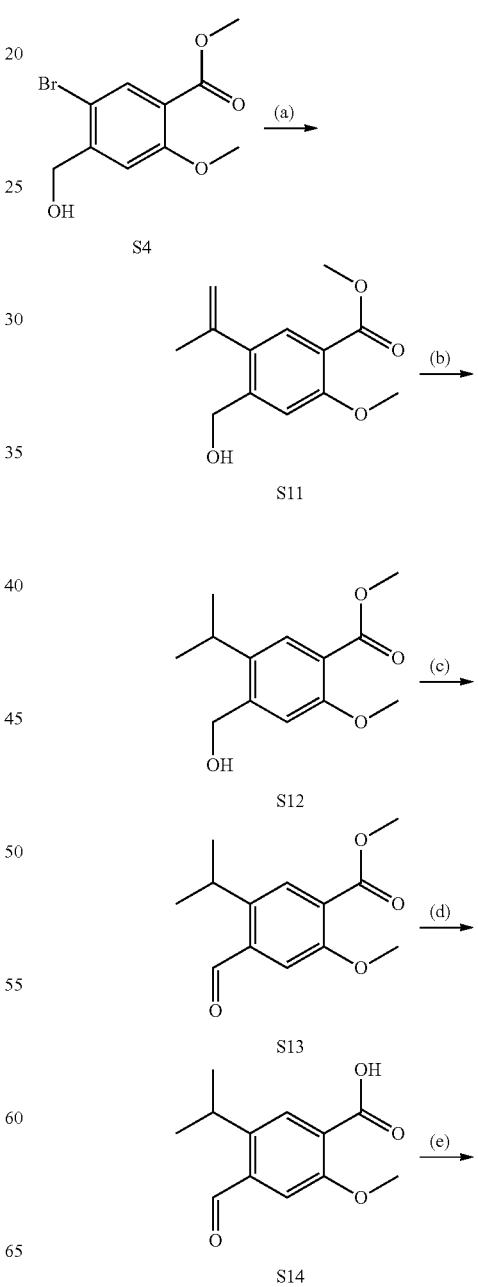

-continued

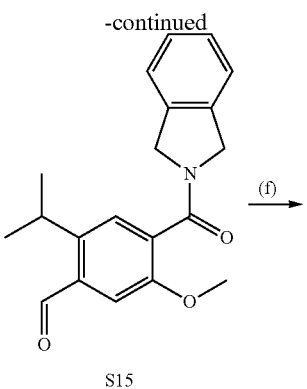

S15

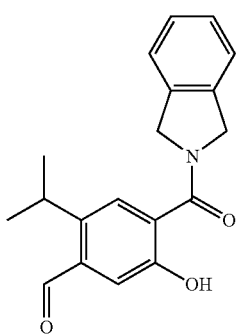

4

Reagents: (a) potassium isopropenyltrifluoroborate, Pd(PPh₃), Cs₂CO₃; (b) Pd/C—H₂; (c) MnO₂; (d) Bu₃SnOH; (e) isoindoline hydrochloride, EDCI, HOBt, N,N-diisopropylethylamine; (g) BBr₃

Methyl 4-formyl-2-methoxy-5-(prop-1-en-2-yl)benzoate (S11)

A biotage microwave vial was charged with S4 (0.75 g, 2.7 mmol, 1 eq.), tetrakis(triphenylphosphine)palladium(0) (312 mg, 0.27 mmol, 0.1 eq.), cesium carbonate (2.68 g, 8.25 mmol, 3 eq.), and potassium isopropenyltrifluoroborate (440 mg, 2.97 mmol, 1.2 eq.). The tube was sealed with a cap lined with a disposable teflon septum. The tube was evacuated and purged with nitrogen (3 times), before the addition of tetrahydrofuran (21.6 mL) and water (2.4 mL) by syringe. The resulting mixture was heated at 100° C. for 24 h, cooled to rt, and filtered through a small pad of celite (elution with ethyl acetate). Solvent was removed and the residue was purified by flash chromatography (SiO₂, 1:3 ethyl acetate/hexanes) to afford S11 as a colorless amorphous solid (580 mg, 90%). $^1$H NMR (400 MHz, CDCl₃) δ 7.57 (s, 1H), 7.14 (s, 1H), 5.19 (p, J=1.7 Hz, 1H), 4.82-4.76 (m, 1H), 4.69 (s, 2H), 3.84 (d, J=3.0 Hz, 6H), 2.72 (s, 1H), 2.06-1.94 (m, 3H). $^{13}$C NMR (100 MHz, CDCl₃) δ 166.7, 158.4, 144.0, 143.3, 134.2, 131.3, 118.1, 116.1, 110.9, 62.5, 56.1, 52.1, 24.8. HRMS (ESI+) m/z [M+H⁺] calcd for C₁₃H₁₇O₄, 237.1126, found 237.1122.

Methyl 4-(hydroxymethyl)-5-isopropyl-2-methoxybenzoate (S12)

Palladium on carbon (10%) was added to a solution of S11 (500 mg, 2.11 mmol) in ethyl acetate (6 mL). The suspension was stirred for 16 h under a hydrogen atmosphere before it was filtered through a pad of celite and eluted with EtOAc (20 mL). The eluent was concentrated to afford S12 (476 mg, 94.2%) as a colorless amorphous solid. $^1$H NMR (400 MHz, CDCl₃) δ 7.71 (s, 1H), 7.06 (s, 1H), 4.78 (s, 2H), 3.88 (s, 3H), 3.84 (s, 3H), 3.06 (hept, J=6.9 Hz, 1H), 1.22 (d, J=6.8 Hz, 6H). $^{13}$C NMR (100 MHz, CDCl₃) δ 167.1, 157.5, 143.7, 137.9, 128.9, 118.9, 111.1, 62.5, 56.3, 52.2, 28.0, 23.9 (2). HRMS (ESI+) m/z [M+Na⁺] calcd for C₁₃H₁₈O₄Na, 261.1103, found 261.1091.

Methyl 4-formyl-5-isopropyl-2-methoxybenzoate (S13)

Manganese dioxide (1.64 g, 18.8 mmol, 10.0 eq.) was added to a solution of S12 (450 mg, 1.88 mmol, 1.0 eq.) in dichloromethane at rt. The resulting mixture was stirred at rt for 16 h, filtered through a small pad of celite, eluted with ethyl acetate, and concentrated. The residue was purified by flash chromatography (SiO₂, 1:6 ethyl acetate/hexanes) to afford S13 (367.3 mg, 82.7%) as a yellow colorless solid. $^1$H NMR (400 MHz, CDCl₃) δ 10.44 (s, 1H), 7.77 (s, 1H), 7.40 (s, 1H), 3.91 (d, J=3.5 Hz, 6H), 3.84-3.75 (m, 1H), 1.30 (d, J=6.9 Hz, 6H). $^{13}$C NMR (100 MHz, CDCl₃) δ 190.9, 166.5, 156.8, 143.2, 136.1, 129.6, 125.6, 112.0, 56.4, 52.5, 27.2, 24.2 (2). HRMS (ESI+) m/z [M+H⁺] calcd for C₁₃H₁₇O₄, 237.1127, found 237.1117.

4-Formyl-5-isopropyl-2-methoxybenzoic acid (S14)

Trimethyltinhydroxide (3.63 g, 20.1 mmol, 4.0 eq.) was added to solution of S13 (1.12 g, 5.03 mmol, 1.0 eq.) in 1,2 dichloroethane (25 mL). The resulting mixture was heated at 75° C. for 50 h, cooled to rt, and concentrated. The residue was suspended in ethyl acetate (100 mL), washed with 1 M hydrochloric acid (3×60 mL) and saturated sodium chloride solution (100 mL). The solvent was removed to afford S14 (952 mg, 85.1%) as a colorless amorphous solid. $^1$H NMR (400 MHz, CDCl₃) δ 10.74 (br s, 1H), 10.52 (s, 1H), 8.27 (s, 1H), 7.53 (s, 1H), 4.13 (s, 3H), 3.79-4.13 (m, 1H), 1.36 (d, J=6.8 Hz, 6H). $^{13}$C NMR (100 MHz, CDCl₃) δ 190.4, 164.9, 156.2, 145.1, 137.5, 132.6, 122.3, 111.5, 57.3, 27.4, 24.3. HRMS (ESI-) m/z [M-H⁺] calcd for C₁₂H₁₃O₄, 221.0814, found 221.0809.

4-(Isoindoline-2-carbonyl)-2-isopropyl-5-methoxybenzaldehyde (S15)

1-Ethyl-3-(3-dimethylaminopropyl)carbodiimide (1.63 g, 8.54 mmol, 2.0 eq.) was added to a stirred solution of S14 (950 mg, 4.27 mmol, 1 eq.), isoindoline hydrochloride (731 mg, 4.70 mmol, 1.1 eq.), 1-hydroxybenzotriazole (635 mg, 4.70 mmol, 1.1 eq.) N-,N-diisopropylethylamine (3.26 mL, 18.8 mmol, 4.4 eq.) in dichloromethane 42 mL) at 0° C. The resulting solution was stirred at rt for 14 h before quenching with saturated sodium bicarbonate solution (30 mL). The organic layer was washed with 1 M hydrochloric acid solution (30 mL) and saturated sodium chloride solution (30 mL), dried over anhydrous sodium sulfate, filtered and concentrated. The residue was purified by flash chromatography (SiO₂, 3:10 hexanes/ethylacetate) to afford S15 (1.22 g, 91.8%) as a white amorphous solid. $^1$H NMR (400 MHz, CDCl₃) δ 10.47 (s, 1H), 7.48-7.21 (m, 5H), 7.15 (d, J=7.4 Hz, 1H), 5.01 (s, 2H), 4.58 (s, 2H), 4.02-3.76 (m, 4H), 1.32 (d, J=6.8 Hz, 7H). $^{13}$C NMR (100 MHz, CDCl₃) δ 190.8, 167.6, 153.7, 144.9, 136.4, 136.4, 134.4, 132.5, 128.0, 127.7, 126.1, 123.3, 122.7, 111.2, 56.1, 53.4, 52.3, 27.3, 24.4 (2). HRMS (ESI+) m/z [M+Na⁺] calcd for C₂₀H₂₁NO₃Na, 346.1419, found 346.1404.

5-Hydroxy-4-(isoindoline-2-carbonyl)-2-isopropyl-benzaldehyde (4: KUNB13)

1 M solution of boron tribromide (1.22 mmol, 1.22 mL, 2 eq.), was added to a solution of S15 (200 mg, 0.61 mmol) in anhydrous dichloromethane (6.1 ml) at 0° C. The resulting mixture was stirred at rt for 14 h before quenching with saturate sodium bicarbonate solution (5 mL). The aqueous layer was extracted with dichloromethane (2×10 mL). The combined organic layers were washed with saturated sodium chloride solution (20 mL), dried over sodium sulfate, filtered and concentrated. The residue was purified by flash chromatography ($SiO_2$, 1:50 acetone/dichloromethane) to afford 4 (KUNB13) (121.8 mg, 63.7%) as a colorless solid. $^1$H NMR (400 MHz, $CDCl_3$) δ 10.31 (s, 1H), 10.11 (s, 1H), 7.64 (s, 1H), 7.43 (s, 1H), 7.37-7.29 (m, 4H), 5.08 (s, 5H), 3.93 (h, J=6.9 Hz, 1H), 1.34 (d, J=6.7 Hz, 6H). HRMS (ESI−) m/z [M−H$^+$] calcd for $C_{19}H_{18}NO_3$, 308.1287, found 308.1282.

Preparation of KUNB14

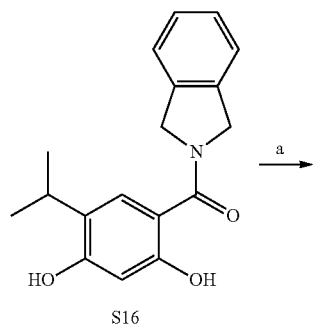

S16

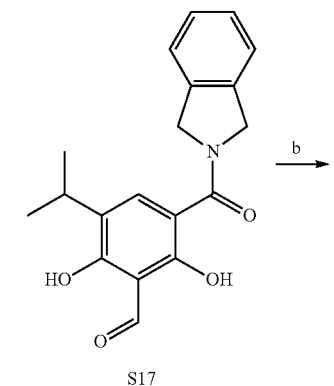

S17       5

Reagents: (a) TFA, HMTA, 100° C.; (b) NaBH$_4$

2,6-Dihydroxy-3-(isoindoline-2-carbonyl)-5-isopropylbenzaldehyde (S17)

S16 was prepared following a literature procedure. A solution of S16 (400 mg, 1.34 mmol, 1 eq.), hexamethylenetetramine (376 mg, 2.68 mmol, 2.0 eq.) in trifluoroacetic acid was heated at 100° C. for 14 h in a sealed tube, cooled to rt, and solvent was removed. The residue was treated with 3 M hydrochloric acid and the resulting mixture was heated at 60° C. for 3 h. The mixture was cooled to rt, diluted with water (20 ml), extracted with ethyl acetate (2×20 mL). The organic layer was washed with water (30 ml), saturated sodium bicarbonate solution (30 mL), and saturated sodium chloride solution (30 mL), dried over anhydrous sodium sulfate, filtered, and concentrated. The residue was purified by flash chromatography ($SiO_2$, 1:9 ethyl acetate/hexanes) to afford S17 (312.2 mg, 71.8%) as a pale yellow amorphous solid. $^1$H NMR (500 MHz, $CDCl_3$) δ 13.06 (s, 1H), 12.74 (s, 1H), 10.44 (s, 1H), 7.74 (s, 1H), 7.34 (d, J=2.2 Hz, 4H), 5.12 (s, 4H), 3.36-3.27 (m, 1H), 1.28 (d, J=6.9 Hz, 6H). $^{13}$C NMR (125 MHz, $CDCl_3$) δ 195.1, 170.7, 165.0, 164.0, 135.7, 133.5 (2), 128.2 (2), 126.2, 122.8 (2), 110.1, 106.9, 54.8 (2), 26.1, 22.7 (2). HRMS (ESI+) m/z [M+H$^+$] calcd for $C_{19}H_{20}NO_4$, 338.2120, found 338.2117.

(2,4-Dihydroxy-3-(hydroxymethyl)-5-isopropylphenyl)(isoindolin-2-yl)methanone (5; KUNB14)

Sodium borohydride (2.8 mg, 0.06 mmol) was added to a solution of S17 (20 mg, 0.07 mmol, 2.0 eq.) in a solvent mixture of tetrahydrofuran (1.5 mL) and methanol (0.5 mL) at ° C. The resulting mixture was stirred at rt for 1 h before the addition of 1 M hydrochloric acid (2 mL). The aqueous layer was extracted with ethyl acetate (2×5 mL), and the combined organic layers washed with saturated sodium chloride solution, dried over anhydrous sodium sulfate, filtered, and concentrated. The residue was purified by preparatory TLC ($SiO_2$, 1:3 ethyl acetate/hexanes) to give 5 (KUNB14) as a colorless amorphous solid (14.2 mg, 72.2%). $^1$H NMR (500 MHz, $CDCl_3$) δ 11.72 (s, 1H), 8.76 (s, 1H), 7.43 (s, 1H), 7.32 (s, 4H), 5.11 (s, 6H), 3.34-3.24 (m, 1H), 2.31 (s, 1H), 1.28 (d, J=6.9 Hz, 6H). $^{13}$C NMR (125 MHz, $CDCl_3$) δ 171.7, 158.6, 157.1, 136.2 (2), 128.0, 126.3 (2), 125.5, 122.8 (2), 111.4, 108.3, 59.3, 54.2 (2), 26.6, 23.1 (2). HRMS (ESI+) m/z [M+H$^+$] calcd for $C_{19}H_{22}NO_4$, 328.1549, found 328.1543.

Preparation of Compound (KUNB31a)

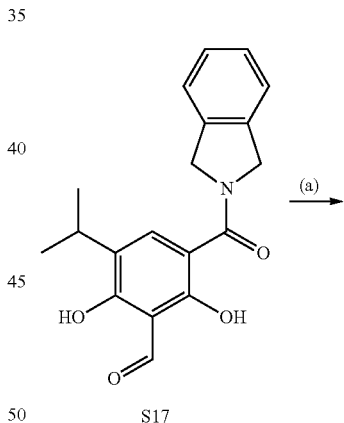

S17

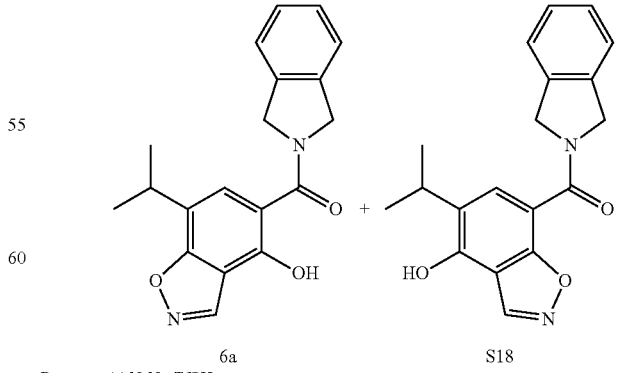

6a     S18

Reagents: (a) NaN$_3$, TfOH

(4-Hydroxy-7-isopropylbenzo[d]isoxazol-5-yl)(isoindolin-2-yl)methanone (6a: KUNB31a)

[7]Triflic acid (79 μL, 0.90 mmol, 6.0 eq.) and sodium azide (15 mg, 0.23 mmol, 1.5 eq.) were added to a solution of S17 (50 mg, 0.15 mmol, 1.0 eq.) in acetonitrile (1.5 mL) at rt. The resulting mixture was stirred for 5 min and concentrated. The residue was treated with water (2 mL) and ethyl acetate (3 mL). The aqueous layer was extracted with ethyl acetate (2×3 mL) and the combined organic layers washed with saturated sodium chloride solution (6 mL), dried over anhydrous sodium sulfate, filtered, and concentrated. The residue was purified using preparatory TLC (SiO$_2$, 1:3 ethyl acetate/hexanes) to afford 6a (KUNB31a) (18.3 mg, 37.8%) and S18 (13.1, 27.1%). $^1$H NMR (400 MHz, CDCl$_3$) δ 12.42 (s, 1H), 8.86 (d, J=1.3 Hz, 1H), 7.65 (s, 1H), 7.34 (s, 4H), 5.14 (s, 4H), 3.40 (hept, J=7.0 Hz, 1H), 1.45 (d, J=7.1 Hz, 6H). $^{13}$C NMR (100 MHz, CDCl$_3$) δ 171.1, 163.7, 156.1, 145.2, 135.9, 128.2 (2), 126.5 (2), 122.8 (2), 121.6, 112.9, 110.4, 54.2 (2), 29.4, 22.7 (2). HRMS (ESI+) m/z [M+H$^+$] calc. for C$_{19}$H$_{19}$N$_2$O$_3$, 323.1396, found 323.1392.

(4-Hydroxy-5-isopropylbenzo[d]isoxazol-7-yl)(isoindolin-2-yl)methanone (S18)

$^1$H NMR (400 MHz, CDCl$_3$; δ 9.59 (s, 1H), 9.10 (s, 1H), 7.60 (s, 1H), 7.45-7.26 (m, 3H), 7.16 (d, J=7.4 Hz, 1H), 5.17 (s, 2H), 4.91 (s, 2H), 3.18 (h, J=7.0 Hz, 1H), 1.06 (d, J=6.9 Hz, 6H). $^{13}$C NMR (101 MHz, CDCl$_3$) δ 167.9, 157.9, 151.0, 145.2, 136.5, 135.8, 130.0, 129.4, 128.1, 127.9, 123.1, 122.8, 112.6, 109.5, 53.9, 53.3, 26.4, 22.9 (2). HRMS (ESI+) m/z [M+H$^+$] calc. for C$_{19}$H$_{19}$N$_2$O$_3$, 323.1396, found 323.1399.

Preparation of Compound (KUNB31b)

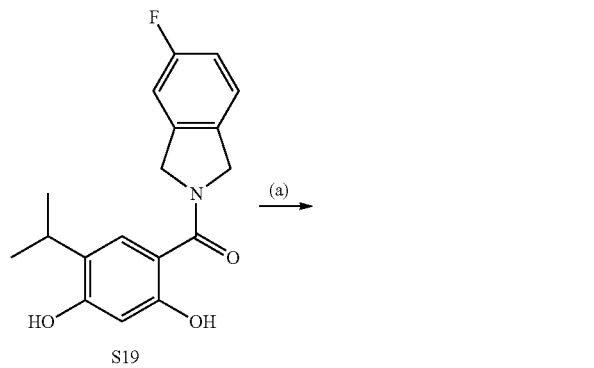

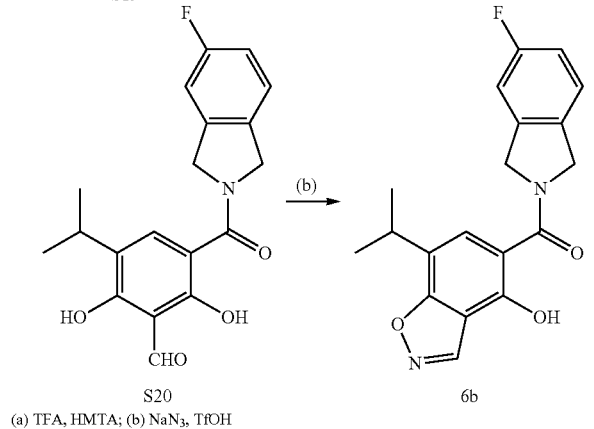

(a) TFA, HMTA; (b) NaN$_3$, TfOH

3-(5-fluoroisoindoline-2-carbonyl)-2,6-dihydroxy-5-isopropylbenzaldehyde (S20)

S20 was prepared following a reported procedure.[5-6] A solution of S19 (590 mg, 1.87 mmol, 1 eq.), hexamethylenetetramine (524 mg, 3.74 mmol, 2.0 eq.) in trifluoroacetic acid was heated at 100° C. for 14 h in a sealed tube, cooled to rt, and solvent was removed. The residue was treated with 3 M hydrochloric acid (12 mL) and the resulting mixture was heated at 60° C. for 3 h. The mixture was cooled to rt, diluted with water (30 ml), extracted with ethyl acetate (2×30 mL). The organic layer was washed with water (45 ml), saturated sodium bicarbonate solution (45 mL), and saturated sodium chloride solution (45 mL), dried over anhydrous sodium sulfate, filtered, and concentrated. The residue was purified by flash chromatography (SiO$_2$, 1:9 ethyl acetate/hexanes) to afford S17 (410 mg, 63.8%) as a pale yellow amorphous solid which was used further as obtained. $^1$H NMR (400 MHz, CDCl$_3$) δ 10.3 (s, 1H), 10.1 (s, 1H), 7.6 (s, 1H), 7.4 (s, 1H), 7.4-7.3 (m, 3H), 5.1 (s, 4H), 3.9 (hept, J=6.8 Hz, 1H), 1.3 (d, J=6.8 Hz, 6H). HRMS (ESI+) m/z [M+H$^+$] calcd for C$_{19}$H$_{19}$FNO$_4$, 344.1298, found 344.1293.

(5-fluoroisoindolin-2-yl)(4-hydroxy-5-isopropylbenzo[d]isoxazol-7-yl)methanone (6b; KUNB31b)

Triflic acid (131 μL, 1.47 mmol, 6.0 eq.) and sodium azide (24 mg, 0.37 mmol, 1.5 eq.) were added to a solution of S19 (80 mg, 0.25 mmol, 1.0 eq.) in acetonitrile (2.5 mL) at rt. The resulting mixture was stirred for 5 min and concentrated. The residue was treated with water (3 mL) and ethyl acetate (5 mL). The aqueous layer was extracted with ethyl acetate (2×4 mL) and the combined organic layers washed with saturated sodium chloride solution (8 mL), dried over anhydrous sodium sulfate, filtered, and concentrated. The residue was purified using preparatory TLC (SiO$_2$, 1:3 ethyl acetate/hexanes) to afford 6b (27.3 mg, 34.5%). $^1$H NMR (400 MHz, CDCl$_3$) δ 12.29 (s, 1H), 8.85 (s, 1H), 7.61 (s, 1H), 7.29–7.26 (m, 1H), 7.06–7.02 (m, 2H), 5.11 (d, J=9.0 Hz, 4H), 3.38 (h, J=6.9 Hz, 1H), 1.44 (d, J=6.9 Hz, 6H). $^{13}$C NMR (100 MHz, CDCl$_3$) δ 170.9, 163.5, 162.8, 155.8, 144.9, 137.6, 131.2, 126.2, 124.0, 121.6, 115.3, 112.7, 110.0, 109.8, 54.3, 53.4, 29.2, 22.5 (2). HRMS (ESI+) m/z [M+H$^+$] calcd for C$_{19}$H$_{18}$FN$_2$O$_3$, 341.1301 found 341.1304.

Preparation of Compound (9)

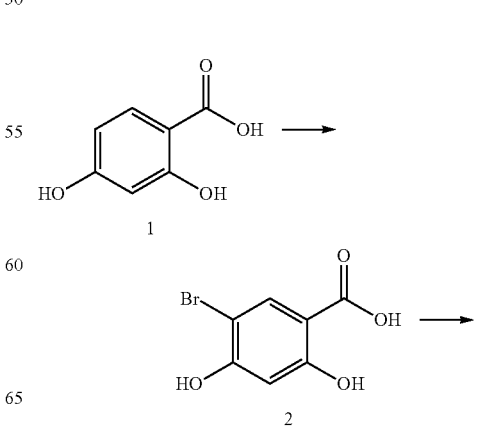

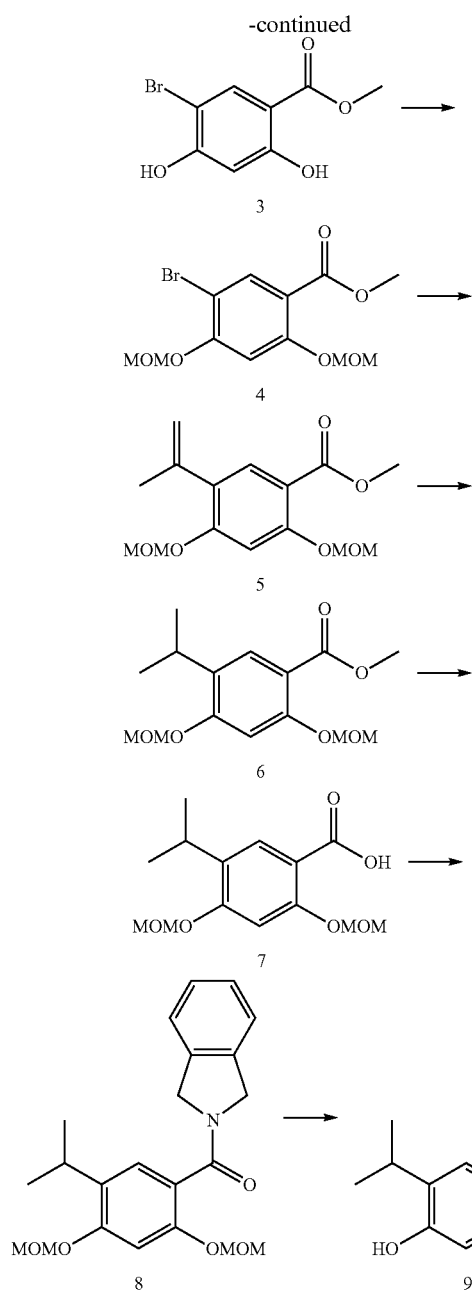

5-Bromo-2,4-hydroxybenzoic Acid (2)

A solution of bromine in chloroform was added dropwise to a solution of 1 (1 eq.) in chloroform at 0° C. (250 mL). The resulting mixture was stirred at room temperature for 4 h before quenching with 10% aqueous solution of sodium thiosulfate (200 mL). The organic layer was washed with saturated sodium bicarbonate solution (2×200 mL) and saturated sodium chloride solution (200 mL), dried over anhydrous sodium sulfate, filtered, and concentrated. The residue was purified by flash chromatography (SiO$_2$, 1:9 ethyl acetate/hexanes) to afford 2 (89.2%) as a yellow solid. $^1$H-NMR (400 MHz, CDCl$_3$) δ 16.47 (s, 1H), 12.4 (s, 1H), 9.98 (s, 1H), 8.05 (s, 1H), 6.37 (3, 1H). $^{13}$C-NMR (100 MHz, CDCl$_3$) δ 171.8, 162.6, 160.09, 136.6, 110.3, 106.3, 105.7.

Methyl-5-bromo-2,4-bis(methoxymethoxy)benzoate (4)

A solution of 3 (3.2 g, 11.63 mmol, 1 eq.) in dichloromethane (116 mL) was cooled to 0° C. before the addition of N,N-diisopropylethylamine (12.13 mL, 69.79 mmol, 9 eq.) and 6M solution of chloromethoxymethyl ether (11.8 ml, 69.79 mmol, 9 eq.). The reaction was allowed to reach at room temperature and stirred for 14 h before quenching with saturated sodium bicarbonate solution (60 mL). The aqueous layer was extracted with dichloromethane (2×60 mL) and the combined organic layers were washed with saturated sodium chloride solution (150 ml), dried over anhydrous sodium sulfate, filtered, and concentrated. The residue was purified by flash chromatography (SiO$_2$, 1:49 acetone/dichloromethane) to afford 4 (85%) as a light pink solid. $^1$H-NMR (400 MHz, CDCl$_3$) δ 8.19 (s, 1H), 8.05 (s, 1H), 6.57 (s, 1H), 6.02 (s, 2H), 6.31 (s, 2H), 3.95 (s, 3H), 3.30 (s, 3H), 3.27 (s, 3H). $^{13}$C-NMR (100 MHz, CDCl$_3$) δ169.7, 162.3, 157.9, 135.4, 108.0, 104.4, 103.3, 94.9, 94.2, 55.6 (2), 51.5.

Methyl-2,4-bis(methoxymethoxy)-5-(prop-1-en-2-yl)benzoate (5)

A microwave vial was charged with 4 (1.0 g, 1 eq.), tetrakis(triphenylphosphine)palladium (0) (0.1 eq.), cesium carbonate (3 eq.), and potassium isopropenyltrifluoroborate (1.2 eq.). The tube was sealed with a cap lined with a disposable Teflon septum. The tube was evacuated and purged with nitrogen (3 times), before the addition of anhydrous tetrahydrofuran (10.8 mL) and water (1.2 mL) by syringe. The resulting mixture was heated at 100° C. for 24 h, cooled to room temperature, and filtered through a small pad of celite (elution with ethyl acetate). Solvent was removed and the residue purified by flash chromatography (SiO$_2$, 1:3 ethyl acetate/hexanes) to afford 5 (62%) as a white solid. $^1$H-NMR (400 MHz, CDCl$_3$) δ 8.19 (s, 1H), 8.05 (s, 1H), 6.57 (s, 1H), 6.02 (s, 2H), 6.31 (s, 2H), 3.95 (s, 3H), 3.30 (s, 3H), 3.27 (s, 3H). $^{13}$C-NMR (100 MHz, CDCl$_3$) δ169.7, 162.3, 157.9, 135.4, 108.0, 104.4, 102.5, 94.9, 94.2, 55.6 (2), 51.5.

Methyl-5-isopropyl-2,4-bis(methoxymethoxy)benzoate (6)

Palladium on carbon (10%) was added to a solution of isoindolin-2-yl(2-methoxy-4-((methoxymethoxy)methyl)-5-(prop-1-en-2-yl)phenyl)methanone in ethyl acetate (25 mL). The suspension was stirred for 16 h under a hydrogen atmosphere before it was filtered through a pad of celite and eluted with ethyl acetate (20 mL). The eluent was concentrated to afford 6 (98%) as a white solid. $^1$H-NMR (400 MHz, CDCl$_3$) δ 7.99 (s, 1H), 6.68 (s, 1H), 6.05 (s, 2H), 6.01 (s, 2H), 3.95 (s, 3H), 3.45 (s, 3H), 3.32 (s, 3H), 3.05 (m, 1H), 1.17 (d, J=7.32, 6H). $^{13}$C-NMR (100 MHz, CDCl$_3$) δ 167.9, 162.3, 157.9, 135.0, 108.0, 104.4, 102.5, 94.9, 94.2, 55.6 (2), 51.5.

5-Isopropyl-2,4-bis(methoxymethoxy)benzoic Acid (7)

Lithium hydroxide monohydrate (10 eq.) was added to a solution of 6 (4.08 g, 1 eq.) in a solvent mixture of tetrahydrofuran (43 mL), water (43 mL), methanol (43 mL). The resulting mixture was stirred at room temperature for 16 h and concentrated. The residue was treated with 1 M hydrochloric acid and pH was adjusted to 2. The resulting suspension was extracted with ethyl acetate (3×100 mL), the combined organic layers were washed with saturated sodium chloride solution, dried over anhydrous sodium sulfate, filtered and concentrated to afford 7 (83.2%) as a light brown solid. $^1$H-NMR (400 MHz, CDCl$_3$) δ 12.04 (s, 1H), 8.15 (s, 1H), 6.57 (s, 1H), 6.02 (s, 2H), 6.01 (s, 2H), 3.95 (s, 3H), 3.45 (s, 3H), 3.32 (s, 3H), 3.05 (m, 1H), 1.17 (d, J=7.17, 6H). $^{13}$C-NMR (100 MHz, CDCl$_3$) δ161.7, 165.7, 156.3, 130.4, 130.2, 129.6, 100.0, 94.9, 94.2, 55.6 (2), 27.3, 23.6, 23.6.

Isoindolin-2-yl(5-isopropyl-2,4-bis(methoxymethoxy)phenyl)methanone (8)

1-Ethyl-3-(3-dimethylaminopropyl)carbodiimide (2 eq.) was added to a stirred solution of 7 (1 eq.), isoindoline hydrochloride (1.5 eq.), 1-hydroxybenzotriazole (2 eq.) N,N-diisopropylethylamine (2 eq.) in dichloromethane (150 mL) at 0° C. The resulting solution was stirred at room temperature for 14 h before quenching with saturated sodium bicarbonate solution (120 mL). The organic layer was washed with 1 M hydrochloric acid solution (120 mL) and saturated sodium chloride solution (120 mL), dried over sodium sulfate, filtered, and concentrated. The residue was purified by flash chromatography (SiO$_2$, 1:4 hexanes/ethyl acetate) to afford 8 (82%) as a white amorphous solid. $^1$H-NMR (400 MHz, CDCl3) δ 7.97 (m, 1H), 7.43 (m, 2H), 7.37 (m, 2H), 6.07 (s, 2H), 6.00 (s, 2H), 4.52 (s, 2H), 4.41 (s, 2H), 3.35 (s, 3H), 3.27 (s, 3H), 3.05 (m, 1H), 1.14 (d, J=7.52, 6H). $^{13}$C-NMR (100 MHz, CDCl$_3$) δ 169.5, 157.5, 156.6, 140.0 (2), 130.6, 128.5 (2), 126.2 (2), 126.0, 111.2, 99.9, 95.2, 94.5, 56.1, 55.6 (2), 26.9, 23.6 (2).

(2,4-dihydroxy-5-isopropylphenyl)(isoindolin-2-yl)methanone (9)

To a solution of 4N HCl in dioxane was added 8 (100 mg, 1 eq.) at 0° C. The reaction was stirred at 0° C. for 30 min then allowed to warm to room temperature for 4 h. The desired product, 9, crashed out of solution as a white solid (62%) and was gravity filtered, with no further purification necessary. $^1$H-NMR (400 MHz, CDCl$_3$) δ 9.68 (s, 1H), 7.97 (m, 1H), 7.43 (m, 2H), 7.37 (m, 2H), 6.45 (s, 1H), 4.46 (s, 4H, 3.05 (m, 1H), 1.17 (d, J=7.52, 6H). $^{13}$C-NMR (100 MHz, CDCl$_3$) δ 157.7, 155.6, 140.0 (2), 129.0, 127.3, 126.8 (2) 126.2 (2), 56.1 (2) 26.6, 23.6 (2).

Preparation of Compound KUNB1 and Compound KUNB31

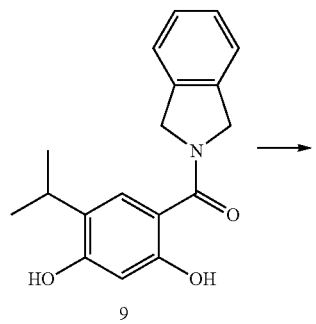

9

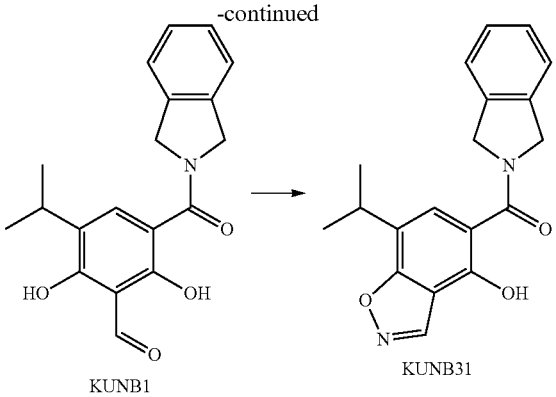

KUNB1 → KUNB31

2,6-Dihydroxy-3-(isoindoline-2-carbonyl)-5-isopropylbenzaldehyde (KUNB1)

A solution of 9 (400 mg, 1.34 mmol, 1 eq.), hexamethylenetetramine (376 mg, 2.68 mmol, 2 eq.) in trifluoroacetic acid was heated at 100° C. for 14 h in a sealed tube, cooled to room temperature, and solvent was removed. The residue was treated with 3 M hydrochloric acid and the resulting mixture was heated at 60° C. for 3 h. The mixture was cooled to room temperature, diluted with water (20 ml), extracted with ethyl acetate (2×20 mL). The organic layer was washed with water (30 ml), saturated sodium bicarbonate solution (30 mL), and saturated sodium chloride solution (30 mL), dried over anhydrous sodium sulfate, filtered, and concentrated. The residue was purified by flash chromatography (SiO$_2$, 1:9 ethyl acetate/hexanes) to afford KUNB1 (312.2 mg, 71.8%) as a pale yellow amorphous solid. $^1$H-NMR (500 MHz, CDCl$_3$) δ 13.06 (s, 1H), 12.74 (s, 1H), 10.44 (s, 1H), 252 7.74 (s, 1H), 7.34 (d, J=2.2 Hz, 4H), 5.12 (s, 4H), 3.36-3.27 (m, 1H), 1.28 (d, J=6.9 Hz, 6H). $^{13}$C-NMR (125 MHz, CDCl$_3$) δ 195.1, 170.7, 165.0, 164.0, 135.7, 133.5 (2), 128.2 (2), 126.2, 122.8 (2), 110.1, 106.9, 54.8 (2), 26.1, 22.7 (2). HRMS (ESI+) m/z [M+H$^+$] calc. for C$_{19}$H$_{20}$NO$_4$, 338.2120, found 338.2117.

(4-Hydroxy-7-isopropylbenzo[d]isoxazol-5-yl)(isoindolin-2-yl)methanone (KUNB31)

Triflic acid (79 μL, 0.90 mmol, 6 eq.) and sodium azide (15 mg, 0.23 mmol, 1.5 eq.) were added to a solution of 9 (50 mg, 0.15 mmol, 1 eq.) in acetonitrile (1.5 mL) at room temperature. The resulting mixture was stirred for 5 min and concentrated. The residue was treated with water (2 mL) and ethyl acetate (3 mL). The aqueous layer was extracted with ethyl acetate (2×3 mL) and the combined organic layers washed with saturated sodium chloride solution (6 mL), dried over anhydrous sodium sulfate, filtered, and concentrated. The residue was purified using preparatory TLC (SiO$_2$, 1:3 ethyl acetate/hexanes) to afford KUNB31 (18.3 mg, 37.8%) and 106 (13.1, 27.1%). $^1$H-NMR (400 MHz, CDCl$_3$) δ 12.42 (s, 1H), 8.86 (d, J=1.3 Hz, 1H), 7.65 (s, 1H), 7.34 (s, 4H), 5.14 (s, 4H), 3.40 (hept, J=7.0 Hz, 1H), 1.45 (d, J=7.1 Hz, 6H). $^{13}$C-NMR (100 MHz, CDCl$_3$) δ 171.1, 163.7, 156.1, 145.2, 135.9, 128.2 (2), 126.5 (2), 122.8 (2), 121.6, 112.9, 110.4, 54.2 (2), 29.4, 22.7 (2). HRMS (ESI+) m/z [M+H$^+$] calc. for C$_{19}$H$_{19}$N$_2$O$_3$, 323.1396, found 323.1392.

Preparation of Compounds KUNB2, KUNB3, KUNB14, and KUNB4

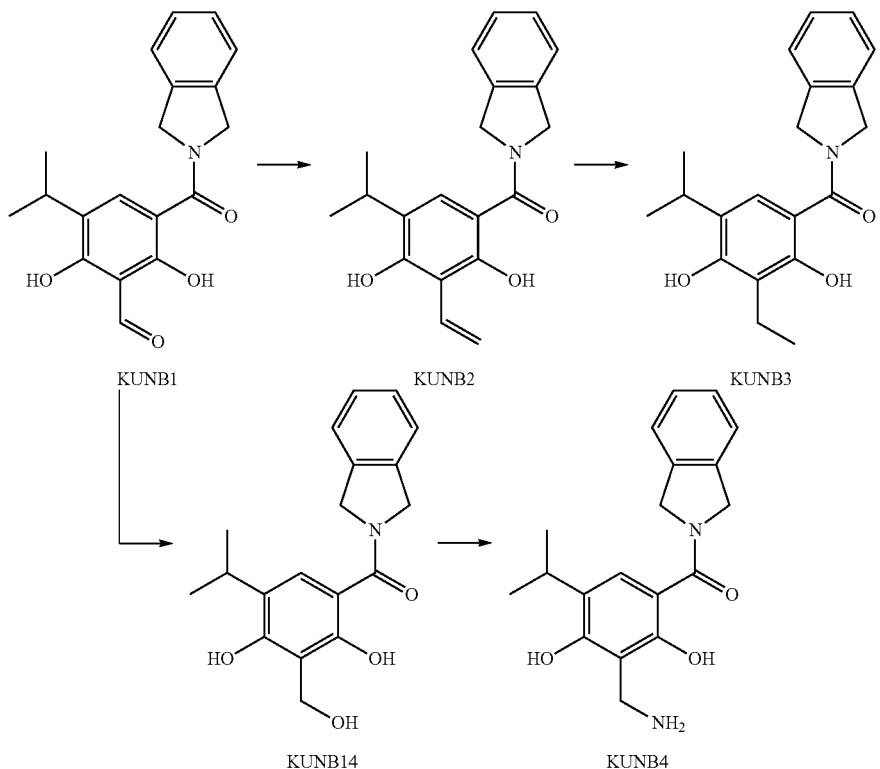

(2,4-Dihydroxy-5-isopropyl-3-vinylphenyl)(isoindolin-2-yl)methanone (KUNB2)

1.6 M solution of n-butyl lithium in hexanes (2 eq.) was added to a suspension of methyltriphenylphosphonium iodide (1 eq.) in tetrahydrofuran (1 mL) at 0° C. The resulting mixture was stirred for 30 min before the addition of a solution of KUNB1 (100 mg, 1.0 eq.) in tetrahydrofuran (1 mL) at 0° C. The reaction was warmed to room temperature and stirred for 5 h before quenching with water (10 mL). The aqueous layer was extracted with ethyl acetate (2×10 mL). The combined organic layers were washed with saturated sodium chloride solution (20 mL), dried over sodium sulfate, filtered and concentrated. The residue was purified by flash chromatography ($SiO_2$, 1:5 ethyl acetate/hexanes) to afford KUNB2 (66.6 mg, 75.9%) as a pale yellow solid. $^1$H-NMR (400 MHz, $CDCl_3$) δ 7.51 (s, 1H), 7.43 (m, 2H), 7.37 (m, 3H), 5.72 (dd, J=2.1, 16.3, 1H), 5.60 (dd, J=2.1, 10.0, 1H), 4.46 (s, 4H), 3.05 (m, 1H), 1.17 (d, J=7.52, 6H). $^{13}$C-NMR (100 MHz, $CDCl_3$) δ 157.7, 155.6, 140.0 (2), 134.5, 129.0, 127.3, 126.8 (2) 126.2 (2), 114.356.1 (2) 26.6, 23.6 (2).

(3-Ethyl-2,4-dihydroxy-5-isopropylphenyl)(isoindolin-2-yl)methanone (KUNB3)

Palladium on carbon (10%) was added to a solution of KUNB2 (60 mg) in ethyl acetate (5 mL). The suspension was stirred for 16 h under a hydrogen atmosphere before it was filtered through a pad of celite and eluted with ethyl acetate (20 mL). The eluent was concentrated to afford KUNB3 (96%) as a colorless solid. $^1$H-NMR (400 MHz, $CDCl_3$) δ 7.51 (s, 1H), 7.43 (m, 2H), 7.37 (m, 3H), 5.72 (dd, J=2.1, 16.3, 1H), 5.60 (dd, J=2.1, 10.0, 1H), 4.46 (s, 4H), 3.05 (m, 1H), 2.71 (q, 2H), 1.17 (m, 9H). $^{13}$C-NMR (100 MHz, $CDCl_3$) δ 157.7, 155.6, 140.0 (2), 134.5, 126.8 (2) 126.2 (2), 114.3, 56.1 (2) 26.6, 23.6 (2), 15.7, 15.1.

(2,4-Dihydroxy-3-(hydroxymethyl)-5-isopropylphenyl)(isoindolin-2-yl)methanone (KUNB14)

Sodium borohydride (2.8 mg, 0.06 mmol) was added to a solution of KUNB1 (20 mg, 0.07 mmol, 2.0 eq.) in a solvent mixture of tetrahydrofuran (1.5 mL) and methanol (0.5 mL) at ° C. The resulting mixture was stirred at room temperature for 1 h before the addition of 1 M hydrochloric acid (2 mL). The aqueous layer was extracted with ethyl acetate (2×5 mL), and the combined organic layers washed with saturated sodium chloride solution, dried over anhydrous sodium sulfate, filtered, and concentrated. The residue was purified by preparatory TLC ($SiO_2$, 1:3 ethyl acetate/hexanes) to give KUNB14 as a colorless amorphous solid (14.2 mg, 72.2%). $^1$H-NMR (500 MHz, $CDCl_3$) δ 11.72 (s, 1H), 8.76 (s, 1H), 7.43 (s, 1H), 7.32 (s, 4H), 5.11 (s, 6H), 3.34-3.24 (m, 1H), 2.31 (s, 1H), 1.28 (d, J=6.9 Hz, 6H), 1.18. $^{13}$C-NMR (125 MHz, $CDCl_3$) δ 171.7, 158.6, 157.1, 136.2 (2), 128.0, 126.3 (2), 125.5, 122.8 (2), 111.4, 108.3, 59.3, 54.2 (2), 26.6, 23.1 (2). HRMS (ESI+) m/z [M+H$^+$] calc. for $C_{19}H_{21}NO_4$, 328.1549, found 328.1543.

(3-(Aminomethyl)-2,4-dihydroxy-5-isopropylphenyl)(isoindolin-2-yl)methanone (KUNB4)

4.0 M ammonia in methanol (2.5 eq.) was added to a solution of KUNB14 (1 eq.) in tetrahydrofuran (1 mL). The resulting mixture was stirred at room temperature for 6 h, and concentrated. The residue was purified by flash chromatography (SiO$_2$, 1:10 241 methanol/dichloromethane) to afford KUNB4 (18%) as a light yellow solid. $^1$H-NMR (500 MHz, CDCl$_3$) δ 11.72 (s, 1H), 8.76 (s, 1H), 7.43 (s, 1H), 7.32 (s, 4H) 4.31 (s, 2H), 3.24 (m, 1H), 2.31 (s, 1H), 1.28 (d, J=6.9 Hz, 6H), 1.18. $^{13}$C-NMR (125 MHz, CDCl$_3$) δ 171.7, 158.6, 157.1, 136.2 (2), 128.0, 126.3 (2), 125.5, 122.8 (2), 111.4, 108.3, 59.3, 54.2 (2), 26.6, 23.1 (2).

Preparation of Compounds KUNB6, KUNB7, and KUNB5 reflux condenser. The crude reaction mixture was concentrated, dissolved in ethyl acetate (20 mL), washed with water (3×15 mL), dried over anhydrous sodium sulfate, filtered, and concentrated to give 13 (76%) as a colorless oil.

(3-Allyl-2-hydroxy-5-isopropyl-4-(methoxymethoxy)phenyl)(isoindolin-2-yl)methanone (KUNB6)

Diethylamine (5 mL) was added to create a solution of 13 in a microwave vial with a disposable septum. The reaction

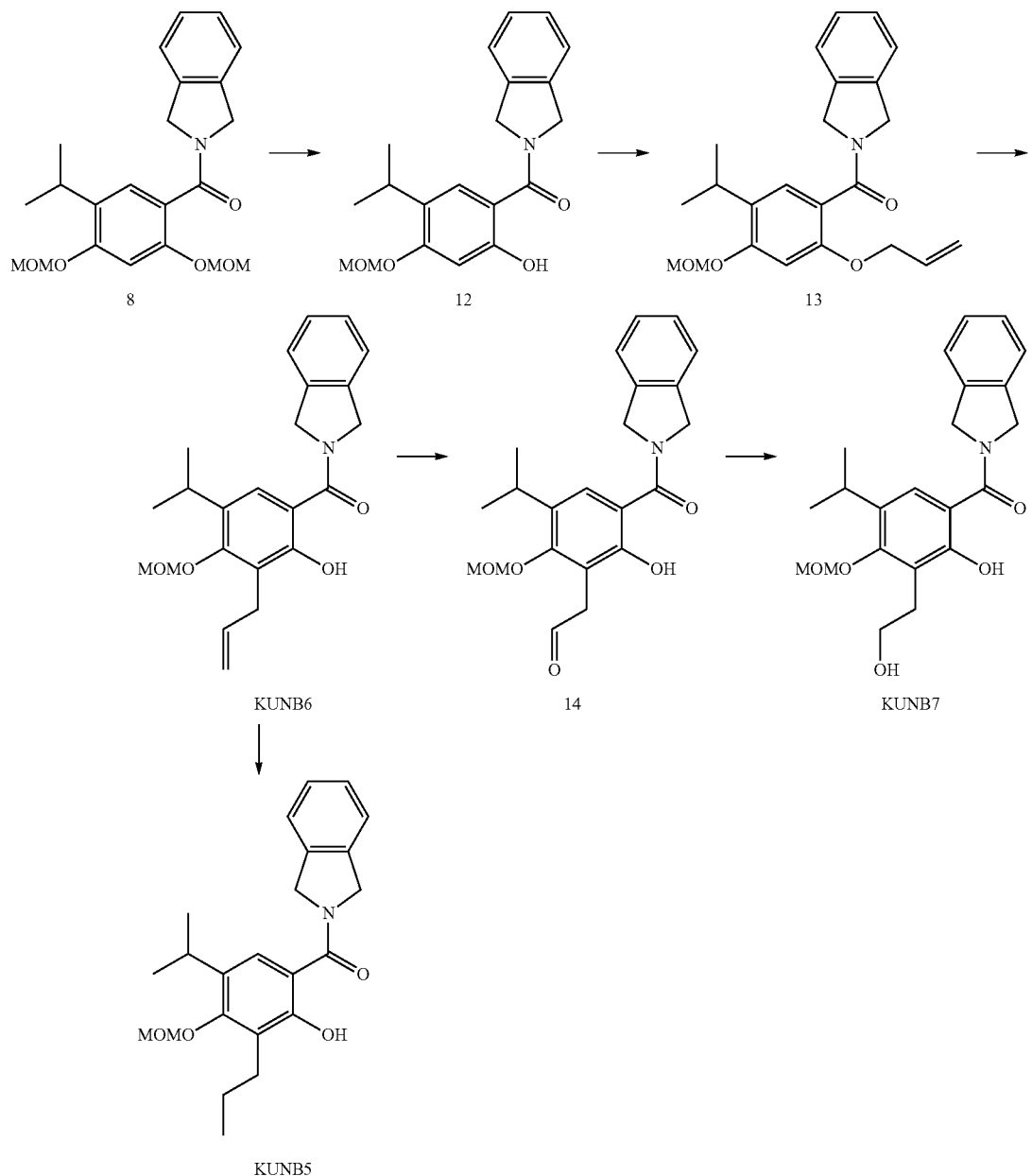

(2-(Allyloxy)-5-isopropyl-4-(methoxymethoxy)phenyl)(isoindolin-2-yl)methanone (13)

Potassium carbonate (5 eq.) and allylbromide (2 eq.) were added to a solution of 12 (0.3 g, 1 eq.) in acetone (9 mL). The reaction was stirred overnight for 12 h at 75° C., with a was stirred overnight at 220° C. for 24 h. Upon completion, the reaction mixture was quenched with 1 M hydrochloric acid (25 mL), extracted with ethyl acetate (3×10 mL), and the combined organic layers were washed with saturated sodium chloride solution, dried over anhydrous sodium sulfate, filtered, and concentrated. The residue was purified by preparatory TLC (SiO$_2$, 1:3 ethyl acetate/hexanes) to give KUNB6 as a brown amorphous solid (91%).

(2-Hydroxy-3-(2-hydroxyethyl)-5-isopropyl-4-(methoxymethoxy)phenyl) (isoindolin-2-yl)methanone (KUNB7)

Sodium borohydride (2 eq.) was added to a solution of KUNB6 (1 eq.) in a solvent mixture of tetrahydrofuran (1.5 mL) and methanol (0.5 mL) at 0° C. The resulting mixture was stirred at room temperature for 1 h before the addition of 1 M hydrochloric acid (2 mL). The aqueous layer was extracted with ethyl acetate (2×5 mL), and the combined organic layers were washed with saturated sodium chloride solution, dried over anhydrous sodium sulfate, filtered, and concentrated. The residue was purified by preparatory TLC (SiO$_2$, 1:3 ethyl acetate/hexanes) to give KUNB7 as a colorless amorphous solid (68%).

(2-Hydroxy-5-isopropyl-4-(methoxymethoxy)-3-propylphenyl)(isoindolin-2-yl)methanone (KUNB5)

Palladium on carbon (10%) was added to a solution of KUNB6 (60 mg) in ethyl acetate (5 mL). The suspension was stirred for 16 h under a hydrogen atmosphere before it was filtered through a pad of celite and eluted with ethyl acetate (20 mL). The eluent was concentrated to afford KUNB5 (96%) as a colorless solid.

Preparation of Compound (32)

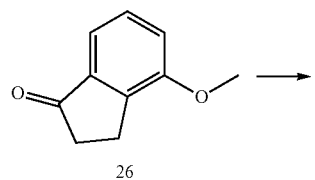

26

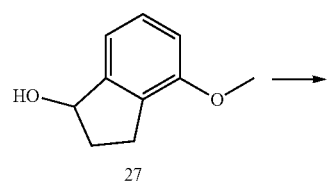

27

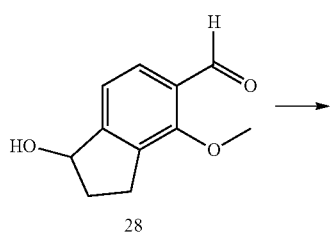

28

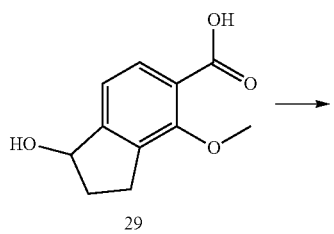

29

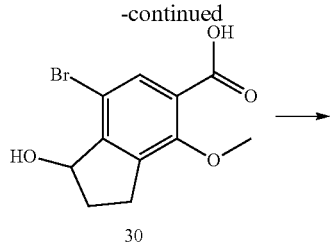

30

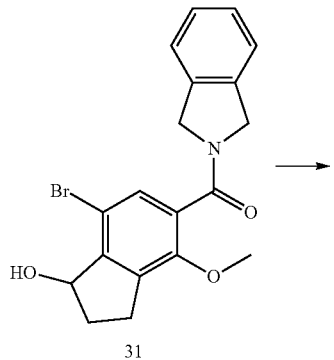

31

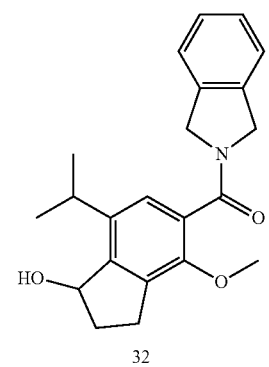 [SMILES: COc1c(C(=O)N2Cc3ccccc3C2)cc(C(C)C)c2c1CCC2O]

32

4-Methoxy-2,3-dihydro-1H-inden-1-ol (27)

Sodium borohydride (2 eq.) was added to a solution of 4-methoxy-2,3-dihydro-1H-inden-1-one (1 eq.) in a solvent mixture of tetrahydrofuran (1.5 mL) and methanol (0.5 mL) at 0° C. The resulting mixture was stirred at room temperature for 1 h before the addition of 1 M hydrochloric acid (2 mL). The aqueous layer was extracted with ethyl acetate (2×5 mL), and the combined organic layers were washed with saturated sodium chloride solution, dried over anhydrous sodium sulfate, filtered, and concentrated. The residue was purified by preparatory TLC (SiO$_2$, 1:3 ethyl acetate/hexanes) to give 27 as a colorless amorphous solid (68%). 1H NMR (500 MHz, CDCl$_3$) δ 7.13 (t, 1H), 6.90 (dd, 1H), 6.82 (dd, 1H), 5.32 (s, 1H), 5.01 (t, 1H), 3.83 (s, 3H), 3.21 (m, 2H), 2.31 (m, 2H). 13C NMR (125 MHz, CDCl$_3$) δ 160.3, 151.2, 131.3, 128.3, 127.3, 121.0, 75.6, 35.9, 20.8.

1-hydroxy-4-methoxy-2,3-dihydro-1H-indene-5-carbaldehyde (28)

A solution of 27 (400 mg, 1.34 mmol, 1 eq.), hexamethylenetetramine (376 mg, 2.68 mmol, 2 eq.) in trifluoroacetic acid was heated at 100° C. for 14 h in a sealed tube, cooled to room temperature, and solvent was removed. The residue was treated with 3 M hydrochloric acid and the resulting mixture was heated at 60° C. for 3 h. The mixture was cooled to room temperature, diluted with water (20 mL), extracted with ethyl acetate (2×20 mL). The organic layer was washed with water (30 mL), saturated sodium bicarbonate solution (30 mL), and saturated sodium chloride solution (30 mL), dried over anhydrous sodium sulfate, filtered, and concentrated. The residue was purified by flash chromatography (SiO$_2$, 1:9 ethyl acetate/hexanes) to afford 28 (71.8%) as a pale yellow amorphous solid. $^1$H-NMR (500 MHz, CDCl$_3$) and $^{13}$C-NMR (125 MHz, CDCl$_3$) confirmed formation of the desired product.

1-hydroxy-4-methoxy-2,3-dihydro-1H-indene-5-carboxylic Acid (29)

A solution of 28 (1 eq) and NaH$_2$PO$_4$ (2.5 eq) in DMSO (50.0 mL) and water (12.5 mL) at 0° C. was slowly added a solution of NaClO$_2$ (80%, 2.5 eq) in H$_2$O (12 mL). The mixture was stirred at room temperature overnight, and then saturated aqueous Na$_2$CO$_3$ (25 mL) was added. The mixture was extracted with ethyl acetate (15 mL). The aqueous phase was acidified to a pH of 1 with concentrated HCl, and then was extracted with ethyl acetate (50 mL×3). The combined organic phases were washed with water (50 mL), dried over Na$_2$SO$_4$, filtered, and concentrated. The residue was purified by flash chromatography (SiO$_2$, 3:1 to 2:1 of petroleum ether:ethyl acetate) to afford 29 (77%) as a pale yellow solid.

7-bromo-1-hydroxy-4-methoxy-2,3-dihydro-1H-indene-5-carboxylic Acid (30)

A solution of bromine in chloroform was added dropwise to a solution of 29 (1 eq.) in chloroform at 0° C. (250 mL). The resulting mixture was stirred at room temperature for 4 h before quenching with 10% aqueous solution of sodium thiosulfate (200 mL). The organic layer was washed with saturated sodium bicarbonate solution (2×200 mL) and saturated sodium chloride solution (200 mL), dried over anhydrous sodium sulfate, filtered, and concentrated. The residue was purified by flash chromatography (SiO$_2$, 1:9 ethyl acetate/hexanes) to afford 30 (89.2%) as a yellow solid. $^1$H-NMR (500 MHz, CDCl$_3$) and $^{13}$C-NMR (125 MHz, CDCl$_3$) confirmed formation of the desired product.

(7-bromo-1-hydroxy-4-methoxy-2,3-dihydro-1H-inden-5-yl)(isoindolin-2-yl)methanone (31)

1-Ethyl-3-(3-dimethylaminopropyl)carbodiimide (2 eq.) was added to a stirred solution of 30 (1 eq.), isoindoline hydrochloride (1.5 eq.), 1-hydroxybenzotriazole (2 eq.) N,N-diisopropylethylamine (2 eq.) in dichloromethane (150 mL) at 0° C. The resulting solution was stirred at room temperature for 14 h before quenching with saturated sodium bicarbonate solution (120 mL). The organic layer was washed with 1 M hydrochloric acid solution (120 mL) and saturated sodium chloride solution (120 mL), dried over sodium sulfate, filtered, and concentrated. The residue was purified by flash chromatography (SiO$_2$, 1:4 hexanes/ethyl acetate) to afford 31 (82%) as a white amorphous solid. $^1$H-NMR (500 MHz, CDCl$_3$) δ 8.06 (s, 1H), 7.43 (m, 2H), 7.37 (m, 2H), 5.32 (s, 1H), 5.01 (t, 1H), 4.46 (s, 4H), 3.87 (s, 3H), 3.11 (m, 2H), 2.06 (m, 2H). $^{13}$C-NMR (125 MHz, CDCl$_3$) δ 169.5, 156.6, 143.9, 140.0 (2), 132.8, 129.1, 126.2 (2), 126.2 (2), 115.3, 61.9, 56.1 (2), 35.2, 19.7.

(1-hydroxy-7-isopropyl-4-methoxy-2,3-dihydro-1H-inden-5-yl)(isoindolin-2-yl)methanone) (32)

A microwave vial was charged with 30 (1.0 g, 1 eq.), tetrakis(triphenylphosphine)palladium (0) (0.1 eq.), cesium carbonate (3 eq.), and potassium isopropenyltrifluoroborate (1.2 eq.). The tube was sealed with a cap lined with a disposable Teflon septum. The tube was evacuated and purged with nitrogen (3 times), before the addition of anhydrous tetrahydrofuran (10.8 mL) and water (1.2 mL) by syringe. The resulting mixture was heated at 100° C. for 24 h, cooled to room temperature, and filtered through a small pad of celite (elution with ethyl acetate). Solvent was removed and the residue purified by flash chromatography (SiO$_2$, 1:3 ethyl acetate/hexanes) to afford a white solid. Palladium on carbon (10%) was added to a solution of the resulting product of the previous Suzuki coupling in ethyl acetate (25 mL). The suspension was stirred for 16 h under a hydrogen atmosphere before it was filtered through a pad of celite and eluted with ethyl acetate (20 mL). The eluent was concentrated to afford 32 (98%) as a white solid. $^1$H-NMR (500 MHz, CDCl$_3$) δ 7.93 (s, 1H), 7.48 (m, 2H), 7.32 (m, 2H), 5.32, 5.01, 4.45 (s, 4H), 3.83 (m, 2H), 2.88 (m, 2H), 1.18 (d, J=6.8, 6H).

Preparation of Compounds KUNB22, KUNB23, KUNB24, and KUNB28

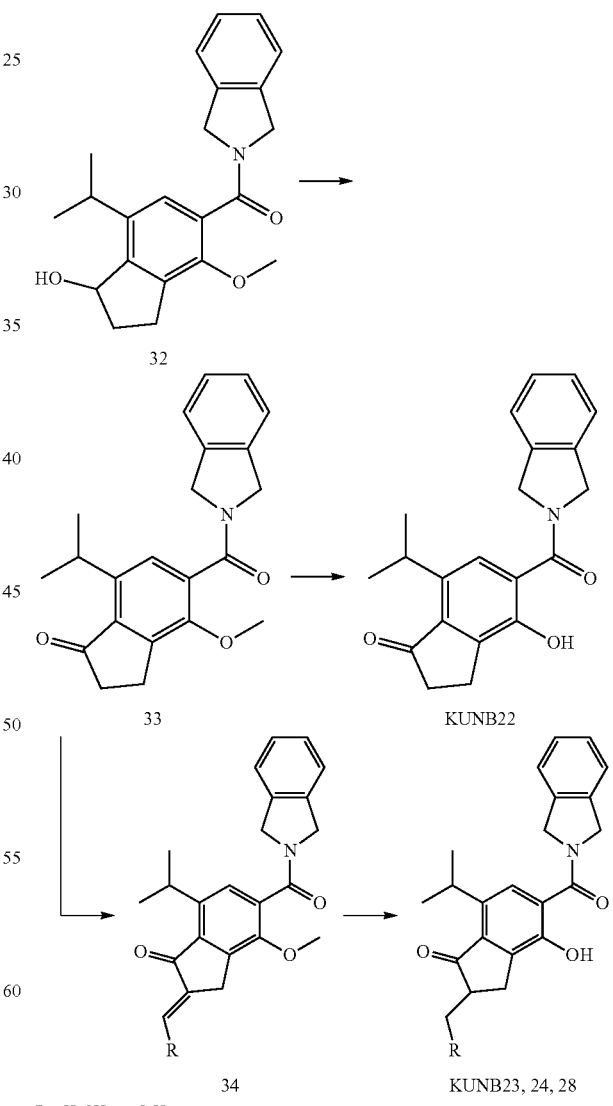

R = H, CH$_3$, or C$_2$H$_5$

5-(Isoindoline-2-carbonyl)-7-isopropyl-4-methoxy-2,3-dihydro-1H-inden-1-one (33)

Manganese dioxide (10 eq.) was added to a solution of 32 (1 eq.) in dichloromethane (120 mL) at room temperature. The resulting mixture was stirred at room temperature for 16 h, filtered through a small pad of celite, eluted with ethyl acetate, and concentrated to afford the corresponding indanone 33 (30%) as an off-white solid.

KUNB22:

1 M solution of boron tribromide (1.22 mmol, 1.22 mL, 2 eq.), was added to a solution of 33 (200 mg, 0.61 mmol) in anhydrous dichloromethane (6.1 ml) at 0° C. The resulting mixture was stirred at room temperature for 14 h before quenching with saturate sodium bicarbonate solution (5 mL). The aqueous layer was extracted with dichloromethane (2×10 mL). The combined organic layers were washed with saturated sodium chloride solution (20 mL), dried over anhydrous sodium sulfate, filtered, and concentrated. The residue was purified by flash chromatography (SiO$_2$, 1:3 ethyl acetate/hexanes) to afford KUNB22 (38 mg, 20%) as a colorless solid.

34:

To a solution of 33 (100 mg, 1 eq.) and an alkyl aldehyde (2 eq.) in ethanol (4 mL) was added to 1.0 M sodium hydroxide (10 mL) dropwise at 0° C. The reaction stirred for 2 h, and filtered upon completion. The resulting filtrate was taken up in ethyl acetate, washed with a saturated sodium chloride solution, dried over anhydrous sodium sulfate, and concentrated to yield the desired α,β-unsaturated ketone 34, where R depended on what alkyl aldehyde was utilized.

(KUNB23,24,28b):

1 M solution of boron tribromide (1.22 mmol, 1.22 mL, 2 eq.), was added to a solution of 34 (200 mg, 0.61 mmol) in anhydrous dichloromethane (6.1 ml) at 0° C. The resulting mixture was stirred at room temperature for 14 h before quenching with saturated sodium bicarbonate solution (5 mL). The aqueous layer was extracted with dichloromethane (2×10 mL). The combined organic layers were washed with saturated sodium chloride solution (20 mL), dried over anhydrous sodium sulfate, filtered, and concentrated. The residue was purified by flash chromatography (SiO$_2$, 1:3 ethyl acetate/hexanes) to afford KUNB23,24,28b, depending on the alkyl aldehyde was utilized to prepare 34.

Preparation of Compounds KUNB10 and KUNB11

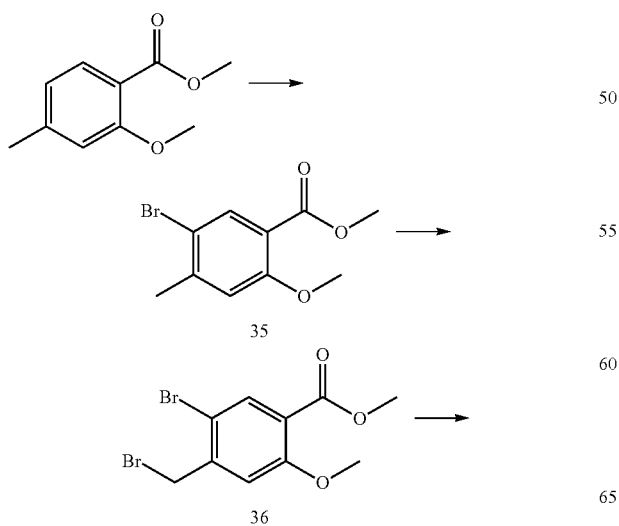

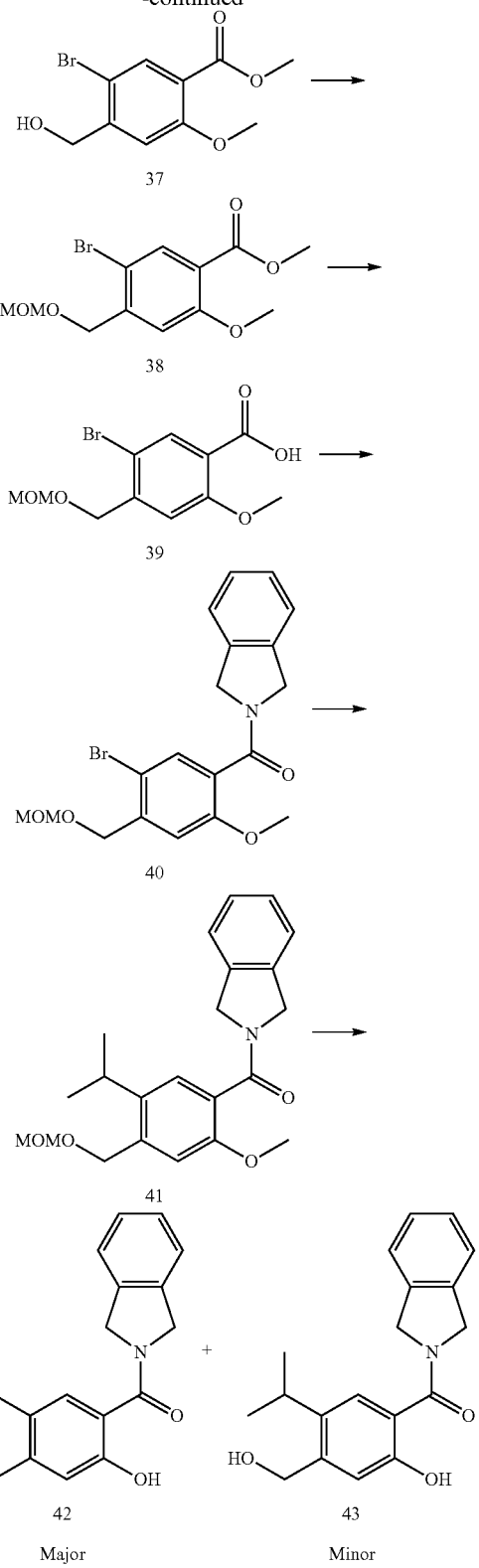

Methyl-5-bromo-2-methoxy-4-methylbenzoate (35)

A solution of bromine in chloroform was added dropwise to a solution of methyl-2-methoxy-4-methylbenzoate (10.0 g, 55.4 mmol, 1 eq.) in chloroform at 0° C. (250 mL). The resulting mixture was stirred at room temperature for 4 h before quenching with 10% aqueous solution of sodium thiosulfate (200 mL). The organic layer was washed with saturated sodium bicarbonate solution (2×200 mL) and saturated sodium chloride solution (200 mL), dried over anhydrous sodium sulfate, filtered, and concentrated. The residue was purified by flash chromatography ($SiO_2$, 1:9 ethyl acetate/hexanes) to afford 35 (12.81 g, 89.2%) as a light brown amorphous solid. $^1$H-NMR (400 MHz, $CDCl_3$) δ 7.93 (dt, J=7.1, 4.0 Hz, 1H), 6.82 (t, J=4.0 Hz, 1H), 3.97-3.76 (m, 6H), 2.38 (dt, J=6.5, 4.0 Hz, 3H). $^{13}$C-NMR (125 MHz, $CDCl_3$) δ 165.2, 158.5, 144.0, 135.2, 118.9, 114.8, 114.6, 56.3, 52.2, 23.7. HRMS (ESI+) m/z [M+H$^+$] calc. for $C_{10}H_{12}BrO_3$, 258.9969, found 258.9973.

Methyl-5-bromo-4-(bromomethyl)-2-methoxybenzoate (36)

A solution of 35 (12.8 g, 48.8 mmol), N-bromosuccinimide (9.68 g, 54.78 mmol, 1.1 eq.), azobisisobutyronitrile (1.64 g, 9.96 mmol, 0.2 eq.) in carbon tetrachloride was heated at 70° C. After 14 h, solvent was removed and the residue purified by flash chromatography ($SiO_2$, 1:9 ethyl acetate/hexanes) to afford 36 (13.92 g, 71.3%) as a white amorphous solid. $^1$H-NMR (500 MHz, $CDCl_3$) δ 7.91 (s, 1H), 7.60 (s, 1H), 7.00 (s, 1H), 3.99 (s, 3H), 3.90 (s, 3H). $^{13}$C-NMR (125 MHz, $CDCl_3$) δ 164.7, 159.0, 144.8, 135.5, 123.0, 114.6, 109.5, 56.7, 52.7, 39.3. HRMS (ESI+) m/z [M+H$^+$] calc. for $C_{10}H_{11}Br_2O_3$, 336.9075, found 336.9079.

Methyl-5-bromo-4-(hydroxymethyl)-2-methoxybenzoate (37)

Calcium carbonate (11.3 g, 113.4 mmol, 3 eq.) was added to a solution of 36 (12.8 g, 37.8 mmol, 1 eq.) in dioxane (100 mL) and water (100 mL). The resulting mixture was heated at 120° C. in a sealed tube for 16 h. The reaction mixture was cooled to room temperature, filtered, and concentrated. The residue was purified by flash chromatography ($SiO_2$, 1:5 ethyl acetate/hexanes) to afford 37 (8.2 g, 79.2%) as a colorless amorphous solid. $^1$H-NMR (500 MHz, $CDCl_3$) δ 7.9 (s, 1H), 7.2 (d, J=0.9 Hz, 1H), 4.7 (dd, J=5.7, 1.0 Hz, 2H), 3.9 (s, 3H), 3.9 (s, 3H). $^{13}$C-NMR (125 MHz, $CDCl_3$) δ 165.5, 159.0, 145.7, 135.3, 120.0, 111.9, 111.3, 64.8, 56.5, 52.5. HRMS (ESI+) m/z [M+H$^+$] calc. for $C_{10}H_{12}BrO_4$, 274.9919, found 274.9923.

Methyl-5-bromo-2-methoxy-4-((methoxymethoxy) methyl)benzoate (38)

A solution of 37 (3.2 g, 11.63 mmol, 1 eq.) in dichloromethane (116 mL) was cooled to 0° C. before the addition of N,N-diisopropylethylamine (12.13 mL, 69.79 mmol, 6 eq.) and 6M solution of chloromethoxymethyl ether (11.8 ml, 69.79 mmol, 6 eq.). The reaction was allowed to reach at room temperature and stirred for 14 h before quenching with saturated sodium bicarbonate solution (60 mL). The aqueous layer was extracted with dichloromethane (2×60 mL) and the combined organic layers were washed with saturated sodium chloride solution (150 ml), dried over anhydrous sodium sulfate, filtered, and concentrated. The residue was purified by flash chromatography ($SiO_2$, 1:49 acetone/dichloromethane) to afford 38 (2.82 g, 76.1%) as a colorless oil. $^1$H-NMR (400 MHz, $CDCl_3$) δ 7.97 (s, 1H), 7.18 (d, J=0.9 Hz, 1H), 4.80 (s, 2H), 4.64 (d, J=0.9 Hz, 2H), 3.93 (s, 3H), 3.89 (s, 3H), 3.44 (s, 3H). $^{13}$C-NMR (100 MHz, $CDCl_3$) δ 165.4, 158.9, 143.4, 135.4, 120.3, 112.4, 111.8, 96.6, 68.9, 56.6, 55.9, 52.4. HRMS (ESI+) m/z [M+H$^+$] calc. for $C_{12}H_{16}BrO_5$, 319.0181, found 319.0187.

5-Bromo-2-methoxy-4-((methoxymethoxy)methyl) benzoic Acid (39)

Lithium hydroxide monohydrate (5.37 g, 128.0 mmol, 10 eq.) was added to a solution of 38 (4.08 g, 12.8 mmol, 1 eq.) in a solvent mixture of tetrahydrofuran (43 mL), water (43 mL), methanol (43 mL). The resulting mixture was stirred at room temperature for 16 h and concentrated. The residue was treated with 1 M hydrochloric acid and pH was adjusted to 2. The resulting suspension was extracted with ethyl acetate (3×100 mL), the combined organic layers were washed with saturated a sodium chloride solution, dried over anhydrous sodium sulfate, filtered, and concentrated to afford 39 (3.26 g, 83.2%) as a light brown solid. $^1$H-NMR (500 MHz, $CDCl_3$) δ 10.59 (s, 1H), 8.33 (s, 1H), 7.30 (s, 1H), 4.83 (s, 2H), 4.67 (d, J=0.9 Hz, 2H), 4.12 (s, 3H), 3.46 (s, 3H). $^{13}$C-NMR (125 MHz, $CDCl_3$) δ 164.1, 157.5, 145.5, 137.1, 117.8, 113.9, 111.6, 96.7, 68.7, 57.3, 56.0. HRMS (ESI+) m/z [M+H$^+$] calc. for $C_{11}H_{14}BrO_5$, 305.0025, found 305.0028.

(5-Bromo-2-methoxy-4-((methoxymethoxy)methyl) phenyl)(isoindolin-2-yl)methanone (40)

1-Ethyl-3-(3-dimethylaminopropyl)carbodiimide (1.25 g, 6.54 mmol, 2 eq.) was added to a stirred solution of 39 (1.0 g, 3.27 mmol, 1 eq.), isoindoline hydrochloride (663 mg, 4.26 mmol, 1.3 eq.), 1-hydroxybenzotriazole (1.0 g, 6.54 mmol, 2 eq.), N,N-diisopropylethylamine (1.72 mL, 9.81 mmol, 3 eq.) in dichloromethane (33 mL) at 0° C. The resulting solution was stirred at room temperature for 14 h before quenching with saturated sodium bicarbonate solution (30 mL). The organic layer was washed with 1 M hydrochloric acid solution (30 mL) and saturated sodium chloride solution (30 mL), dried over sodium sulfate, filtered and concentrated. The residue was purified by flash chromatography ($SiO_2$, 1:3 hexanes/ethyl acetate) to afford 40 (1.22 g, 91.8%) as a colorless oil. $^1$H-NMR (400 MHz, $CDCl_3$) δ 7.50 (s, 1H), 7.37-7.26 (m, 3H), 7.19-7.12 (m, 2H), 4.99 (s, 2H), 4.82 (s, 2H), 4.68 (s, 2H), 4.62 (s, 2H), 3.88 (s, 3H), 3.48 (s, 3H). HRMS (ESI+) m/z [M+H$^+$] calc. for $C_{11}H_{14}BrO_5$, 452.1072, found 452.1066.

Isoindolin-2-yl(5-isopropyl-2-methoxy-4-((methoxymethoxy)methyl) phenyl)methanone (41)

A microwave vial was charged with 40 (1.0 g, 2.46 mmol, 1 eq.), Tetrakis(triphenylphosphine)palladium (0) (277 mg, 0.24 mmol, 0.1 eq.), cesium carbonate (2.4 g, 7.4 mmol, 3 eq.), and potassium isopropenyltrifluoroborate (427 mg, 2.88 mmol, 1.2 eq.). The tube was sealed with a cap lined with a disposable teflon septum. The tube was evacuated and purged with nitrogen (3 times), before the addition of tetrahydrofuran (10.8 mL) and water (1.2 mL) by syringe. The resulting mixture was heated at 100° C. for 24 h, cooled to room temperature, and filtered through a small pad of celite (elution with ethyl acetate). Solvent was removed and the residue purified by flash chromatography ($SiO_2$, 1:3 ethyl acetate/hexanes) to afford isoindolin-2-yl(2-methoxy-4-((methoxymethoxy)methyl)-5-(prop-1-en-2-yl)phenyl) methanone, which was used further as obtained. Palladium on carbon (10%) was added to a solution of isoindolin-2-yl(2-methoxy-4-((methoxymethoxy)methyl)-5-(prop-1-en- 2-yl)phenyl)methanone in ethyl acetate (25 mL). The suspension was stirred for 16 h under a hydrogen atmosphere before it was filtered through a pad of celite and eluted with ethyl acetate (20 mL). The eluent was concentrated to afford 41 (530 mg, 58.3%) as a light brown amorphous solid. $^1$H-NMR (400 MHz, CDCl$_3$) δ 7.76 (d, J=7.6 Hz, 1H), 7.60 (td, J=7.6, 1.1 Hz, 1H), 7.48 (d, J=7.7 Hz, 1H), 7.41 (t, J=7.5 Hz, 1H), 7.21 (s, 1H), 6.94 (s, 1H), 4.94 (s, 2H), 4.67 (s, 2H), 4.63 (s, 2H), 3.70 (s, 3H), 3.37 (s, 3H), 3.05 (h, J=6.8 Hz, 1H), 1.15 (s, 3H). $^{13}$C-NMR (100 MHz, CDCl$_3$) δ 168.7, 166.3, 155.0, 141.6, 139.0, 138.4, 134.1, 131.6, 128.7, 125.7, 125.4, 125.2, 123.7, 111.2, 96.0, 66.8, 56.1, 55.7, 48.7, 28.4, 24.0 (2). HRMS (ESI+) m/z [M+Na$^+$] calc. for C$_{22}$H$_{27}$NO$_4$Na, 392.1838, found 392.1838.

(4-(Bromomethyl)-2-hydroxy-5-isopropylphenyl)
(isoindolin-2-yl)methanone (42; KUNB11) &
(2-Hydroxy-4-(hydroxymethyl)-5-isopropylphenyl)
(isoindolin-2-yl)methanone (43; KUNB10)

1 M solution of boron tribromide (1.22 mmol, 1.22 mL, 2 eq.), was added to a solution of 41 (200 mg, 0.61 mmol) in anhydrous dichloromethane (6.1 ml) at 0° C. The resulting mixture was stirred at room temperature for 14 h before quenching with saturate sodium bicarbonate solution (5 mL). The aqueous layer was extracted with dichloromethane (2×10 mL). The combined organic layers were washed with saturated sodium chloride solution (20 mL), dried over anhydrous sodium sulfate, filtered, and concentrated. The residue was purified by flash chromatography (SiO$_2$, 1:50 acetone/dichloromethane) to afford 42 (KUNB11) (98 mg, 43.7%) as a white solid. Additionally, compound 43 (KUNB10) (38 mg, 20%) was also isolated.

42 (KUNB11):
$^1$H-NMR (500 MHz, CD$_2$Cl$_2$) δ 7.53 (s, 1H), 7.32 (s, 4H), 6.94 (s, 1H), 5.07 (s, 5H), 4.53 (s, 2H), 3.27 (p, J=6.8 Hz, 1H), 1.31 (d, J=6.8 Hz, 5H). $^{13}$C-NMR (125 MHz, CD$_2$Cl$_2$) δ 170.5, 157.3, 139.9 (2), 138.1 (2), 128.1, 126.3, 123.0, 119.4 (2), 119.1 (2), 118.5, 55.9 (2), 31.0, 24.3 (2). HRMS (ESI+) m/z [M+Na$^+$] calc. for C$_{19}$H$_{20}$BrNO$_2$Na, 374.756, found 374.0769.

43 (KUNB10):
$^1$H-NMR (400 MHz, CDCl$_3$) δ 10.53 (s, 1H), 7.53 (s, 1H), 7.32 (s, 4H), 7.07 (s, 1H), 5.10 (s, 4H), 4.76 (s, 2H), 3.17-3.22 (m, 1H), 1.26-1.30 (m, 6H). $^{13}$C-NMR (125 MHz, CDCl$_3$) δ 171.0, 158.0, 150.2, 143.1, 136.7, 136.4, 129.9, 129.1, 126.8, 126.6, 125.2, 116.9, 116.6, 62.9, 55.8, 53.4, 30.2, 24.5 (2). HRMS (ESI+) m/z [M+H$^+$] calc. for C$_{19}$H$_{22}$NO$_3$, 312.1600, found 312.1604.

Preparation of Compounds KUNB8, KUNB28a, KUNB30, and KUNB16

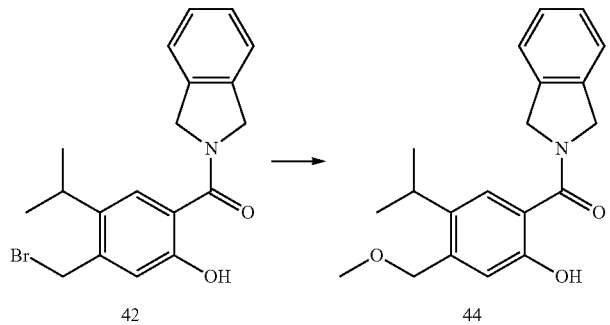

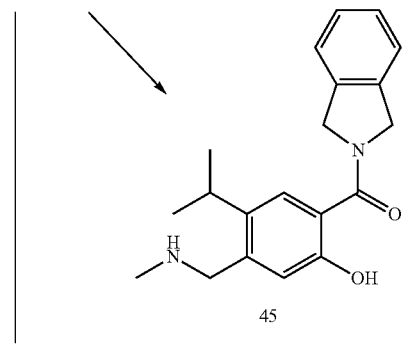

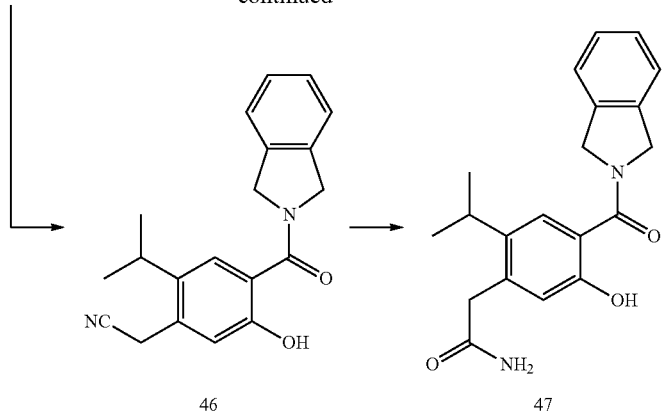

(2-Hydroxy-5-isopropyl-4-(methoxymethyl)phenyl) (isoindolin-2-yl)methanone (44; KUNB8)

Sodium methoxide (10.8 mg, 0.20 mmol, 2.5 eq.) was added to a solution of 42 (30 mg, 0.08 mmol, 1 eq.) in anhydrous methanol. The resulting mixture was heated at 60° C. for 8 h, before quenching with 1 M hydrochloric acid (2 mL), extracted with ethyl acetate (3×3 mL). The combined organic layers were washed with saturated sodium chloride solution, dried over sodium sulfate, filtered, and concentrated. The residue was purified by flash chromatography (SiO$_2$, 3:10 ethyl acetate/hexanes) to afford 44 (KUNB8) (13 mg, 49.9%) as a colorless oil. $^1$H-NMR (400 MHz, CDCl$_3$) δ 10.45 (s, 1H), 7.52 (s, 1H), 7.29 (d, J=19.5 Hz, 4H), 7.02 (s, 1H), 5.09 (s, 4H), 4.50 (s, 2H), 3.43 (s, 3H), 3.14-3.46 (m, 1H), 1.28 (d, J=6.9 Hz, 7H). $^{13}$C-NMR (100 MHz, CDCl$_3$) δ 170.8, 157.4, 140.4 (2), 137.0 (2), 127.8, 124.9 (2), 122.6, 117.8 (2), 116.6, 72.1, 58.3 (3), 28.0, 24.2 (2). HRMS (ESI+) m/z [M+Na$^+$] calc. for C$_{20}$H$_{23}$NO$_3$Na, 348.1576, found 346.1567.

(2-Hydroxy-5-isopropyl-4-((methylamino)methyl) phenyl)(isoindolin-2-yl)methanone (45; KUNB28a)

2 M methyl amine in tetrahydrofuran (0.1 mL, 0.20 mmol, 2.5 eq.) was added to a solution of 42 (30 mg, 0.08 mmol, 1 eq.) in tetrahydrofuran (1 mL). The resulting mixture was stirred at room temperature for 6 h and concentrated. The residue was purified by flash chromatography (SiO$_2$, 1:10 241 methanol/dichloromethane) to afford 45 (KUNB28a) (8 mg, 28%) as a colorless oil. $^1$H-NMR (500 MHz, CDCl$_3$) δ 7.43 (s, 1H), 7.32 (d, J=4.7 Hz, 4H), 6.97 (s, 1H), 5.07 (s, 5H), 3.78 (s, 2H), 3.21 (p, J=6.8 Hz, 1H), 2.54 (s, 3H), 1.27 (d, J=6.8 Hz, 7H). $^{13}$C-NMR (125 MHz, CDCl$_3$) δ 171.1, 157.4, 142.4, 137.2, 136.2, 128.0 (2), 125.0 (2), 122.8 (2), 118.7, 118.1, 55.5, 53.3, 52.7, 36.5, 28.2, 24.4 (2). HRMS (ESI+) m/z [M+H$^+$] calc. for C$_{20}$H$_{25}$N$_2$O$_2$, 325.1916, found 325.1904.

2-(5-Hydroxy-4-(isoindoline-2-carbonyl)-2-isopropylphenyl)acetonitrile (46: KUNB30)

Potassium cyanide (43 mg, 0.66 mmol, 5 eq.) was added to a solution of 42 (50 mg, 0.14 mmol, 1 eq.) and 18-crown-6 (71 mg, 0.27 mmol, 2 eq.) in N,N-dimethylformamide (2.0 mL) at room temperature. The reaction was stirred for 2 h, diluted with water (20 mL) and extracted with ethyl acetate (2×20 mL). The combined organic layers were washed with saturated sodium chloride solution (30 mL), dried over anhydrous sodium sulfate, filtered, and concentrated. The residue was purified by flash chromatography (SiO$_2$, 1:3 ethyl acetate/hexanes) to afford 46 (KUNB30) (39.9 mg, 92.5%) as colorless oil. $^1$H-NMR (400 MHz, CDCl$_3$) δ 10.53 (s, 1H), 7.54 (s, 1H), 7.32 (d, J=4.6 Hz, 4H), 7.03 (s, 1H), 5.09 (s, 4H), 3.74 (s, 2H), 3.07 (hept, J=6.9 Hz, 1H), 1.32 (d, J=6.8 Hz, 6H). $^{13}$C-NMR (100 MHz, CDCl$_3$) δ 170.5, 158.0, 136.5, 135.85 (2) 132.4, 128.1, 125.7 (2), 122.8, 118.6, 117.7, 117.5, 56.2 (2), 29.0, 24.1 (2), 21.7. HRMS (ESI+) m/z [M+H$^+$] calc. for C$_{20}$H$_{21}$N$_2$O$_2$, 321.1603, found 321.1610.

2-(5-Hydroxy-4-(isoindoline-2-carbonyl)-2-isopropylphenyl)acetamide (47; KUNB16)

30% Hydrogen peroxide (0.10 mL, 0.19 mmol, 3 eq.) and 2 M solution of sodium hydroxide (95 μl, 0.19 mmol, 3 eq.) was added to a solution of 46 (20 mg, 0.062 mmol, 1 eq.) in a solvent mixture of ethanol (0.5 mL) and dimethyl sulfoxide (0.2 mL). The resulting mixture was stirred for 1 h before the addition of water (3 mL). The resulting mixture was extracted with ethyl acetate (3×5 mL). The combined organic layers were washed with saturated sodium chloride solution (10 mL), dried over anhydrous sodium sulfate, filtered, and concentrated. The residue was purified by preparatory TLC (SiO$_2$, 1:9 acetone/dichloromethane) to give 47 (KUNB16) as a colorless amorphous solid (12 mg. 54.4%). $^1$H-NMR (500 MHz, CDCl$_3$) δ 10.6 (s, 1H), 7.6 (s, 1H), 7.3 (d, J=5.0 Hz, 4H), 6.9 (s, 1H), 5.4 (s, 2H), 5.1 (s, 4H), 3.6 (s, 2H), 3.1 (hept, J=6.8 Hz, 1H), 1.3 (d, J=6.8 Hz, 7H). $^{13}$C-NMR (125 MHz, CDCl$_3$) δ 172.7, 170.7, 158.0, 137.9 (2), 137.7, 135.9, 128.2, 126.0 (2), 122.9, 119.8 (2), 117.2, 55.9, 53.5, 41.3, 28.9, 24.4 (2). HRMS (ESI+) m/z [M+H$^+$] calc. for C$_{20}$H$_{22}$N$_2$O$_3$, 339.1709, found 339.1699.

Preparation of Compounds KUNB9 and KUNB15

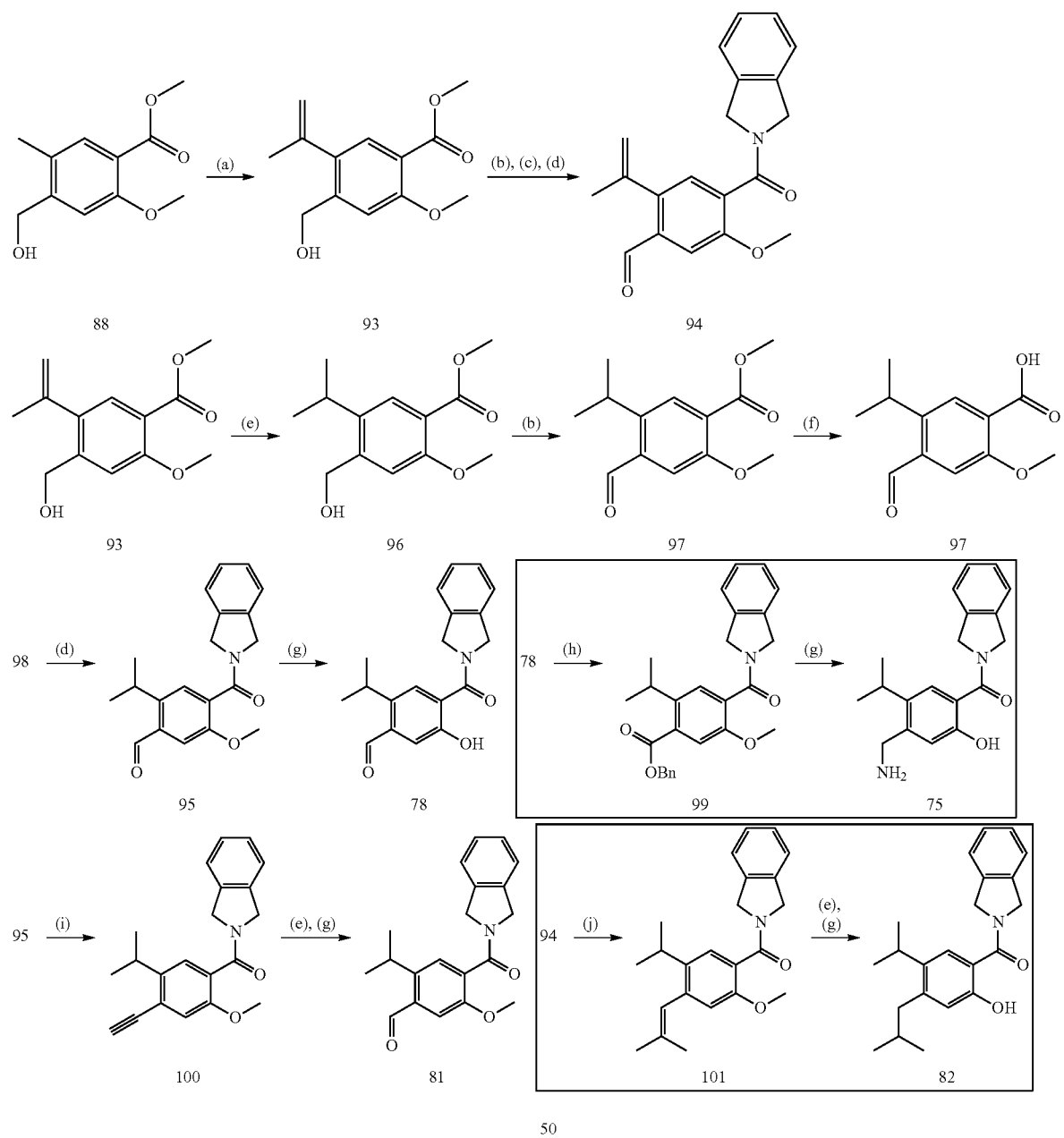

Methyl-4-formyl-2-methoxy-5-(prop-1-en-2-yl)benzoate (93)

A microwave vial was charged with 88 (0.75 g, 2.7 mmol, 1 eq.), tetrakis(triphenylphosphine)palladium(0) (312 mg, 0.27 mmol, 0.1 eq.), cesium carbonate (2.68 g, 8.25 mmol, 3 eq.), and potassium isopropenyltrifluoroborate (440 mg, 2.97 mmol, 1.2 eq.). The tube was sealed with a cap lined with a disposable teflon septum. The tube was evacuated and purged with nitrogen (3 times), before the addition of tetrahydrofuran (21.6 mL) and water (2.4 mL) by syringe. The resulting mixture was heated at 100° C. for 24 h, cooled to room temperature, and filtered through a small pad of celite (elution with ethyl acetate). Solvent was removed, and the residue was purified by flash chromatography (SiO$_2$, 1:3 ethyl acetate/hexanes) to afford 93 as a colorless amorphous solid (580 mg, 90%). $^1$H-NMR (400 MHz, CDCl$_3$) δ 7.57 (s, 1H), 7.14 (s, 1H), 5.19 (p, J=1.7 Hz, 1H), 4.82-4.76 (m, 1H), 4.69 (s, 2H), 3.84 (d, J=3.0 Hz, 6H), 2.72 (s, 1H), 2.06-1.94 (m, 3H). $^{13}$C-NMR (100 MHz, CDCl$_3$) δ 166.7, 158.4, 144.0, 143.3, 134.2, 131.3, 118.1, 116.1, 110.9, 62.5, 56.1, 52.1, 24.8. HRMS (ESI+) m/z [M+H$^+$] calc. for C$_{13}$H$_{17}$O$_4$, 237.1126, found 237.1122.

4-(Isoindoline-2-carbonyl)-5-methoxy-2-(prop-1-en-2-yl)benzaldehyde (94)

Manganese dioxide (2.80 g, 24.0 mol, 10 eq.) was added to a solution of 93 (550 mg, 2.40 mmol, 1 eq.) in dichloromethane (120 mL) at room temperature. The resulting mixture was stirred at room temperature for 16 h, filtered through a small pad of celite, eluted with ethyl acetate, and concentrated. Solvent was removed to give the corresponding aldehyde, which was used further as obtained. Lithium hydroxide monohydrate (1.02 g, 24.0 mmol) was added to a solution of the aldehyde in methanol (8 mL), tetrahydrofuran (8 mL), and water (8 mL). The resulting mixture was stirred for 14 h at room temperature. The residue was treated with 1 M hydrochloric acid and the pH was adjusted to 2. The resulting suspension was extracted with ethyl acetate (3×50 mL), and the combined organic layers were washed with saturated sodium chloride solution (100 mL), dried over anhydrous sodium sulfate, filtered, and concentrated to afford the corresponding acid as an off-white solid which was used further as obtained. 1-Ethyl-3-(3-dimethylaminopropyl)carbodiimide (1.53 g, 4.80 mmol) was added to a stirred solution of the acid, isoindoline hydrochloride (485 mg, 3.12 mmol), 1-hydroxybenzotriazole (735 mg, 4.8 mmol), N,N-diisopropylethylamine (1.25 mL, 7.20 mmol) in dichloromethane (24 mL) at 0° C. The resulting solution was stirred at room temperature for 14 h before quenching with a saturated sodium bicarbonate solution (20 mL). The organic layer was washed with 1 M hydrochloric acid solution (15 mL) and saturated sodium chloride solution (20 mL), dried over anhydrous sodium sulfate, filtered, and concentrated. The residue was purified by flash chromatography (SiO$_2$, 1:3 hexanes/ethyl acetate) to afford 94 as a light brown amorphous solid (331 mg, 43%). HRMS (ESI+) m/z [M+H$^+$] calc. for C$_{20}$H$_{20}$NO$_3$, 322.1443, found 322.1449.

Methyl-4-(hydroxymethyl)-5-isopropyl-2-methoxybenzoate (96)

Palladium on carbon (10%) was added to a solution of 93 (500 mg, 2.11 mmol) in ethyl acetate (6 mL). The suspension was stirred for 16 h under a hydrogen atmosphere before it was filtered through a pad of celite and eluted with ethyl acetate (20 mL). The eluent was concentrated to afford 96 (476 mg, 94.2%) as a colorless amorphous solid. $^1$H-NMR (400 MHz, CDCl$_3$) δ 7.71 (s, 1H), 7.06 (s, 1H), 4.78 (s, 2H), 3.88 (s, 3H), 3.84 (s, 3H), 3.06 (hept, J=6.9 Hz, 1H), 1.22 (d, J=6.8 Hz, 6H). $^{13}$C-NMR (100 244 MHz, CDCl$_3$) δ 167.1, 157.5, 143.7, 137.9, 128.9, 118.9, 111.1, 62.5, 56.3, 52.2, 28.0, 23.9 (2). HRMS (ESI+) m/z [M+Na$^+$] calc. for C$_{13}$H$_{18}$O$_4$Na, 261.1103, found 261.1091.

Methyl-4-formyl-5-isopropyl-2-methoxybenzoate (97)

Manganese dioxide (1.64 g, 18.8 mmol, 10 eq.) was added to a solution of 96 (450 mg, 1.88 mmol, 1 eq.) in dichloromethane at room temperature. The resulting mixture was stirred at room temperature for 16 h, filtered through a small pad of celite, eluted with ethyl acetate, and concentrated. The residue was purified by flash chromatography (SiO$_2$, 1:6 ethyl acetate/hexanes) to afford 97 (367.3 mg, 82.7%) as a yellow colorless solid. $^1$H-NMR (400 MHz, CDCl$_3$) δ 10.44 (s, 1H), 7.77 (s, 1H), 7.40 (s, 1H), 3.91 (d, J=3.5 Hz, 6H), 3.84-3.75 (m, 1H), 1.30 (d, J=6.9 Hz, 6H). $^{13}$C-NMR (100 MHz, CDCl$_3$) δ 190.9, 166.5, 156.8, 143.2, 136.1, 129.6, 125.6, 112.0, 56.4, 52.5, 27.2, 24.2 (2). HRMS (ESI+) m/z [M+H$^+$] calc. for C$_{13}$H$_{17}$O$_4$, 237.1127, found 237.1117.

4-Formyl-5-isopropyl-2-methoxybenzoic Acid (98)

Trimethyltin hydroxide (3.63 g, 20.1 mmol, 4 eq.) was added to solution of 97 (1.12 g, 5.03 mmol, 1 eq.) in 1,2 dichloroethane (25 mL). The resulting mixture was heated at 75° C. for 50 h, cooled to room temperature, and concentrated. The residue was suspended in ethyl acetate (100 mL), washed with 1 M hydrochloric acid (3×60 mL) and saturated sodium chloride solution (100 mL). The solvent was removed to afford 98 (952 mg, 85.1%) as a colorless amorphous solid. $^1$H-NMR (400 MHz, CDCl$_3$) δ 10.74 (s, 1H), 10.52 (s, 1H), 8.27 (s, 1H), 7.53 (s, 1H), 4.13 (s, 3H), 3.79-4.13 (m, 1H), 1.36 (d, J=6.8 Hz, 6H). $^{13}$C-NMR (100 MHz, CDCl$_3$) δ 190.4, 164.9, 156.2, 145.1, 137.5, 132.6, 122.3, 111.5, 57.3, 27.4, 24.3. HRMS (ESI−) m/z [M−H$^+$] calc. for C$_{12}$H$_{13}$O$_4$, 221.0814, found 221.0809.

4-(Isoindoline-2-carbonyl)-2-isopropyl-5-methoxybenzaldehyde (95)

1-Ethyl-3-(3-dimethylaminopropyl)carbodiimide (1.63 g, 8.54 mmol, 2.0 eq.) was added to a stirred solution of 98 (950 mg, 4.27 mmol, 1 eq.), isoindoline hydrochloride (731 mg, 4.70 mmol, 1.1 eq.), 1-hydroxybenzotriazole (635 mg, 4.70 mmol, 1.1 eq.) N-,N-diisopropylethylamine (3.26 mL, 18.8 mmol, 4.4 eq.) in dichloromethane 42 mL) at 0° C. The resulting solution was stirred at room temperature for 14 h before quenching with saturated sodium bicarbonate solution (30 mL). The organic layer was washed with 1 M hydrochloric acid solution (30 mL) and saturated sodium chloride solution (30 mL), dried over anhydrous sodium sulfate, filtered and concentrated. The residue was purified by flash chromatography (SiO$_2$, 3:10 hexanes/ethyl acetate) to afford 95 (1.22 g, 91.8%) as a white amorphous solid. $^1$H-NMR (400 MHz, CDCl$_3$) δ 10.47 (s, 1H), 7.48-7.21 (m, 5H), 7.15 (d, J=7.4 Hz, 1H), 5.01 (s, 2H), 4.58 (s, 2H), 4.02-3.76 (m, 4H), 1.32 (d, J=6.8 Hz, 7H). $^{13}$C-NMR (100 MHz, CDCl$_3$) δ 190.8, 167.6, 153.7, 144.9, 136.4, 136.4, 134.4, 132.5, 128.0, 127.7, 126.1, 123.3, 122.7, 111.2, 56.1, 53.4, 52.3, 27.3, 24.4 (2). HRMS (ESI+) m/z [M+Na$^+$] calc. for C$_{20}$H$_{21}$NO$_3$Na, 346.1419, found 346.1404.

5-Hydroxy-4-(isoindoline-2-carbonyl)-2-isopropyl-benzaldehyde (78)

1 M solution of boron tribromide (1.22 mmol, 1.22 mL, 2 eq.), was added to a solution of 95 (200 mg, 0.61 mmol) in anhydrous dichloromethane (6.1 ml) at 0° C. The resulting mixture was stirred at room temperature for 14 h before quenching with saturate sodium bicarbonate solution (5 mL). The aqueous layer was extracted with dichloromethane (2×10 mL). The combined organic layers were washed with saturated sodium chloride solution (20 mL), dried over sodium sulfate, filtered and concentrated. The residue was purified by flash chromatography (SiO$_2$, 1:50 acetone/dichloromethane) to afford 78 (121.8 mg, 63.7%) as a colorless solid. $^1$H-NMR (400 MHz, CDCl$_3$) δ 10.31 (s, 1H), 10.11 (s, 1H), 7.64 (s, 1H), 7.43 (s, 1H), 7.37-7.29 (m, 4H), 5.08 (s, 5H), 3.93 (h, J=6.9 Hz, 1H), 1.34 (d, J=6.7 Hz, 6H). HRMS (ESI−) m/z [M−H$^+$] calc. for C$_{19}$H$_{18}$NO$_3$, 308.1287, found 308.1282.

Benzyl-(4-(isoindoline-2-carbonyl)-2-isopropyl-5-methoxybenzyl)carbamate (99)

Benzyl carbamate (109 mg, 0.72 mmol, 3 eq.), triethyl silane (114 μl, 0.72 mmol, 3 eq.) and trifluoroacetic acid (36 μl, 0.48 mmol. 2 eq.) were added to a solution of 78 (75 mg, 0.24 mmol, 1 eq.) in acetonitrile (2.5 mL). The resulting mixture was stirred for 24 h before quenching with saturated sodium bicarbonate solution (10 mL). The aqueous layer was extracted with ethyl acetate (2×10 mL). The combined organic layers were washed with saturated sodium chloride solution (15 mL), dried over sodium sulfate, filtered, and concentrated. The residue was purified by flash chromatography (SiO$_2$, 1:2 ethyl acetate/hexanes) to afford 99 (93.7 mg, 87.9%) as a colorless oil. $^1$H-NMR (400 MHz, CDCl$_3$) δ 10.52 (s, 1H), 7.50 (s, 1H), 7.41-7.27 (m, 9H), 6.92 (s, 1H), 5.15 (s, 3H), 5.06 (s, 4H), 4.45 (d, J=5.9 Hz, 2H), 3.20-3.05 (m, 1H), 1.27 (d, J=6.8 Hz, 6H). $^{13}$C-NMR (100 MHz, CDCl$_3$) δ 170.8, 157.7, 156.4, 136.7, 136.6, 136.0, 128.7 (3), 128.3 (2), 128.3 (2), 128.0, 125.3 (2), 122.8 (2), 117.0, 116.8, 67.1, 55.6, 55.3, 42.4, 28.2, 24.3 (2). HRMS (ESI+) m/z [M+H$^+$] calc. for C$_{27}$H$_{29}$N$_2$O$_4$, 445.2127, found 445.2131.

(4-(Aminomethyl)-2-hydroxy-5-isopropylphenyl)(isoindolin-2-yl)methanone (75; KUNB9)

Palladium on carbon (10%) was added to a solution of 99 (93 mg, 0.21 mmol) in ethyl acetate (5 mL). The suspension was stirred for 16 h under a hydrogen atmosphere before it was filtered through a pad of celite and eluted with ethyl acetate (20 mL). The eluent was concentrated to afford 75 (KUNB9) (36 mg, 55.6%) as a colorless oil. $^1$H-NMR (400 MHz, CDCl$_3$) δ 7.48 (s, 1H), 7.31 (s, 4H), 6.99 (s, 1H), 5.08 (s, 4H), 3.91 (s, 2H), 3.17 (hept, J=6.8 Hz, 1H), 1.28 (d, J=6.8 Hz, 6H). $^{13}$C-NMR (100 MHz, CDCl$_3$) δ 171.0, 157.7, 145.4, 136.4, 136.1 (2), 128.0 (2), 125.1, 122.8 (2), 116.6, 116.4, 53.6 (2), 43.4, 28.1, 24.5 (2). HRMS (ESI+) m/z [M+H$^+$] calc. for C$_{19}$H$_{23}$N$_2$O$_2$, 311.1760, found 311.1774.

(4-Ethynyl-5-isopropyl-2-methoxyphenyl)(isoindolin-2-yl)methanone (100)

Dimethyl-1-diazo-2-oxopropylphosphonate (60 μL, 0.40 mmol, 1.2 eq.) was added to a stirred solution of 95 (100 mg, 0.31 mmol, 1 eq.) and potassium carbonate (86 mg, 0.62 mmol, 2 eq.) in methanol (3.1 mL). The resulting mixture was stirred for 24 h at room temperature and diluted with ethyl acetate (10 mL). The organic layer was washed with saturated sodium bicarbonate solution (10 mL), dried over anhydrous sodium sulfate, filtered, and concentrated. The residue was purified by flash chromatography (SiO$_2$, 1:3 ethyl acetate/hexanes) to afford 100 (77.1 mg, 78.1%) as a colorless oil. $^1$H-NMR (400 MHz, CDCl$_3$) δ 7.35-7.23 (m, 3H), 7.21 (s, 1H), 7.13 (d, J=7.4 Hz, 1H), 7.05 (s, 1H), 4.98 (s, 2H), 4.58 (s, 2H), 3.81 (d, J=1.3 Hz, 3H), 3.82-3.40 (m, 1H), 3.33 (s, 1H), 1.24 (d, J=7.1 Hz, 6H). $^{13}$C-NMR (100 MHz, CDCl$_3$) δ 168.1, 152.9, 144.3, 136.7, 136.5, 127.9, 127.8, 127.6, 124.7, 123.2, 122.9, 122.7, 115.5, 82.0, 81.8, 56.0, 53.4, 52.2, 31.0, 23.3 (2). HRMS (ESI+) m/z [M+H$^+$] calc. for C$_{21}$H$_{22}$NO$_2$, 320.1651, found 320.1660.

(4-Ethyl-5-isopropyl-2-methoxyphenyl)(isoindolin-2-yl)methanone (81)

Palladium on carbon (10%) was added to a solution of 95 (75 mg, 0.23 mmol) in ethyl acetate (10 mL). The suspension was stirred for 16 h under a hydrogen atmosphere before it was filtered through a pad of celite and eluted with ethyl acetate (20 mL). The eluent was concentrated to afford (4-ethyl-5-isopropyl-2-methoxyphenyl)(isoindolin-2-yl)methanone (72.1 mg, 97.6%) as a colorless amorphous solid. $^1$H-NMR (400 MHz, CDCl$_3$) δ 7.37-7.24 (m, 3H), 7.19 (s, 1H), 7.14 (d, J=7.4 Hz, 1H), 6.75 (s, 1H), 5.00 (s, 2H), 4.63 (s, 2H), 3.83 (s, 3H), 3.11-3.18 (m, 1H), 2.71 (q, J=7.5 Hz, 2H), 1.21-1.27 (m, 9H). $^{13}$C-NMR (100 MHz, CDCl$_3$) δ 168.1, 152.9, 144.3, 136.7, 136.5, 127.9, 127.8, 127.6, 124.7, 123.2, 122.9, 122.7, 115.5, 82.0, 81.8, 56.0, 53.4, 52.2, 31.0, 23.3 (2). HRMS (ESI+) m/z [M+H$^+$] calc. for C$_{21}$H$_{26}$NO$_2$, 324.1963, found 324.1969. 1 M solution of boron tribromide (0.38 mmol, 0.38 mL, 2 eq.) was added to a solution of (4-ethyl-5-isopropyl-2-methoxyphenyl)(isoindolin-2-yl)methanone (60 mg, 0.19 mmol) in anhydrous dichloromethane (2 mL) at 0° C. The resulting mixture was stirred at room temperature for 14 h before quenching with saturate sodium bicarbonate solution (5 mL). The aqueous layer was extracted with dichloromethane (2×10 mL). The combined organic layers were washed with saturated sodium chloride solution (20 mL), dried over anhydrous sodium sulfate, filtered, and concentrated. The residue was purified by flash chromatography (SiO$_2$, 1:2 ethyl acetate/hexanes) to afford 81 (33.2 mg, 56.7%) as a pale yellow oil. $^1$H-NMR (400 MHz, CDCl$_3$) δ 10.54 (s, 1H), 7.40 (s, 1H), 7.30-7.18 (m, 4H), 6.75 (s, 1H), 5.02 (s, 4H), 3.09 (hept, J=6.7 Hz, 1H), 2.61 (q, J=7.6 Hz, 2H), 1.15-1.21 (m, 9H). $^{13}$C-NMR (100 MHz, CDCl$_3$) δ 171.3, 157.9, 147.3, 136.7, 136.2 (2), 128.0, 124.9, 122.8 (2), 117.5 (2), 115.0, 56.1 (2), 28.2, 25.8, 24.5 (2), 15.4. HRMS (ESI+) m/z [M+H$^+$] calc. for C$_{20}$H$_{24}$NO$_2$, 310.1807, found 310.1794.

Isoindolin-2-yl(5-isopropyl-2-methoxy-4-(2-methylprop-1-en-1-yl)phenyl)methanone (101)

1.6 M Solution of n-butyl lithium in hexanes (0.32 mL, 0.5 mmol, 2 eq.) was added to a suspension of isopropyltriphenylphosphonium iodide (216 mg, 0.5 mmol, 1 eq.) in tetrahydrofuran (1 mL) at 0° C. The resulting mixture was stirred for 30 min before the addition of a solution of 95 (80 mg, 0.25 mmol, 1 eq.) in tetrahydrofuran (1 mL) at 0° C. The reaction was warmed to room temperature and stirred for 5 h before quenching with water (10 mL). The aqueous layer was extracted with ethyl acetate (2×10 mL). The combined organic layers were washed with a saturated sodium chloride solution (20 mL), dried over sodium sulfate, filtered, and concentrated. The resultant residue was purified by flash chromatography (SiO$_2$, 1:5 ethyl acetate/hexanes) to afford 101 (66.6 mg, 75.9%) as a pale yellow oil. $^1$H-NMR (400 MHz, CDCl$_3$) δ 7.37-7.24 (m, 4H), 7.16 (d, J=5.1 Hz, 2H), 6.78 (s, 1H), 6.25 (s, 1H), 5.14-5.12 (m, 1H), 5.01 (s, 2H), 4.93-4.85 (m, 1H), 4.67 (s, 2H), 3.84 (s, 3H), 1.99 (s, 3H), 1.91 (s, 3H), 1.81 (s, 3H). $^{13}$C-NMR (100 MHz, CDCl$_3$) δ 168.6, 153.8, 144.8, 138.8, 136.9, 136.7, 136.5, 135.7, 127.8, 127.6, 127.5, 125.0, 124.6, 123.3, 122.7, 115.7, 113.0, 56.0, 53.6, 52.2, 26.4, 24.2, 19.7. HRMS (ESI+) m/z [M+H$^+$] calc. for C$_{23}$H$_{26}$NO$_2$, 310.1807, found 310.1794.

(2-Hydroxy-4-isobutyl-5-isopropylphenyl)(isoindolin-2-yl)methanone (82; KUNB15)

Palladium on carbon (10%) was added to a solution of 101 (60 mg, 0.17 mmol) in ethyl acetate (5 mL). The suspension was stirred for 16 h under a hydrogen atmosphere before it was filtered through a pad of celite and eluted with EtOAc (20 mL). The eluent was concentrated to afford (4-isobutyl-5-isopropyl-2-methoxyphenyl)(isoindolin-2-yl)methanone (56.3 mg, 94.2%) as a colorless amorphous solid. $^1$H-NMR (400 MHz, CDCl$_3$) δ 7.38-7.22 (m, 3H), 7.20 (s, 1H), 7.14 (d, J=7.3 Hz, 1H), 6.67 (s, 1H), 5.00 (s, 2H), 4.62 (s, 2H), 3.81 (s, 3H), 3.13 (hept, J=6.9 Hz, 1H), 2.54 (d, J=7.2 Hz, 2H), 1.85 (dquin, J=13.6, 6.8 Hz, 1H), 1.20 (d, J=6.8 Hz, 6H), 0.97 (d, J=6.6 Hz, 6H). $^{13}$C-NMR (100 MHz, CDCl$_3$) δ 169.2, 152.8, 141.3, 139.8, 137.0, 136.8, 127.8, 127.5, 124.9, 124.8, 123.2, 122.7, 113.2, 55.9, 53.5, 52.2, 42.6, 30.4, 28.4, 24.4 (2), 22.8 (2). HRMS (ESI+) m/z [M+H$^+$] calc. for C$_{23}$H$_{30}$NO$_2$, 352.2277, found 352.2275. 1 M solution of boron tribromide (0.34 mmol, 0.34 mL, 2 eq.), was added to a solution of (4-isobutyl-5-isopropyl-2-methoxyphenyl)(isoindolin-2-yl)methanone (60 mg, 0.17 mmol) in anhydrous dichloromethane (2 251 mL) at 0° C. The resulting mixture was stirred at room temperature for 14 h before quenching with saturate sodium bicarbonate solution (5 mL). The aqueous layer was extracted with dichloromethane (2×10 mL). The combined organic layers were washed with saturated sodium chloride solution (20 mL), dried over sodium sulfate, filtered, and concentrated. The residue was purified by flash chromatography (SiO$_2$, 1:3 ethyl acetate/hexanes) to afford 82 (KUNB15) (33.2 mg, 56.7%) as a colorless amorphous solid. $^1$H-NMR (500 MHz, CDCl$_3$) δ 10.60 (s, 1H), 7.48 (s, 1H), 7.32 (s, 4H), 6.77 (s, 1H), 5.10 (s, 4H), 3.16 (sept, J=6.8 Hz, 1H), 2.51 (d, J=7.2 Hz, 2H), 1.87 (dt, J=13.5, 6.8 Hz, 1H), 1.26 (d, J=6.8 Hz, 7H), 0.96 (d, J=6.6 Hz, 6H). $^{13}$C-NMR (125 MHz, CDCl$_3$) δ 171.3, 157.4, 144.8, 137.3, 136.2 (2), 128.0, 125.1, 122.8, 119.1, 115.2, 55.9, 53.5, 42.2, 30.1, 28.3, 24.7 (2), 22.9 (2). HRMS (ESI+) m/z [M+H$^+$] calc. for C$_{22}$H$_{28}$NO$_2$, 338.2120, found 338.2125.

Routes to Provide for Modified KUNB22 pH 7.3, 50 mM KCl, 5 mM MgCl$_2$, 20 mM Na$_2$MoO$_4$, 2 mM DTT, 0.1 mg/mL BGG, and 0.01% NP-40) containing 6 nM FITC-GDA (fluorescent tracer, stock in DMSO and diluted in assay buffer) and 50 µL of assay buffer containing 10 nM of either Grp94 or Hsp90α were added to each well. Compounds were tested in triplicate wells (1% DMSO final concentration). For each plate, wells containing buffer only (background), tracer in buffer only (low polarization control), and protein and tracer in buffer with 1% DMSO (highpolarization control) were included. Plates were incubated at 4° C. with rocking for 24 h. Polarization values (in mP units) was measured at 37° C. with an excitation filter at 485 nm and an emission filter at 528 nm. Polarization values were correlated to % tracer bound and compound concentrations. The concentration at which the tracer was 50% displaced by the inhibitor was determined using Graphpad Prism.

Anti-Proliferation Assay for HEK-293, HT29 and NCI-H23 Cells.

Cells were grown to confluence and seeded at 2000 cells/well/0.1 mL in a 96-well plate and placed back in the incubator for 24 h. Compounds or vehicle were administered

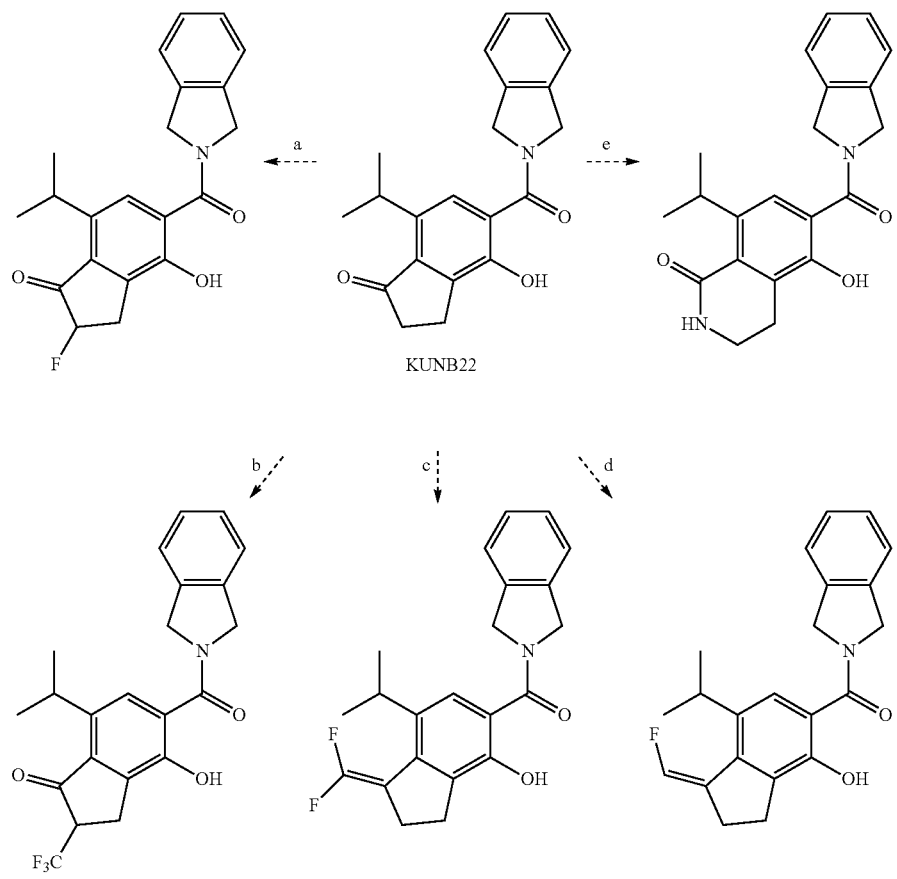

a) 1-Chloromethyl-4-fluoro-1,4-diazoniabicyclo[2.2.2]octane bis(tetrafluoroborate)
b) CuSCN, DMF, TMSCF$_3$
c) Toluene, corresponding Wittig salt, 90° C., 12 h
d) Toluene, corresponding Wittig salt, 90° C., 12 h
e) TMSN$_3$, FeCl, DCM, 0° C., 1 h Florescence Polarization.

Assay was performed in 96-well format in black, flat bottom plates (Santa Cruz Biotechnology) with a final volume of 100 µL. 25 µL of assay buffer (20 mM HEPES, at the desired concentrations (1% DMSO final concentration) and incubated for 72 h. The % viable cells was determined using the MTS/PMS cell proliferation kit (Promega) per the manufacturer's instructions. Cells treated with vehicle were normalized to 100% proliferation and values adjusted accordingly. HT29 (ATCC® HTB-38™) cells are human colorectal adenocarcinoma isolated from a 44 year old, female, Caucasian patient and purchased from ATCC in April of 2016. NCI-HT23 (ATCC® CRL-5800™) are non-small cell, human lung adenocarcinoma isolated from a 51 year old, male, Black patient and purchased from ATCC in April of 2016. No characterization or *Mycoplasma* testing was conducted on these cell lines following their purchase.

Anti-Proliferation Assay for UM-UC-3 Cells.

UM-UC-3 cells were grown to confluence and seeded at 2000 cells/well/0.1 mL in a 96-well plate and placed back in the incubator for 24 h. Compounds or vehicle were administered at the desired concentrations (1% DMSO final concentration) and incubated for 72 h. The % viable cells was determined using the Cell-Titer-Glo Luminescent Cell Viability Kit (Promega) per the manufacturer's instructions. Cells treated with vehicle were normalized to 100% proliferation and values adjusted accordingly. UM-UC-3 cells (ATCC® CRL-1749™) are bladder adenocarcinoma isolated from a male patient. No characterization or *Mycoplasma* testing was conducted on these cell lines following their purchase.

Western Blot for UM-UC-3 Cells.

UM-UC-3 cells were harvested in cold PBS and lysed with RIPA buffer: 50 mM Tris-HCl pH 7.5, 150 mM NaCl, containing 0.1% SDS, 1% Igepal, 1% sodium deoxycholate, protease and phosphatase inhibitor cocktail (Sigma-Aldrich, Inc., St. Louis, Mo.) by three freeze-thaw cycles using liquid nitrogen and a 37° C. water bath. Protein concentration was determined using DC Protein Assay (Bio-Rad Laboratories, Hercules, Calif.). Equal amounts of protein (20 μg) were loaded on a Novex E-PAGE™ 8% protein gel (Life Technologies), transferred to a nitrocellulose membrane by Novex iBlotR Gel Transfer system (Invitrogen, Carlsbad, Calif.), blocked in TBS-T containing 5% milk, and probed with primary antibodies (1:1000 dilution). Membranes were incubated with a horseradish peroxidase-conjugated secondary antibody, developed and visualized with Li-COR Odyssey Image system. All Western blots were probed for the loading control β-actin.

Western Blot for NCI-H23 Cells.

The NCI-H23 cells were harvested in cold PBS and lysed with mammalian protein extraction reagent (MPER, Pierce) lysis buffer containing protease and phosphatase inhibitors (Roche) on ice for 1 h. Lysates were clarified at 15,000 g for 20 min at 4° C. Protein concentrations were determined using the Qubit protein quantification assay kit per the manufacturer's instructions (ThermoFisher). Equal amounts of protein (2.5-20 μg) were electrophoresed under reducing conditions (10% acrylamide gel), transferred to a polyvinylidene fluoride membrane (PVDF), and immunoblotted with the corresponding specific antibodies. Membranes were incubated with an appropriate horseradish peroxidase-labeled secondary antibody, developed with a chemiluminescent substrate, and visualized. Data was first converted to 8-bit images in ImageJ, then Image Studio Lite Ver. 5.2 or Li-COR Odyssey Image Studio Ver 4.0 was used to perform densitometry. All proteins were normalized to actin then DMSO and reported as relative densities.

Co-Crystal Structure.

His6-tagged human Hsp90β N-terminal domain (amino acids 1-218) was cloned into a modified pET vector, overexpressed in *E. coli* BL21 DE3 cells and purified by Ni-NTA chromatography. The tag was cleaved using TEV protease followed by a second subtracting Ni-NTA chromatography to remove the TEV and the his-tag moiety. The flow through containing the cleaved protein was then concentrated and further purified via Superdex 200 size exclusion chromatography in 20 mM Tris-HCl, 150 mM NaCl, pH 7.8. Protein-inhibitor complexes were formed by mixing 15 mg/mL of Hsp90β NT with each inhibitor, 1.5-2.0 mM final drug concentrations, and incubating at 4° C. for one hour. Co-crystallization drops were set up at room temperature using 1:1 protein/drug to reservoir buffer of 30% PEG 8,000, 0.2 M sodium acetate, 0.1 sodium cacodylate pH 6.5. Crystals appeared in 1-2 days and were harvested in a cryo-buffer containing 20% glycerol added to reservoir buffer with each respective inhibitor at 2 mM.

Co-Crystal Structure Determination.

Data collection was done at the beamline 19-ID at the Advanced Photon Source (APS), Argonne National Laboratory. The structure was solved by molecular replacement method using Phaser (28) with the structure of Hsp90-beta (PDB code 1UYM) as the model template. PHENIX program (29) was used for the refinement, and Coot (30) was used for the iterative manual model building. Translation, libration and screw-rotation displacement (TLS) groups used in the refinement were defined by the TLMSD server (31). The current models are of good geometry and refinement statistics (Supplementary Table 1). All structure factors and pdbs were deposited with RCSB.org with pdb accession codes 5UC4, 5UCH, 5UCI and 5UCJ.

X-Ray Crystallography Study for $C_{19}H_{18}N_2O_3$, v87c(1).

A set of unique diffraction data (4438 0.5°-wide ω- or φ-scan frames with scan times of 3-6 seconds) were collected[S1] at 100(2)K for a single-domain crystal using monochromated CuKa radiation (l=1.54178 Å) on a Bruker Proteum Single Crystal Diffraction System equipped with dual CCD area detectors. Data collection utilized a Platinum 135 CCD detector with a crystal-to-detector distance of 8.0 cm. and Helios high-brilliance multilayer optics. X-rays were provided with a Bruker MicroStar microfocus Cu rotating anode x-ray source operating at 45 kV and 60 mA. The integrated data [S2] were corrected empirically for variable absorption effects using equivalent reflections. The Bruker software package SHELXTL was used to solve the structure using "direct methods" techniques. All stages of weighted full-matrix least-squares refinement were conducted using Fo2 data with the SHELXTL XL v2014 software package [S3]. All hydrogen atoms were located from a difference Fourier and refined in least square refinement cycles as independent isotropic atoms. All nonhydrogen atoms were included in the structural model with anisotropic thermal parameters. Final crystallographic details are summarized in Supplementary Table 1.

Results

Compound 1 was evaluated for Hsp90 inhibitory activity via a fluorescence polarization assay, which yielded a $K_d$ of 1.63 μM for Hsp90β and 3.21 μM for Hsp90α, (~2-fold selectivity).[35,36] Without being bound by theory, the 5-isopropyl appendage is thought to produce hydrophobic interactions with Val181 (FIG. 1A). Compound 2 was evaluated for Hsp90 inhibitory activity via a fluorescence polarization assay to determine binding affinity.[37] Compound 2 exhibited a $K_d$ of 2.27 μM and 0.97 μM against Hsp90α and Hsp90β, respectively, reflecting a ~2.5-fold selectivity for Hsp90β. Subsequently, variants of Compound 1 modified at the 4- and 5-positions, respectively, were synthesized to investigate the Hsp90 inhibitory activity (Tables 1A, 1B, and 2). Tables 1A, 1B, and 2 illustrate the binding affinity for these variants of Compound 1, including the 4-methylcyano (KUNB30), 4-methoxymethyl (3),—and 4-formyl (KUNB13) moieties.

Modifications to the 4-Position

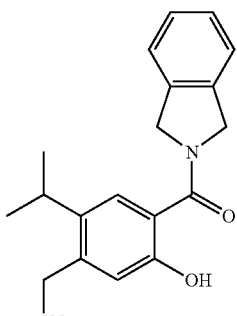

KUNB30

Hsp90a: 2.28 ± 0.12 mM
Hsp90b: 0.97 ± 0.03 mM

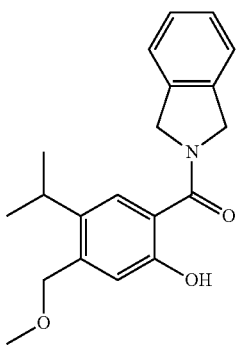

KUNB11

Hsp90a: >25 mM
Hsp90b: >25 mM

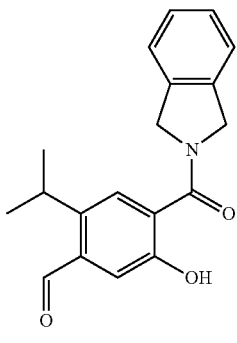

KUNB13

Hsp90a: 1.22 ± 0.01 mM
Hsp90b: 0.35 ± 0.13 mM

Figure 2:
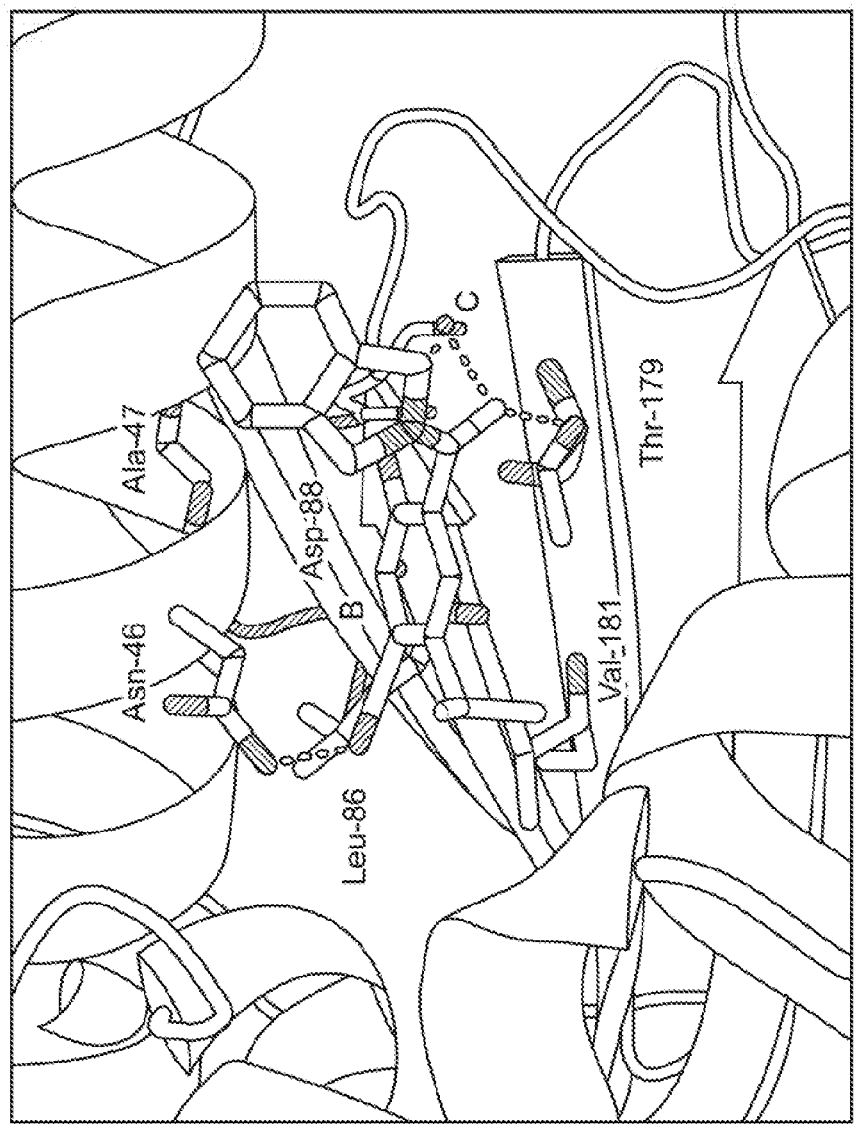
FIG. 2 illustrates the co-crystal structure of a compound of the present technology (KUNB13) bound to Hsp90β.

Compound 4, having the smaller 4-formyl group, showed both improved selectivity and affinity for Hsp90β ($K_d$=310 nM versus 1.55 µM, ~4-fold selectivity). The 4-methoxymethyl containing compound (3) did not bind either Hsp90 isoform at 10 µM. The binding modes of Compounds KUNB30 and KUNB13 were revealed by solution of the co-crystal structures bound to Hsp90β at 1.9 Å and 2.4 Å resolution, respectively. Examination of the co-crystal structures revealed an alternative binding mode for appendages at the 4-position, as the formyl and cyanomethyl appendages adopted a conformation wherein these moieties orient toward the back of the pocket. Asn46 showed a shift of 0.6 Å to accommodate the back pointing cyanomethyl group (FIG. 1A), which established a new binding mode and resulted in hydrogen bonding interactions between the nitrile and Asn46 upon displacement of the conserved water molecule, B. The carbonyl of Compound KUNB13 in the bound conformation exhibited hydrogen bonding interactions with Asn46, while simultaneously displacing conserved water molecule A (FIG. 2).

TABLE 1A

Summary of Compounds modified at the 4-position.

| X | $K_d$ Hsp90β (µM) | $K_d$ Hsp90α (µM) |
|---|---|---|
| OH | 1.97 ± 0.07 | 4.21 ± 0.62 |
| CH₃ | >50 | >50 |
| Cl | 25.15 ± 1.45 | >100 |
| Br | 0.73 ± 0.11 | 4.98 ± 0.97 |
| CH(CH₃)₂ | >100 | >100 |
| NH₂ | — | — |
| NHCH₃ | 23.19 ± 1.07 | >100 |
| OMe | >50 | >50 |
| CN | 0.97 ± 0.03 | 2.28 ± 0.12 |
| CONH₂ | 5.50 ± 0.51 | 15.21 ± 1.15 |

TABLE 1B $K_d$ values of Compounds modified at the 4-position and 5-position.

| R | X | $K_d$ Hsp90β (µM) | $K_d$ Hsp90α (µM) |
|---|---|---|---|
| 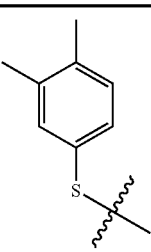 | OH | 2.86 ± 0.16 | 3.44 ± 0.18 |

TABLE 1B-continued $K_d$ values of Compounds modified at the 4-position and 5-position.

| R | X | $K_d$ Hsp90β (μM) | $K_d$ Hsp90α (μM) |
|---|---|---|---|
| 2-hydroxyphenylthio (HO-C6H4-S-) | OH | 2.68 ± 0.46 | 4.40 ± 0.08 |
| N-methyl-N-phenylamino | OH | 1.50 ± 0.1 | 5.05 ± 0.13 |
| isobutyl | OH | >50 | >50 |
| isobutyl | Br | 15.26 ± 1.24 | 37.87 ± 2.51 |
| sec-butyl | Br | 1.79 ± 0.21 | 5.88 ± 1.11 |
| sec-butyl | OH | 2.68 ± 0.46 | 4.40 ± 0.08 |
| Cl | OH | >50 | >50 |
| $CF_3$ | OH | 5.40 ± 0.15 | 6.35 ± 0.56 |
| $CH_2CH_3$ | OH | 1.01 ± 0.11 | 1.82 ± 0.28 |

TABLE 2

Summary of Compounds with 4-position modifications.

| X | $K_d$ Hsp90β (μM) | $K_d$ Hsp90α (μM) |
|---|---|---|
| $NH(CH_2CH_3)$ | >100 | >100 |
| $N(CH_2CH_3)_2$ | >100 | >100 |
| NHCHO | 30.18 ± 4.66 | 7.59 ± 0.56 |
| $NH(CO)CH_3$ | >100 | >100 |
| NH(CN) | 0.42 ± 0.05 | 0.18 ± 0.05 |
| CHO | 0.24 ± 0.08 | 1.21 ± 0.12 |
| $NH_2$ | 0.71 ± 013 | 0.46 ± 0.22 |
| $C=CF_2$ | 4.21 ± 0.08 | 5.18 ± 0.29 |
| $CH(OH)CH_3$ | 4.87 ± 0.11 | 4.07 ± 0.14 |
| $CONH_2$ | 0.37 | 2.3 |

Figure 3A:
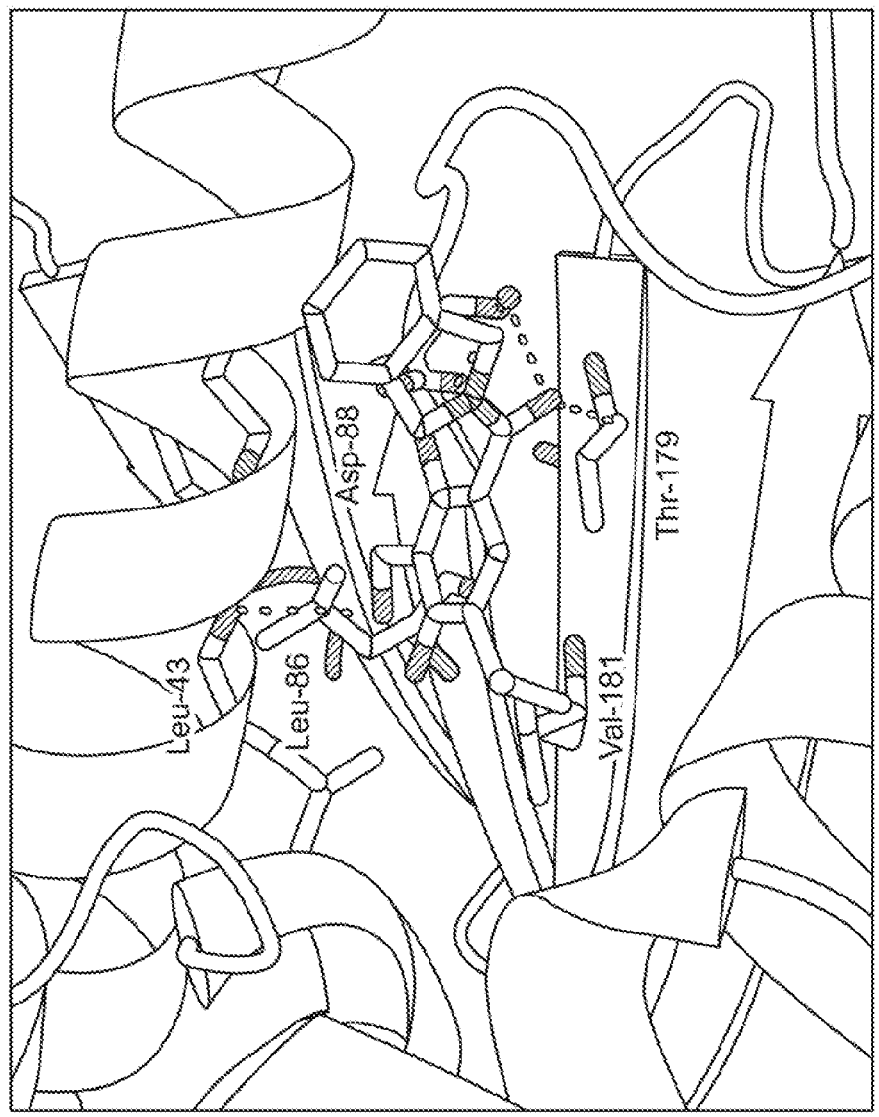
FIG. 3A illustrates the co-crystal structure of a compound of the present technology (KUNB14) bound to Hsp90β.

Compound KUNB14 was evaluated using the fluorescence polarization assay described above. As illustrated in Table 3, Compound KUNB14 exhibited a $K_d$ of 4.27 μM for Hsp90β. More importantly, it exhibited a selectivity (>25-fold) over the other isoforms. As illustrated in FIG. 3A, the co-crystal structure of Compound KUNB14 bound to Hsp90β was solved showing that the benzyl alcohol displaced conserved water molecules A and B and participated in hydrogen bonding interactions with the backbone of Leu43.

TABLE 3

Summary of Exemplary 3-position modifications

| Compound Ref. | X | $K_d$ Hsp90β (μM) | $K_d$ Hsp90α (μM) | Selectivity |
|---|---|---|---|---|
| KUNB1 | CHO | ≥100 | ≥100 | |
| KUNB4 | $CH_2NH_2$ | ≥100 | ≥100 | |
|  | $CH_3$ | ≥100 | ≥100 | |
| KUNB5 | $CH_2CH_2CH_3$ | 6.3 | ≥75 | |
| KUNB7 | $CH_2CH_2OH$ | ≥100 | ≥100 | |
| KUNB3 | $CH_2CH_3$ | 3.31 | ≥100 | ≥30 |
| KUNB2 | $CHCH_2$ | 5.24 | ≥100 | ≥19 |
| KUNB6 | $CH_2CHCH_2$ | ≥100 | ≥100 | |
| KUNB14 | $CH_2OH$ | 4.27 | ≥100 | ≥25 |

Figure 3B:
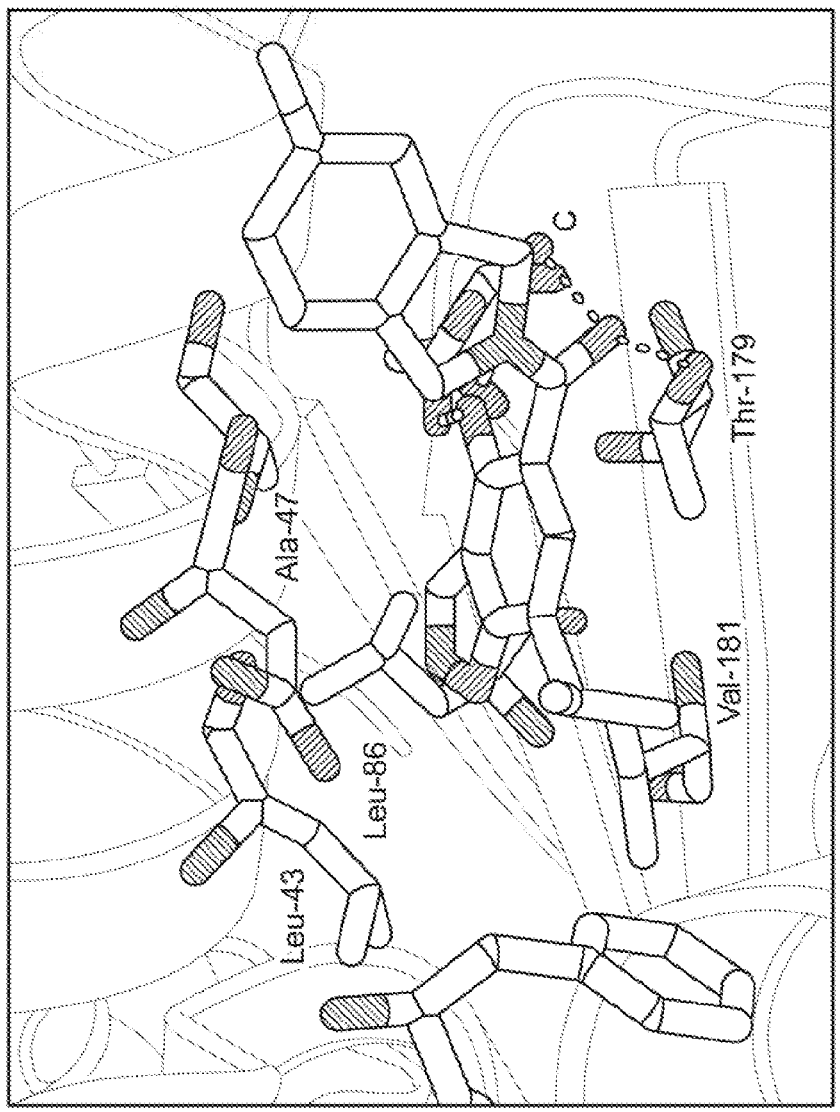
FIG. 3B illustrates the co-crystal structure of a compound of the present technology bound to Hsp90β.

Ring constrained variants at the 3- and 4-positions were successfully synthesized to evaluate binding affinity to Hsp90 (Table 4). Compound KUNB31a and the fluoroisoindoline analog KUNB31b exhibited a $K_d$ of 180 nM against Hsp90β, while also exhibiting ~50 fold selectivity over Hsp90α and Grp94. As provided in Table 3, $K_d$ values for additional constrained variants exhibited improvements in affinity for Hsp90β and Hsp90α, while exhibiting selectivity over Hsp90α and Grp94 from 1.6-85 fold. The co-crystal structure of KUNB31b showed both water molecules A and B were displaced upon binding (FIG. 3B).

TABLE 4

Summary of Exemplary 3-& 4-position modifications

| Compound Ref. | R²—R¹ | $K_d$ Hsp90β (μM) | $K_d$ Hsp90α (μM) | Selectivity |
|---|---|---|---|---|
| KUNB31a | —(CH=N—O)— | 0.18 | 3.55 | 53 |
| KUNB22 | —(CH₂CH₂C(O))— | 0.11 | 9.3 | 85 |
| KUNB17 | —(CHCHO)— | 0.72 | ≥10 | ≥14 |
|  | —(CH=N—NH)— | ≥50 | ≥50 |  |
| KUNB18 | —(NH—N=CH)— | 3.71 | 82.5 | 22 |
| KUNB19 | —(N=CH—NH)— | 6.3 | ≥100 | 1.6 |
| KUNB20 | —(N=N—NH)— | ≥100 | ≥100 |  |
| KUNB28 | —(CH₂CH(CH₃)C(O))— | 0.295 | ≥10 | ≥34 |
| KUNB23 | —(CH₂CH(C₂H₅)C(O))— | 0.58 | ≥10 | ≥17 |
| KUNB24 | —(CH₂CH(C₃H₇)C(O))— | 2.7 | ≥100 | ≥37 |
| KUNB25 | —(CH₂NHC(O))— | 0.33 | ≥10 | ≥30 |
| KUNB26 | —(CH₂N(C₂H₅)C(O))— | 0.53 | ≥10 | ≥19 |

Figure 4A:
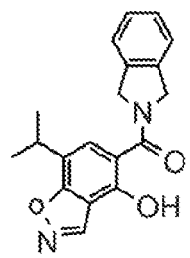
FIG. 4A illustrates the anti-proliferation values of a compound of the present technology (KUNB31a) in immortalized cancerous (NCI-H23, UC3, HT29) and non-cancerous (HEK-293) cells.

Once the Hsp90β-selective inhibitor KUNB31a was identified, cellular studies according to the procedure described above were performed to evaluate the effect of Hsp90β-inhibition on cancer cell lines. The anti-proliferative activity manifested by KUNB31a was evaluated against the cancer cell lines NCI-H23 (non-small cell lung cancer), UC3 (bladder cancer), HT-29 (colon adenocarcinoma) cells, as well as non-cancerous HEK 293 (human embryonic kidney) cells. As shown in FIG. 4A and Table 5, KUNB31a exhibited an $IC_{50}$ of 6.74±1.10 μM, 3.01±0.56 μM, and 3.72±0.34 μM against NCI H23, UC3, and HT-29 cancer cell lines, respectively, while requiring more than 100 μM against HEK-293 cells. Table 4 illustrates the anti-proliferative activity against NCI-H23, MCF-7, and SkBr3 for exemplary compounds of the present technology.

TABLE 4

Anti-proliferation activities of Certain Compounds of Present Technology

| Compound | $IC_{50}$, NCI-H23 (μM) | $IC_{50}$, MCF-7 (μM) | $IC_{50}$, SkBr3 (μM) |
|---|---|---|---|
| [structure 1] Hsp90a: 9.55 ± 1.08 mM; Hsp90b: 0.18 ± 0.01 mM; Grp94: 8.48 ± 0.97 mM | 6.75 ± 1.1 | 28.27 ± 1.47 | 38.21 ± 2.75 |
| [structure 2] Hsp90a: 18.17 ± 0.25 mM; Hsp90b: 0.44 ± 0.09 mM | 5.76 | 16.63 | — |
| [structure 3] Hsp90a: >100 mM; Hsp90b: 4.27 ± 0.19 mM; Grp94: >100 mM | 3.90 ± 0.33 | 13.67 ± 1.46 | 9.13 ± 1.03 |

TABLE 4-continued

Anti-proliferation activities of Certain Compounds of Present Technology

| Compound | IC$_{50}$, NCI-H23 (μM) | IC$_{50}$, MCF-7 (μM) | IC$_{50}$, SkBr3 (μM) |
|---|---|---|---|
| 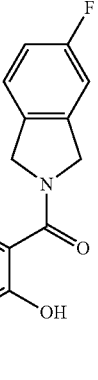 Hsp90a: 56.52 ± 18.62 mM<br>Hsp90b: 2.75 ± 0.20 mM | 2.13 ± 0.7 | 13.18 | — |
| 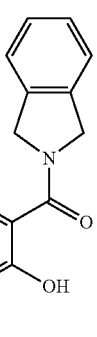 Hsp90a: 82.5 ± 7.6 mM<br>Hsp90b: 3.71 ± 0.12 mM<br>Grp94: >100 | 13.67 | 19.14 | 29.7 |
| 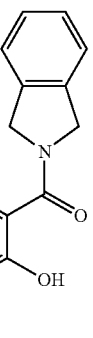 Hsp90a: 84.16 ± 4.47 mM<br>Hsp90b: 6.73 ± 2.67 mM | 13.43 | — | 23.6 |

Figure 4B:
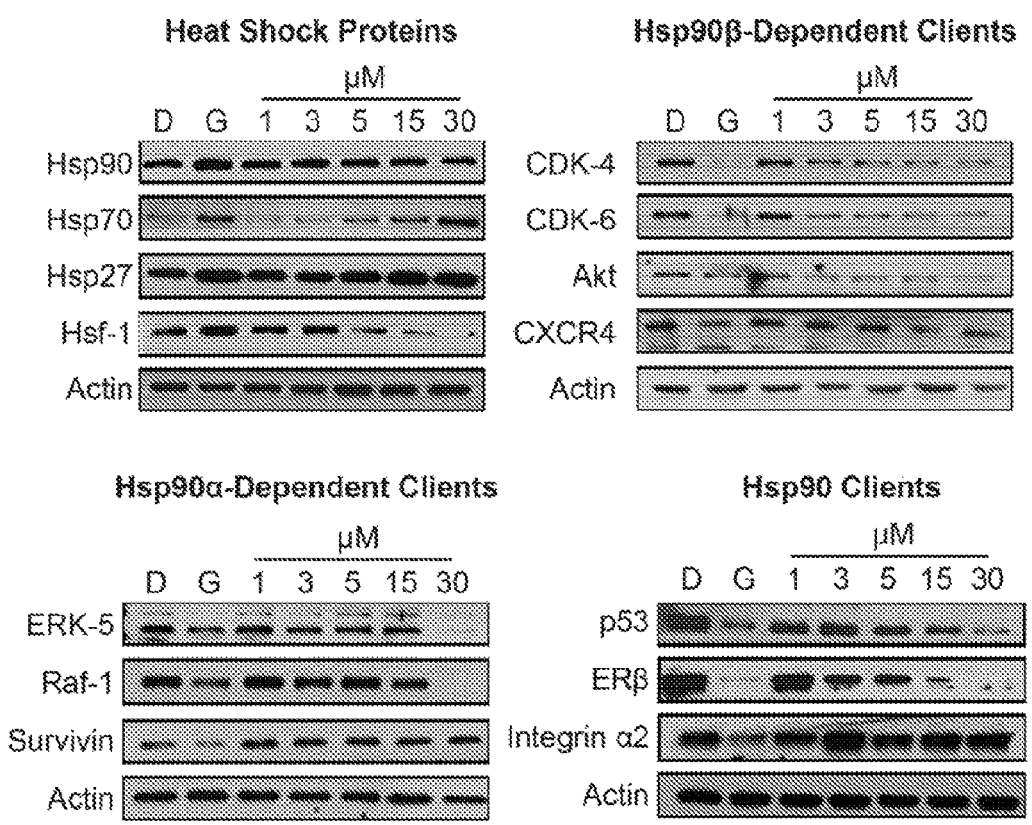
FIG. 4B illustrates the representative Western blot analyses after 24 h treatment with a compound of the present technology (KUNB31a) in HT29 cells with relative densities, in a dose dependent manor (at concentrations of 1, 3, 5, 15 and 30 μM).

NCI-H23 and HT29 cells were evaluated via Western blot analyses of known Hsp90α- and Hsp90β-dependent client proteins following treatment with KUNB31a for 24 h (FIG. 4B). The levels of both kinase and non-kinase Hsp90 clients were also assessed via Western blot analysis. Known Hsp90 clients EGFR, HER2, CDK4, CDK6, CXCR$_4$, Akt-1, c-Raf, Survivin, ERK-5 and Integrin α2 were analyzed following the administration of KUNB31a to HT29 (colon adenocarcinoma grade II) cells. After a 24 h incubation with KUNB31a, Hsp90β-dependent client proteins were reduced at concentrations that mirrored the cellular IC$_{50}$ value, clearly linking cell viability to Hsp90β inhibition. Negative and positive controls of FIG. 4B include DMSO (D), and geldanamycin (G) at 500 nM, respectively. In contrast, the level of Hsp90α-dependent clients, Raf-1, ERK-5, and survivin remained unaffected until higher concentrations. No client protein degradation was observed with Grp-94-dependent client Integrin α2. Levels of clients like HER-2 and EGFR that do not appear to be isoform dependent, decrease around 5 μM (FIGS. 4B and 4C). Interestingly, levels of both Hsf-1 and Hsp90 decreased, which showed that selective-inhibition of Hsp90β does not increase Hsp90 levels. Levels of Hsp27 and Hsp70 were induced at higher concentrations.

The results presented herein provide the evidence that selective inhibition of Hsp90β by exemplary compounds of the present technology alters the heat shock response and prevents Hsp90 induction, which represents a serious detriment associated with pan-inhibitors of Hsp90. Furthermore, the compounds of the present technology may be used to validate isoform-selective inhibition as a viable approach toward cancer treatment while enabling the identification of specific roles played by Hsp90β in other diseases. The compounds of the present technology demonstrate N-terminal isoform-selective inhibition of Hsp90β and exhibited low micromolar anti-proliferative activity. For example, compound KUNB31a induced the degradation of select Hsp90β-dependent clients without concomitant induction of Hsp90 levels.

In-Vivo Model for Cancer:

A standard xenograft mouse model will be used for studying the in-vivo effects of compounds of the present technology on metastasis and proliferation of a tumor. It is expected that mice receiving administration of compounds of the present technology will exhibit a reduction in metastasis and/or reduction in proliferation of the tumor as compared to control mice receiving vehicle.

REFERENCES

1. Sreedhar, A. S., Kalmar, E., Csermely, P. & Shen, Y. F. Hsp90 isoforms: functions, expression and clinical importance. FEBS Lett. 562, 11-15 (2004).
2. Chen, B., Piel, W. H., Gui, L., Bruford, E. & Monteiro, A. The HSP90 family of genes in the human genome: insights into their divergence and evolution. Genomics 86, 627-637, doi:10.1016/j.ygeno.2005.08.012 (2005).
3. Garg, G., Khandelwal, A. & Blagg, B. S. Anticancer Inhibitors of Hsp90 Function: Beyond the Usual Suspects. Adv Cancer Res 129, 51-88, doi:10.1016/bs.acr.2015.12.001 (2016).
4. Whitesell, L. & Lindquist, S. L. HSP90 and the Chaperoning of Cancer. Nature Reviews Cancer 5, 761-772, doi:10.1038/nrc1716 (2005).
5. Karagoz, G. E. & Rudiger, S. G. Hsp90 interaction with clients. Trends Biochem. Sci 40, 117-125, doi:10.1016/j.tibs.2014.12.002 (2015).
6. Röhl, A., Rohrber, J. & Buchner, J. The Chaperone Hsp90: Changing Partners for Demanding Clients. Trends Biochem. Sci 38, 253-262, doi:10.1016/j.tibs.2013.02.003 (2013).
7. Zuehlke, A. & Johnson, J. L. Hsp90 and co-chaperones twist the functions of diverse client proteins. Biopolymers 93, 211-217, doi:10.1002/bip.21292 (2010).
8. Vaughan, C. K., Neckers, L. & Piper, P. W. Understanding of the Hsp90 Molecular Chaperone Reaches New 9. Chiosis, G., Dickey, C. A. & Johnson, J. L. A Global View of Hsp90 Functions. Nature structural & molecular biology 20, 1-4, doi:10.1038/nsmb.2481 (2013).
10. Miyata, Y., Nakamoto, H. & Neckers, L. The therapeutic target Hsp90 and cancer hallmarks. Current pharmaceutical design 19, 347-365 (2013).
11. Trepel, J., Mollapour, M., Giaccone, G. & Neckers, L. Targeting the Dynamic HSP90 Complex in Cancer. Nature Reviews Cancer 10, 537-549, doi:10.1038/nrc2887 (2010).
12. Neckers, L. & Trepel, J. B. Stressing the development of small molecules targeting HSP90. Clinical cancer research: an official journal of the American Association for Cancer Research 20, 275-277, doi:10.1158/1078-0432.CCR-13-2571 (2014).
13. Travers, J., Sharp, S. & Workman, P. HSP90 Inhibition: Two-Pronged Exploitation of Cancer Dependencies. Drug Discovery Today 17, 242-252, doi:10.1016/j.drudis.2011.12.021 (2012).
14. Bhat, R., Tummalapalli, S. R. & Rotella, D. P. Progress in the discovery and development of heat shock protein 90 (hsp90) inhibitors. J. Med. Chem. 57, 8718-8728, doi: 10.1021/jm500823a (2014).
15. Barrott, J. J. & Haystead, T. A. J. Hsp90, an Unlikely Ally in the War on Cancer. The FEBS journal 280, 1381-1396, doi:10.1111/febs.12147 (2013).
16. Jhaveri, K., Taldone, T., Modi, S. & Chiosis, G. Advances in the clinical development of heat shock protein 90 (Hsp90) inhibitors in cancers. Biochim. Biophys. Acta 1823, 742-755, doi:10.1016/j.bbamcr.2011.10.008 (2012).
17. Khandelwal, A., Crowley, V. M. & Blagg, B. S. Natural Product Inspired N-Terminal Hsp90 Inhibitors: From Bench to Bedside? Medicinal research reviews 36, 92-118, doi:10.1002/med.21351 (2016).
18. Neckers, L. & Workman, P. Hsp90 molecular chaperone inhibitors: are we there yet? Clinical cancer research: an official journal of the American Association for Cancer Research 18, 64-76, doi:10.1158/1078-0432.CCR-11-1000 (2012).
19. Garcia-Carbonero, R., Carnero, A. & Paz-Ares, L. Inhibition of Hsp90 molecular chaperones: moving into the clinic. Lancet Oncology 14, e358-e369 (2013).
20. Biamonte, M. A. et al. Heat shock protein 90: inhibitors in clinical trials. J. Med. Chem. 53, 3-17, doi:10.1021/jm9004708 (2010).
21. Hong, D. S. et al. Targeting the molecular chaperone heat shock protein 90 (HSP90): lessons learned and future directions. Cancer treatment reviews 39, 375-387, doi:10.1016/j.ctrv.2012.10.001 (2013).
22. Powers, M. V. & Workman, P. Inhibitors of the heat shock response: biology and pharmacology. FEBS Lett. 581, 3758-3769, doi:10.1016/j.febslet.2007.05.040 (2007).
23. Peterson, L. B., Eskew, J. D., Vielhauer, G. A. & Blagg, B. S. The hERG channel is dependent upon the Hsp90alpha isoform for maturation and trafficking. Mol Pharm 9, 1841-1846, doi:10.1021/mp300138n (2012).
24. Bagatell, R. et al. Induction of a heat shock factor 1-dependent stress response alters the cytotoxic activity of hsp90-binding agents. Clinical cancer research: an official journal of the American Association for Cancer Research 6, 3312-3318 (2000).
25. Jolly, C. & Morimoto, R. I. Role of the heat shock response and molecular chaperones in oncogenesis and cell death. J Natl Cancer Inst 92, 1564-1572 (2000).
26. Butler, L. M., Ferraldeschi, R., Armstrong, H. K., Centenera, M. M. & Workman, P. Maximizing the Therapeutic Potential of HSP90 Inhibitors. Mol Cancer Res 13, 1445-1451, doi:10.1158/1541-7786.MCR-15-0234 (2015).
27. Panaretou, B. et al. ATP binding and hydrolysis are essential to the function of the Hsp90 molecular chaperone in vivo. EMBO J. 17, 4829-4836, doi:10.1093/emboj/17.16.4829 (1998).
28. Prince, T. L. et al. Client Proteins and Small Molecule Inhibitors Display Distinct Binding Preferences for Constitutive and Stress-Induced HSP90 Isoforms and Their Conformationally Restricted Mutants. PloS one 10, e0141786, doi:10.1371/journal.pone.0141786 (2015).
29. Zubriene, A. et al. Thermodynamics of radicicol binding to human Hsp90 alpha and beta isoforms. Biophys. Chem. 152, 153-163, doi:10.1016/j.bpc.2010.09.003 (2010).
30. Gewirth, D. T. Paralog Specific Hsp90 Inhibitors—A Brief History and a Bright Future. Curr. Top. Med. Chem. 16, 2779-2791 (2016).
31. Lee, C. et al. Development of a mitochondria-targeted Hsp90 inhibitor based on the crystal structures of human TRAP1. J. Am. Chem. Soc. 137, 4358-4367, doi:10.1021/ja511893n (2015).
32. Patel, P. D. et al. Paralog-selective Hsp90 inhibitors define tumor-specific regulation of HER2. Nature Chemical Biology 9, 677-684, doi:10.1038/nchembio.1335 (2013).
33. Duerfeldt, A. S. et al. Development of a Grp94 inhibitor. Journal of the American Chemical Society 134, 9796-9804, doi:10.1021/ja303477g (2012).
34. Crowley, V. M. et al. Development of Glucose Regulated Protein 94-Selective Inhibitors Based on the BnIm and Radamide Scaffold. J Med Chem 59, 3471-3488, doi: 10.1021/acs.jmedchem.6b00085 (2016).
35. Murray, C. W. et al. Fragment-based drug discovery applied to Hsp90. Discovery of two lead series with high ligand efficiency. J. Med. Chem. 53, 5942-5955, doi: 10.1021/jm100059d (2010).
36. Woodhead, A. J. et al. Discovery of (2,4-dihydroxy-5-isopropylphenyl)-[5-(4-methylpiperazin-1-ylmethyl)-1,3-dihydroisoindol-2-yl]methanone (AT13387), a novel inhibitor of the molecular chaperone Hsp90 by fragment based drug design. J. Med. Chem. 53, 5956-5969, doi: 10.1021/jm100060b (2010).
37. Kim, J. et al. Development of a fluorescence polarization assay for the molecular chaperone Hsp90. Journal of biomolecular screening 9, 375-381, doi:10.1177/1087057104265995 (2004).
38. Didelot, C. et al. Interaction of heat-shock protein 90beta isoform (HSP90beta) with cellular inhibitor of apoptosis 1 (c-IAP1) is required for cell differentiation. Cell death and differentiation, doi:10.1038/sj.cdd.4402320 (2008).
39. Liu, W. et al. KU675, a Concomitant Heat-Shock Protein Inhibitor of Hsp90 and Hsc70 that Manifests Isoform Selectivity for Hsp90alpha in Prostate Cancer Cells. Mol. Pharmacol. 88, 121-130, doi:10.1124/mol.114.097303 (2015).
42. Hobbs, A.; Wittinghofer, A.; Der, C., Selective Targeting of the KRAS G12C Mutant: Kicking KRAS When It's Down. Cancer Cell. 29, 251-253, doi.org/10.1016/j.ccell.2016.02.015 (2016).

While certain embodiments have been illustrated and described, a person with ordinary skill in the art, after reading the foregoing specification, can effect changes, substitutions of equivalents and other types of alterations to the compounds of the present technology or salts, pharmaceutical compositions, derivatives, prodrugs, metabolites, tautomers or racemic mixtures thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present technology may include, but is not limited to, the features and combinations of features recited in the following lettered paragraphs, it being understood that the following paragraphs should not be interpreted as limiting the scope of the claims as appended hereto or mandating that all such features must necessarily be included in such claims:

A. A compound according to Formula I

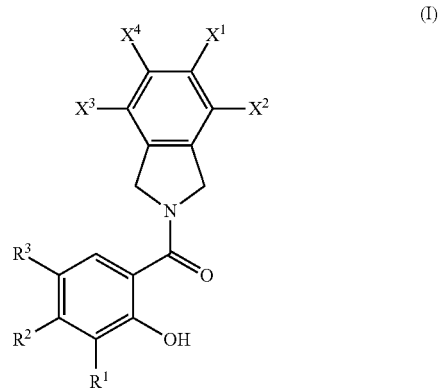

or a pharmaceutically acceptable salt and/or solvate thereof, wherein $X^1$, $X^2$, $X^3$, and $X^4$ are each independently selected from H, F, Cl, Br, I, sulfoxide, sulfone, nitro, pentafluorosulfanyl, C(O)OH, amide, or ester;

$R^1$ is H, OH, $C_1$-$C_3$ alkyl, $C_2$-$C_4$ alkenyl, or —$CH_2OH$;

$R^2$ is $CH_2$—$X^5$ or OH, where $X^5$ is OH, F, Cl, Br, CN, —C(O)—$NR^4R^5$, —$NR^6$—C(O)H, —$NR^7$—C(O)-alkyl, C(O)H, C(O)OH, sulfonamido, sulfoxide, sulfone, or $S(O)_2OH$;

or $R^1$ and $R^2$ together are (moving in the direction from $R^2$ to $R^1$) —C($X^6$)—$CH_2$—, —C($X^7$)—CH($R^8$)—CH($R^9$)—, —C($X^8$)—N($R^{10}$)—CH($R^{11}$)—, —C($X^9$)—CH($R^{12}$)—CH($R^{13}$)—CH($R^{14}$)—, —C($X^{10}$)—N($R^{15}$)—CH($R^{16}$)—CH($R^{17}$)—, —O—CH=CH—, —O—N=CH—, —NH—CH=N—, or —CH=N—NH—;

$X^6$, $X^7$, $X^8$, $X^9$, and $X^{10}$ are each independently selected from O, $CH_2$, and $CF_2$;

$R^3$ is alkyl, —CH($CH_3$)$_2$, $CF_3$, Br, sulfonamido, sulfoxide, sulfone, nitro, pentafluorosulfanyl, C(O)OH, amide, or ester;

$R^4$, $R^5$, $R^6$, and $R^7$ are each independently H or alkyl;

$R^8$, $R^9$, $R^{11}$, $R^{12}$, $R^{13}$, $R^{14}$, $R^{16}$, and $R^{17}$ are each independently selected from H, $C_1$-$C_3$ alkyl, F, Cl, Br, I, or $CF_3$; and $R^{10}$ and $R^{15}$ are each independently H or $C_1$-$C_3$ alkyl.

B. The compound of Paragraph A, wherein the compound is of Formula II

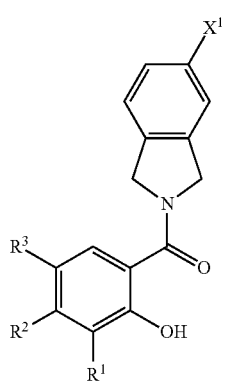

(II)

or a pharmaceutically acceptable salt and/or solvate thereof.

C. The compound of Paragraph A or Paragraph B, wherein $R^1$ is H, OH, methyl, ethyl, propyl, vinyl, or —$CH_2OH$.

D. The compound of Paragraph A or Paragraph B, wherein $R^2$ is $CH_2$—$X^5$ or OH, where $X^5$ is OH, F, CN, —C(O)—$NR^4R^5$, —$NR^6$—C(O)H, —$NR^7$—C(O)-alkyl, C(O)H, C(O)OH, or $S(O)_2OH$.

E. The compound of Paragraph A, wherein the compound is of Formula III

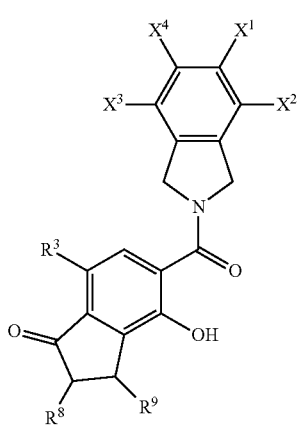

(III)

or a pharmaceutically acceptable salt and/or solvate thereof.

F. The compound of Paragraph A, wherein the compound is of Formula IV

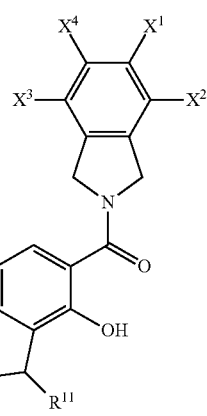

(IV)

or a pharmaceutically acceptable salt and/or solvate thereof.

G. The compound of any one of Paragraphs A-F, wherein $R^3$ is alkyl, —$CH(CH_3)_2$, $CF_3$, Br, sulfoxide, sulfone, nitro, pentafluorosulfanyl, C(O)OH, amide, or ester.

H. The compound of any one of Paragraphs A-G, wherein $X^1$ is H, F, Cl, Br, or I.

I. The compound of any one of Paragraphs A-H, wherein $X^5$ is OH, F, Cl, Br, CN, —C(O)—$NH_2$, —NH—C(O)H, —NH—C(O)-alkyl, —C(O)H, or —C(O)OH.

J. A composition comprising a compound of any one of Paragraphs A-I and a pharmaceutically acceptable carrier.

K. A pharmaceutical composition comprising an effective amount of a compound of any one of Paragraphs A-I and a pharmaceutically acceptable carrier, wherein the effective amount is effective for treating non-small cell lung cancer, bladder cancer, or colon cancer.

L. The pharmaceutical composition of Paragraph K, wherein the effective amount is effective for treating non-small cell lung cancer, bladder cancer, or colon adenocarcinoma.

M. The pharmaceutical composition of Paragraph K or Paragraph L, wherein the pharmaceutical composition is packaged in unit dosage form.

N. A method comprising administering a compound of any one of Paragraphs A-I to a subject.

O. The method of Paragraph N, wherein the subject is suffering from non-small cell lung cancer, bladder cancer, or colon cancer (such as colon adenocarcinoma).

P. The method of Paragraph N or Paragraph O, wherein the method comprises administering an effective amount of the compound for treating non-small cell lung cancer, bladder cancer, or colon cancer (such as colon adenocarcinoma).

Q. The method of Paragraph P, wherein administering the effective amount of the compound treats the subject.

R. The method of any one of Paragraphs N-Q, wherein the subject is not human.

S. The method of any one of Paragraphs N-Q, wherein the subject is human.

T. A method for inhibiting cell motility of a cancer cell, the method comprising contacting the cancer cell with a compound of any one of Paragraphs A-I.

U. The method of Paragraph T, wherein the cancer cell is a non-small cell lung cancer cell, a bladder cancer cell, or a colon cancer cell (such as a colon adenocarcinoma cell).

V. The method of Paragraph T or Paragraph U, wherein the method comprises contacting the cancer cell with an effective amount of the compound.

W. The method of Paragraph V, wherein contacting the cancer cell with the effective amount of the compound inhibits cell motility of the cancer cell.

X. The method of any one of Paragraphs T-W, wherein the cancer cell is not within a subject.

Y. A method of selectively inhibiting Hsp90β over Hsp90α, wherein the method comprises administering a compound of any one of Paragraphs A-I to a cancer cell and/or to a subject.

Z. The method of Paragraph Y, wherein administering the compound comprises administering in vitro or in vivo.

AA. The method of Paragraph Y or Paragraph Z, wherein administering the compound comprises administering to a subject, such as a subject suffering from non-small cell lung cancer, bladder cancer, or colon cancer (such as colon adenocarcinoma).

AB. The method of Paragraph Y or Paragraph Z, wherein administering the compound does not comprise administering to a subject.

AC. The method of any one of Paragraphs Y, Z, and AB, wherein the cancer cell is not within a subject.

AD. The method of any one of Paragraphs Z-AC, wherein administering the compound to the cancer cell and/or to the subject selectively inhibits Hsp90β over Hsp90α.

AE. The method of any one of Paragraphs Z-AD, wherein the compound exhibits a selectivity ratio for Hsp90β over Hsp90α of at least about 2:1.

Other embodiments are set forth in the following claims, along with the full scope of equivalents to which such claims are entitled.

What is claimed is:

1. A compound according to Formula I

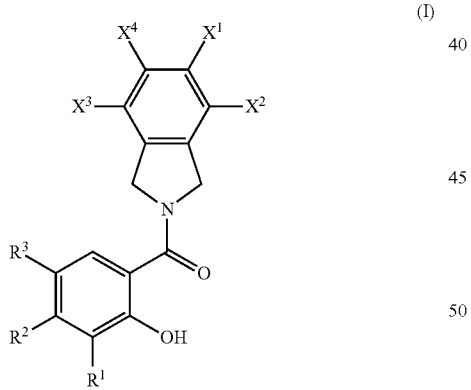

(I)

or one or both of a pharmaceutically acceptable salt thereof or a solvate thereof, wherein $X^1$, $X^2$, $X^3$, and $X^4$ are each independently selected from H, F, Cl, Br, I, —S(O)$R^{81}$, —SO$_2$$R^{82}$, nitro, pentafluorosulfanyl, C(O)OH, amide, or ester;

$R^1$ is OH, ethyl, propyl, $C_2$-$C_4$ alkenyl, or —CH$_2$OH;

$R^2$ is CH$_2$—$X^5$ or OH, where $X^5$ is OH, F, Cl, Br, CN, —C(O)—NR$^4$R$^5$, —NR$^6$—C(O)H, —NR$^7$—C(O)-alkyl, C(O)H, C(O)OH, sulfonamido, —S(O)$R^{81}$, —SO$_2$$R^{82}$, or S(O)$_2$OH;

or $R^1$ and $R^2$ together are (moving in the direction from $R^2$ to $R^1$) —C($X^6$)—CH$_2$—, —C($X^7$)—CH($R^8$)—CH($R^9$)—, —C($X^8$)—N($R^{10}$)—CH($R^{11}$)—, —C($X^9$)—CH($R^{12}$)—CH($R^{13}$)—CH($R^{14}$)—, —C($X^{10}$)—N($R^{15}$)—CH($R^{16}$)—CH($R^{17}$)—, —O—CH=CH—, —O—N=CH—, —NH—CH=N—, or —CH=N—NH—;

$X^6$, $X^7$, $X^8$, $X^9$, and $X^{10}$ are each independently selected from O, CH$_2$, and CF$_2$;

$R^3$ is alkyl, —CH(CH$_3$)$_2$, CF$_3$, Br, sulfonamido, —S(O)$R^{81}$, —SO$_2$$R^{82}$, nitro, pentafluorosulfanyl, C(O)OH, amide, or ester;

$R^4$, $R^5$, $R^6$, and $R^7$ are each independently H or alkyl;

$R^8$, $R^9$, $R^{11}$, $R^{12}$, $R^{13}$, $R^{14}$, $R^{16}$, and $R^{17}$ are each independently selected from H, $C_1$-$C_3$ alkyl, F, Cl, Br, I, or CF$_3$;

$R^{10}$ and $R^{15}$ are each independently H or $C_1$-$C_3$ alkyl;

$R^{81}$ is independently at each occurrence alkyl, cycloalkyl, alkenyl, alkynyl, aryl, aralkyl, heterocyclyl or heterocyclylalkyl; and $R^{82}$ is independently at each occurrence alkyl, cycloalkyl, alkenyl, alkynyl, aryl, aralkyl, heterocyclyl or heterocyclylalkyl.

2. The compound of claim 1, wherein the compound is of Formula II

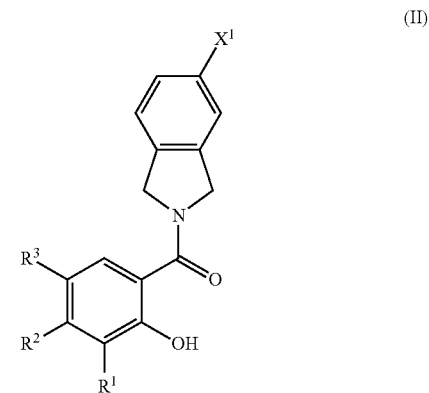

(II)

or one or both of a pharmaceutically acceptable salt thereof or a solvate thereof.

3. The compound of claim 1, wherein
$R^1$ is OH, ethyl, propyl, vinyl, or —CH$_2$OH.

4. The compound of claim 1, wherein the compound is of Formula III

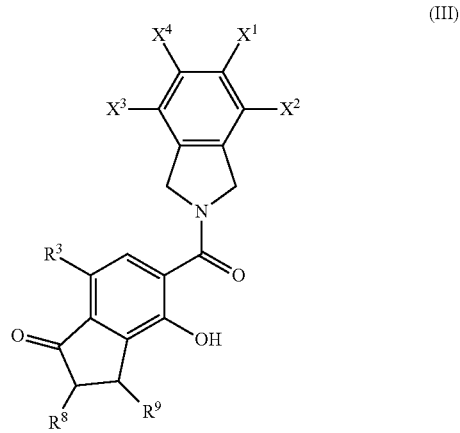

(III)

5. The compound of claim 1, wherein the compound is of Formula IV

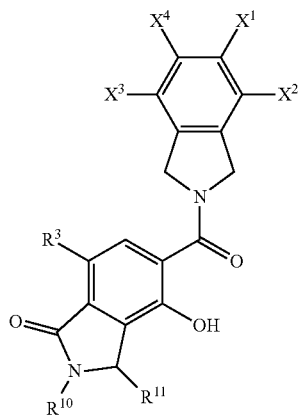

(IV)

or one or both of a pharmaceutically acceptable salt thereof or a solvate thereof.

6. The compound of claim 1, wherein $R^3$ is alkyl, —CH(CH$_3$)$_2$, CF$_3$, Br, —S(O)R$^{81}$, —SO$_2$R$^{82}$, nitro, pentafluorosulfanyl, C(O)OH, amide, or ester.

7. The compound of claim 1, wherein $X^1$ is H, F, Cl, Br, or I.

8. The compound of claim 1, wherein $X^5$ is OH, F, Cl, Br, CN, —C(O)—NH$_2$, —NH—C(O)H, —NH—C(O)-alkyl, —C(O)H, or —C(O)OH.

9. A composition comprising a compound of claim 1 and a pharmaceutically acceptable carrier.

10. A pharmaceutical composition comprising an effective amount of a compound of claim 1 and a pharmaceutically acceptable carrier, wherein the effective amount is effective for treating non-small cell lung cancer, bladder cancer, or colon cancer.

11. A method for inhibiting cell motility of a cancer cell, the method comprising contacting the cancer cell with a compound of claim 1.

12. A method of selectively inhibiting Hsp90β over Hsp90α, wherein the method comprises administering a compound of claim 1 to a cancer cell or to a subject.

13. The method of claim 12, wherein the compound exhibits a selectivity ratio for Hsp90β over Hsp90α of at least about 2:1.

14. A compound according to Formula I

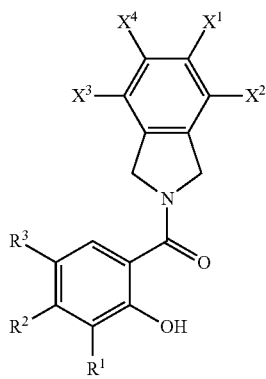

(I)

or one or both of a pharmaceutically acceptable salt thereof or a solvate thereof, wherein $X^1$, $X^2$, $X^3$, and $X^4$ are each independently selected from H, F, Cl, Br, I, —S(O)R$^{81}$, —SO$_2$R$^{82}$, nitro, pentafluorosulfanyl, C(O)OH, amide, or ester;

$R^1$ is H, OH, C$_1$-C$_3$ alkyl, C$_2$-C$_4$ alkenyl, or —CH$_2$OH;

$R^2$ is CH$_2$—X$^5$, where X$^5$ is OH, F, Cl, Br, CN, —C(O)—NR$^4$R$^5$, —NR$^6$—C(O)H, —NR$^7$—C(O)-alkyl, C(O)H, C(O)OH, sulfonamido, —S(O)R$^{81}$, —SO$_2$R$^{82}$, or S(O)$_2$ OH;

$R^3$ is alkyl, —CH(CH$_3$)$_2$, CF$_3$, Br, sulfonamido, —S(O)R$^{81}$, —SO$_2$R$^{82}$, nitro, pentafluorosulfanyl, C(O)OH, amide, or ester;

$R^4$, $R^5$, $R^6$, and $R^7$ are each independently H or alkyl;

$R^{81}$ is independently at each occurrence alkyl, cycloalkyl, alkenyl, alkynyl, aryl, aralkyl, heterocyclyl or heterocyclylalkyl; and $R^{82}$ is independently at each occurrence alkyl, cycloalkyl, alkenyl, alkynyl, aryl, aralkyl, heterocyclyl or heterocyclylalkyl.

15. The compound of claim 14, wherein the compound is of Formula II

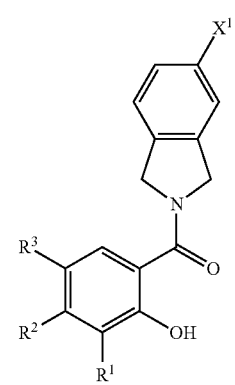

(II)

or one or both of a pharmaceutically acceptable salt thereof or a solvate thereof.

16. The compound of claim 14, wherein $X^5$ is OH, F, Cl, Br, CN, —C(O)—NH$_2$, —NH—C(O)H, —NH—C(O)-alkyl, —C(O)H, or —C(O)OH.

17. A composition comprising a compound of claim 14 and a pharmaceutically acceptable carrier.

18. A pharmaceutical composition comprising an effective amount of a compound of claim 14 and a pharmaceutically acceptable carrier, wherein the effective amount is effective for treating non-small cell lung cancer, bladder cancer, or colon cancer.

19. A method of selectively inhibiting Hsp90β over Hsp90α, wherein the method comprises administering a compound of claim 14 to a cancer cell or to a subject.

20. A compound according to Formula I

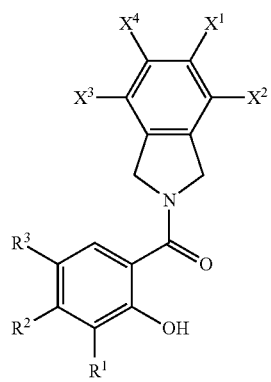
(I)

or one or both of a pharmaceutically acceptable salt thereof or a solvate thereof, wherein $X^1$, $X^2$, $X^3$, and $X^4$ are each independently selected from H, F, Cl, Br, I, nitro, pentafluorosulfanyl, C(O)OH, amide, or ester;

$R^1$ and $R^2$ together are, moving in the direction from $R^2$ to $R^1$, —C($X^{10}$)—N($R^{15}$)—CH($R^{16}$)—CH($R^{17}$)—, —O—CH=CH—, —O—N=CH—, —NH—CH=N—, or —CH=N—NH—;

$X^{10}$ is O, CH$_2$, or CF$_2$;

$R^3$ is alkyl, —CH(CH$_3$)$_2$, CF$_3$, Br, sulfonamido, nitro, pentafluorosulfanyl, C(O)OH, amide, or ester;

$R^{15}$ is H or C$_1$-C$_3$ alkyl; and $R^{16}$ and $R^{17}$ are each independently selected from H, C$_1$-C$_3$ alkyl, F, Cl, Br, I, or CF$_3$.

21. The compound of claim 20, wherein the compound is

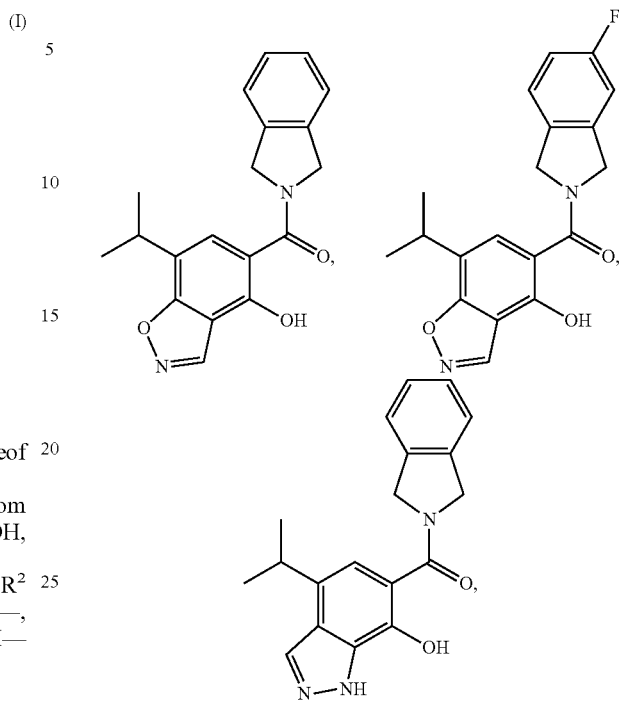

or one or both of a pharmaceutically acceptable salt thereof or a solvate thereof.

* * * * *

UNITED STATES PATENT AND TRADEMARK OFFICE
CERTIFICATE OF CORRECTION

PATENT NO. : 10,927,076 B2
APPLICATION NO. : 16/477398
DATED : February 23, 2021
INVENTOR(S) : Blagg et al.

It is certified that error appears in the above-identified patent and that said Letters Patent is hereby corrected as shown below:

In the Specification

Please update Column 1, Lines 18-19 to read:
This invention was made with government support under grant number CA120458 and CA109265 awarded by the National Institutes of Health. The government has certain rights in the invention.

Signed and Sealed this
Twentieth Day of April, 2021

Drew Hirshfeld
*Performing the Functions and Duties of the*
*Under Secretary of Commerce for Intellectual Property and*
*Director of the United States Patent and Trademark Office*